United States Patent
Hanajima et al.

(10) Patent No.: US 12,090,003 B2
(45) Date of Patent: Sep. 17, 2024

(54) MEDICAL INSTRUMENT DISPLAYS AND MEDICAL INSTRUMENT DISPLAY PROGRAMS

(71) Applicants: Roland DG Corporation, Hamamatsu (JP); Hamamatsu University School of Medicine, Hamamatsu (JP)

(72) Inventors: Masaki Hanajima, Hamamatsu (JP); Takaaki Kokubo, Hamamatsu (JP); Takeshi Tsuji, Hamamatsu (JP); Akinori Sugaya, Hamamatsu (JP); Naomi Ishino, Hamamatsu (JP)

(73) Assignees: ROLAND DG CORPORATION, Shizuoka (JP); Hamamatsu University School of Medicine, Shizuoka (JP)

( * ) Notice: Subject to any disclaimer, the term of this patent is extended or adjusted under 35 U.S.C. 154(b) by 1200 days.

(21) Appl. No.: 16/338,825

(22) PCT Filed: Sep. 27, 2017

(86) PCT No.: PCT/JP2017/034953
§ 371 (c)(1),
(2) Date: Apr. 2, 2019

(87) PCT Pub. No.: WO2018/066429
PCT Pub. Date: Apr. 12, 2018

(65) Prior Publication Data
US 2020/0038136 A1    Feb. 6, 2020

(30) Foreign Application Priority Data

Oct. 3, 2016 (JP) ................. 2016-195814
Oct. 3, 2016 (JP) ................. 2016-195937
Oct. 3, 2016 (JP) ................. 2016-195968

(51) Int. Cl.
*A61B 90/00* (2016.01)
*G06F 16/21* (2019.01)
(Continued)

(52) U.S. Cl.
CPC ............ *A61B 90/37* (2016.02); *G06F 16/219* (2019.01); *G06T 3/40* (2013.01); *G16H 40/40* (2018.01);
(Continued)

(58) Field of Classification Search
None
See application file for complete search history.

(56) References Cited

U.S. PATENT DOCUMENTS 7,669,142 B2 * 2/2010 Ray ..................... G06F 16/9577
715/845
10,073,889 B2 * 9/2018 Fukuda ............... G06F 16/2428
(Continued)

FOREIGN PATENT DOCUMENTS

JP      11-085876 A     3/1999
JP      2004-038594 A   2/2004
(Continued)

OTHER PUBLICATIONS

Takushi Nagata, "The medical equipment preparation support apparatus", Nov. 8, 2012, translated JP2012-215990 (Year: 2012).*
(Continued)

*Primary Examiner* — David H Chu
(74) *Attorney, Agent, or Firm* — Keating & Bennett, LLP

(57) ABSTRACT

A medical instrument display includes an image storage that stores a plurality of image data of a medical instrument, a data analyzer that searches a plurality of image data stored in the image storage on a certain condition, and a display controller that causes a display to display a first medical instrument image that has been selected from thumbnail
(Continued)

images, the thumbnail images being based on a plurality of the image data obtained by the search, and a second medical instrument image in good order, the second medical instrument image being different from the first medical instrument image.

7 Claims, 53 Drawing Sheets

(51) Int. Cl.
G06T 3/40 (2006.01)
G16H 40/40 (2018.01)
A61B 34/30 (2016.01)

(52) U.S. Cl.
CPC ....... A61B 34/30 (2016.02); A61B 2090/0803 (2016.02); A61B 2090/0807 (2016.02); A61B 2560/0266 (2013.01)

(56) References Cited

U.S. PATENT DOCUMENTS

| | | |
|---|---|---|
| 2006/0059018 A1 | 3/2006 | Shiobara et al. |
| 2007/0174790 A1* | 7/2007 | Jing ................. G06F 3/0485 715/838 |
| 2015/0365786 A1* | 12/2015 | Mizumoto ........ H04M 1/27475 455/41.2 |

FOREIGN PATENT DOCUMENTS

| | | |
|---|---|---|
| JP | 2005-237586 A | 9/2005 |
| JP | 2006-006671 A | 1/2006 |
| JP | 2006-178919 A | 7/2006 |
| JP | 2008-033783 A | 2/2008 |
| JP | 2008-054732 A | 3/2008 |
| JP | 2011-076445 A | 4/2011 |
| JP | 2012215990 A * | 11/2012 |
| JP | 2015-087875 A | 5/2015 |

OTHER PUBLICATIONS

Official Communication issued in International Patent Application No. PCT/JP2017/034953, mailed on Dec. 19, 2017.
Hanajima et al., "Medical Instrument Displays and Medical Instrument Display Programs", U.S. Appl. No. 17/958,483, filed Oct. 3, 2022.
Hanajima et al., "Medical Instrument Displays and Medical Instrument Display Programs", U.S. Appl. No. 17/958,484, filed Oct. 3, 2022.

* cited by examiner

| IMAGE ID | IMAGE DATA | MEDICAL INSTRUMENT NAME | IDENTIFICATION ID | INDIVIDUAL INSTRUMENT NAME | NUMBER |
|---|---|---|---|---|---|
| I-1 | J1 | SURGICAL ROBOT COMMON SURGICAL SET | D-1 | INSTRUMENT α<br>INSTRUMENT β<br>INSTRUMENT γ | 5 |
| I-2 | J2 | SURGICAL ROBOT ADDITIONAL SURGICAL SET | D-2 | INSTRUMENT α<br>INSTRUMENT δ | 3 |
| .... | .... | .... | .... | .... | .... |
| I-16 | J16 | RIGID ENDOSCOPE | D-16 | — | 1 |
| .... | .... | .... | .... | .... | .... |
| I-30 | J30 | MICRO-SET FOR BRAIN SURGERY | D-30 | RASPATORY ε−1<br>RASPATORY ε−2<br>FORCEPS ζ−3<br>....<br>TWEEZERS η−14 | 14 |
| .... | .... | .... | .... | .... | .... |

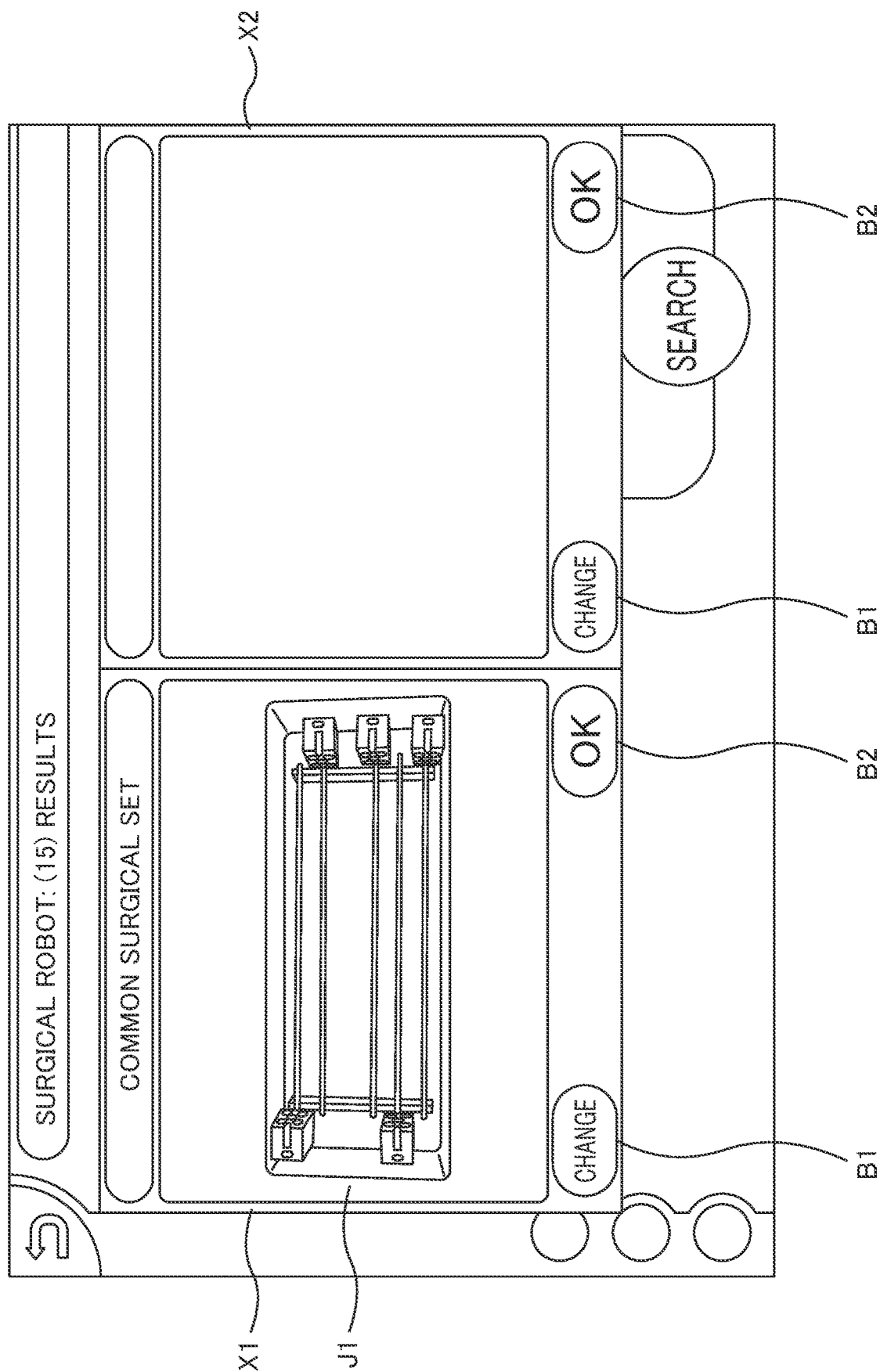

| IMAGE ID | IMAGE DATA | MEDICAL INSTRUMENT NAME | IDENTIFICATION ID | INDIVIDUAL INSTRUMENT NAME | NUMBER | SIMILAR IMAGE ID |
|---|---|---|---|---|---|---|
| I-1 | J1 | SURGICAL ROBOT COMMON SURGICAL SET | D-1 | INSTRUMENT α<br>INSTRUMENT β<br>INSTRUMENT γ | 5 | I-2 |
| I-2 | J2 | SURGICAL ROBOT ADDITIONAL SURGICAL SET | D-2 | INSTRUMENT α<br>INSTRUMENT δ | 3 | I-1<br>I-3<br>I-4 |
| .... | ... | ... | .... | .... | .... | .... |

FIG. 6

| IMAGE ID | IMAGE DATA | MEDICAL INSTRUMENT NAME | IDENTIFICATION ID | INDIVIDUAL INSTRUMENT NAME | NUMBER | ENLARGED IMAGE DATA |
|---|---|---|---|---|---|---|
| I-30 |  J30 | MICRO-SET FOR BRAIN SURGERY | D-30 | RASPATORY ε−1<br>RASPATORY ε−2<br>FORCEPS ζ−3<br>...<br>TWEEZERS η−14 | 14 |  EJ1 ....  EJ14 |
| .... | .... | .... | .... | .... | .... | .... |
FIG. 8

| IMAGE ID | IMAGE DATA | MEDICAL INSTRUMENT NAME | IDENTIFICATION ID | NUMBER | INDIVIDUAL INSTRUMENT NAME | INDIVIDUAL IMAGE DATA |
|---|---|---|---|---|---|---|
| I-30 | J30 | MICRO-SET FOR BRAIN SURGERY | D-30 | 14 | RASPATORY $\varepsilon$-1 | IJ1 |
| | | | | | RASPATORY $\varepsilon$-2 | IJ2 |
| | | | | | FORCEPS $\zeta$-3 | IJ3 |
| | | | | | .... | .... |
| | | | | | TWEEZERS $\eta$-14 | IJ14 |
| .... | .... | .... | .... | .... | .... | .... |

FIG. 9

| IMAGE ID | IMAGE DATA | MEDICAL INSTRUMENT NAME | IDENTIFICATION ID | NUMBER | INDIVIDUAL INSTRUMENT NAME | INDIVIDUAL INSTRUMENT ID |
|---|---|---|---|---|---|---|
| I-1 | 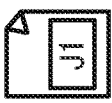 | SURGICAL ROBOT COMMON SURGICAL SET | D-1 | 5 | INSTRUMENT α | E-1 |
| | | | | | INSTRUMENT β | E-2 |
| | | | | | INSTRUMENT γ | — |
| I-2 | 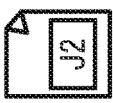 | SURGICAL ROBOT ADDITIONAL SURGICAL SET | D-2 | 3 | INSTRUMENT α | E-3 |
| | | | | | INSTRUMENT δ | — |
| .... | | .... | .... | .... | .... | |
FIG. 11

| UPPER-LEVEL PROCESS ORDER | OPERATION NAME | IMAGE DESIGNATION |
|---|---|---|
| 1 | ASSEMBLAGE | 153.jpg |
| 2 | STERILIZATION | 154.jpg |
| . | . | |
| . | . | |
| . | . | |

45 → (row 1)
45 → (row 2)

FIG. 16

| UPPER-LEVEL PROCESS ORDER | MAIN PROCESS ORDER | OPERATION DETAIL | CLASSIFICATION | IMAGE DESIGNATION | PRESENCE/ABSENCE OF SUB PROCESS |
|---|---|---|---|---|---|
| 1 | 1 | CHECK MEDICAL INSTRUMENT | NORMAL OPERATION | 01.jpg | NO |
| 1 | 2 | INSPECT MEDICAL INSTRUMENT | QUALITY IMPORTANT OPERATION | 03.jpg | YES |
| 1 | 3 | CHECK PARTS AND NUMBER OF PARTS | COUNT OPERATION | 05.jpg, 06.jpg, ...10.jpg | NO |
| 1 | 4 | ASSEMBLE MEDICAL INSTRUMENT | QUALITY IMPORTANT OPERATION | 18.jpg | YES |
| 2 | 1 | CHECK STERILIZER | NORMAL OPERATION | 01.jpg | NO |
| . | . | . | . | . | . |

FIG. 17

| UPPER-LEVEL PROCESS ORDER | MAIN PROCESS ORDER | SUB PROCESS ORDER | OPERATION DETAIL | IMAGE DESIGNATION |
|---|---|---|---|---|
| 1 | 2 | 1 | INSPECT DETAILS OF MEDICAL INSTRUMENT | 22.jpg |
| 1 | 2 | 2 | INSPECT DETAILS OF MEDICAL INSTRUMENT | 23.jpg |
| 1 | 4 | 1 | ASSEMBLE PARTS | 41.jpg |
| 1 | 4 | 2 | ASSEMBLE PARTS | 42.jpg |
| 2 | 1 | 1 | OPEN DOOR OF STERILIZER | 102.jpg |
| ... | ... | ... | ... | ... |

FIG. 18

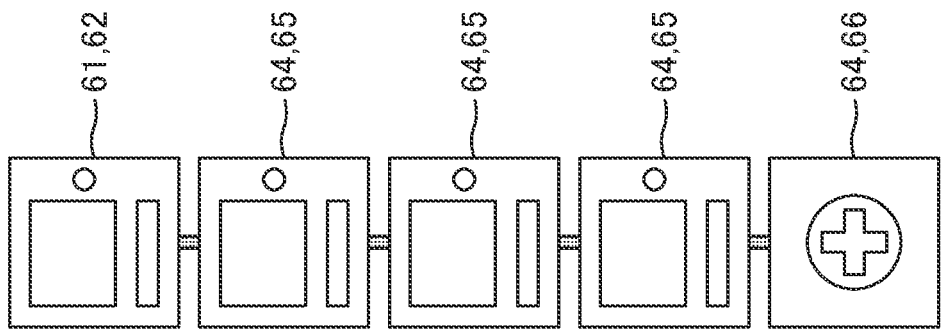
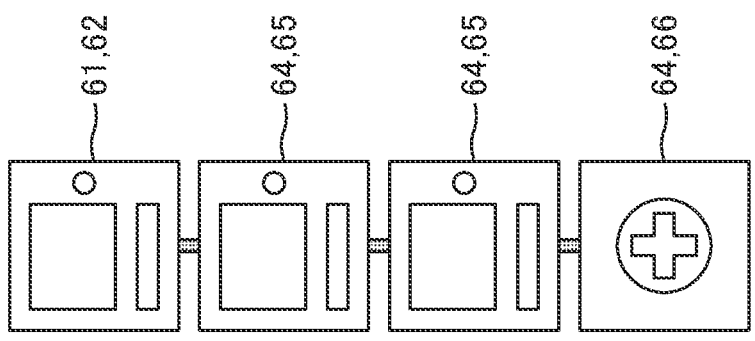
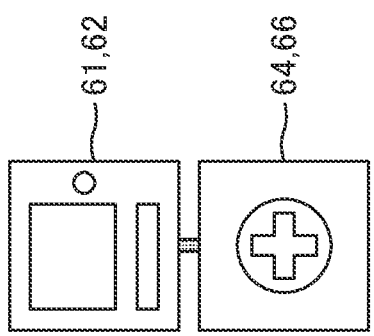

| UPPER-LEVEL PROCESS ORDER | OPERATION NAME | IMAGE DESIGNATION |
|---|---|---|
| 1 | ASSEMBLAGE | 153.jpg |
| 2 | STERILIZATION | 154.jpg |
| . . . | . . . | |

45 → (row 1)
45 → (row 2)

FIG. 33

| UPPER-LEVEL PROCESS ORDER | MAIN PROCESS ORDER | OPERATION DETAIL | CLASSIFICATION | IMAGE DESIGNATION | PRESENCE/ABSENCE OF SUB PROCESS |
|---|---|---|---|---|---|
| 1 | 1 | CHECK MEDICAL INSTRUMENT | NORMAL OPERATION | 01.jpg | NO |
| 1 | 2 | INSPECT MEDICAL INSTRUMENT | QUALITY IMPORTANT OPERATION | 03.jpg | YES |
| 1 | 3 | CHECK PARTS AND NUMBER OF PARTS | COUNT OPERATION | 05.jpg, 06.jpg, ···10.jpg | NO |
| 1 | 4 | ASSEMBLE MEDICAL INSTRUMENT | QUALITY IMPORTANT OPERATION | 18.jpg | YES |
| 2 | 1 | CHECK STERILIZER | NORMAL OPERATION | 01.jpg | NO |
| ... | ... | ... | ... | ... | ... |

FIG. 34

| UPPER-LEVEL PROCESS ORDER | MAIN PROCESS ORDER | SUB PROCESS ORDER | OPERATION DETAIL | IMAGE DESIGNATION |
|---|---|---|---|---|
| 1 | 2 | 1 | INSPECT DETAILS OF MEDICAL INSTRUMENT | 22.jpg |
| 1 | 2 | 2 | INSPECT DETAILS OF MEDICAL INSTRUMENT | 23.jpg |
| 1 | 4 | 1 | ASSEMBLE PARTS | 41.jpg |
| 1 | 4 | 2 | ASSEMBLE PARTS | 42.jpg |
| 2 | 1 | 1 | OPEN DOOR OF STERILIZER | 102.jpg |
| ... | ... | ... | ... | |

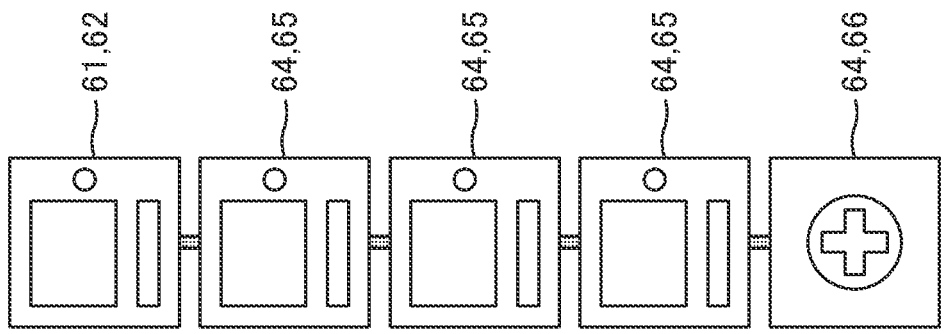
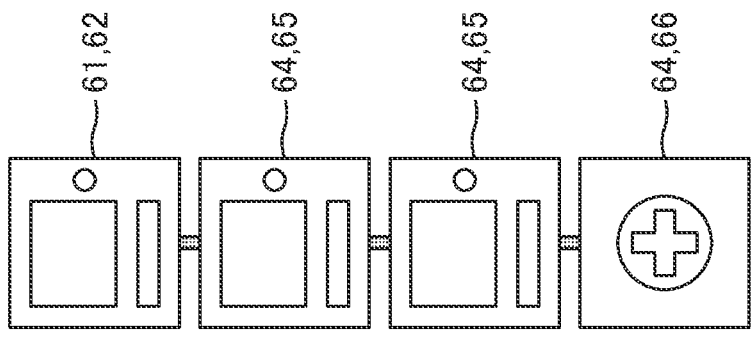
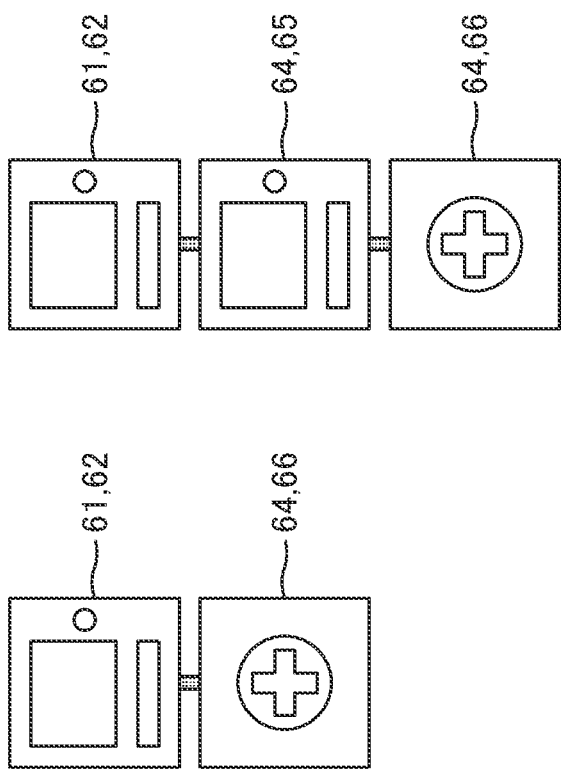

| VERSION NUMBER | CONTENT IDENTIFIER | CONTENT NAME | FILE STORAGE PLACE (FILE ADDRESS) | STORAGE TIME | EDITOR | REASON OF EDIT | APPROVER | DATE OF APPROVAL |
|---|---|---|---|---|---|---|---|---|
| 001 | 001 | ENDOSCOPE CLEANING | /001/001/ | 2014/4/4 15:15 | A | CREATE NEW | C | 2014/4/4 15:45 |
| 002 | 001 | ENDOSCOPE CLEANING | /001/002/ | 2014/4/4 16:30 | B | CHANGE MAINTENANCE PROCEDURE | C | 2014/4/8 12:30 |
| 003 | 001 | ENDOSCOPE CLEANING | /001/003/ | 2015/1/7 18:13 | A | ADD NUMBER CHECK OPERATION | C | 2015/1/9 13:12 |
| 004 | 001 | ENDOSCOPE CLEANING | /001/004/ | 2015/2/8 10:23 | A | CHANGE NAME | C | 2015/2/9 13:43 |
| 005 | 001 | ENDOSCOPE CLEANING | /001/005/ | 2015/3/4 15:32 | B | CORRECT ERRORS | C | 2015/3/4 18:22 |
| 006 | 001 | ENDOSCOPE CLEANING | /001/007/ | 2015/6/20 7:22 | B | ADD QUALITY CHECK OPERATION | C | 2015/6/25 8:36 |

FIG. 47

| USE TIMES | USED VERSION | DATE AND TIME OF USE | USER |
|---|---|---|---|
| 001 | 006 | 2015/6/21 7:22 | D |
| 002 | 005 | 2015/6/22 18:22 | E |
| 003 | 006 | 2015/6/23 8:31 | C |
| 004 | 006 | 2015/6/24 10:22 | A |
| 005 | 004 | 2015/6/25 9:23 | E |
| 006 | 006 | 2015/6/26 13:22 | E |

FIG. 48

MEDICAL INSTRUMENT DISPLAYS AND MEDICAL INSTRUMENT DISPLAY PROGRAMS

BACKGROUND OF THE INVENTION

1. Field of the Invention

The present invention according to the present preferred embodiments relates to medical instrument displays and medical instrument display programs.

2. Description of the Related Art

There are many similar models of medical instruments used for surgeries and examinations in patients. For example, surgical forceps have handles of the same shape but have tips of different shapes depending on their purpose or regions where they are used. As a result, it is difficult for those who are not familiar with these instruments to distinguish them.

Consequently, errors can occur, such as confusion of instrument choice or the use of a wrong procedure for cleaning or sterilization (e.g., cleaning or sterilization of an instrument using a procedure that is different from what should be used) during a step or steps in collecting a used medical instrument; in cleaning, assembling, sterilizing, or storing a medical instrument; or in delivering a medical instrument for surgery.

Furthermore, medical instruments may be used as a set of instruments. Some of these sets are different from each other in terms of only some of their contents, and others are different from each other in terms of only the number of the same instruments. Some sets are similar to each other in terms of their names but quite different from each other in terms of their contents. Accordingly, errors such as confusion of instrument choice (wrong choice of instruments, mistakes in number of them) or the use of a wrong procedure can particularly occur.

In actual medical fields, to prevent such mistakes, operations of preparing photographs of medical instruments beforehand and comparing the photographs with medical instruments close at hand to check whether there is no mistake.

Furthermore, checking operations by referring to images of medical instruments entered beforehand into a database can be contemplated. For example, JP-A-2012-215990 describes a device for assisting picking operations for medical instruments of medical instruments used for medical practices. Specifically, an instrument attribute storage part stores a medical instrument identifier for a medical instrument and an image of a medical instrument. A similar instrument storage part stores information about medical instruments that are similar to each other. A handled instrument list acquisition part acquires a handled instrument list that is a list of medical instruments used for medical practices. An instrument acceptance part accepts an instruction input of a user who designate one of the medical instruments included in the handled instrument list. A similar instrument acquisition part acquires, from a similar instrument storage part, a medical instrument identifier for a medical instrument that is similar to the designated medical instrument designated by a user. A screen generation part reads the image of the designated medical instrument and the image of the similar medical instrument from the instrument attribute storage part and generates a screen for displaying these images.

As described above, since there are many similar models and various sets of medical instruments, it is preferable to visually compare, when a medical instrument close at hand is subjected to a checking operation, the medical instrument with a plurality of images of medical instruments.

SUMMARY OF THE INVENTION

Preferred embodiments of the present invention provide medical instrument displays and non-transitory computer-readable media including medical instrument display programs with which images of a plurality of medical instruments are able to be displayed in good order.

According to a preferred embodiment of the present invention, a medical instrument display includes an image storage that stores a plurality of image data of a medical instrument; a data analyzer that searches image data stored in the image storage on a certain condition; and a display controller that causes a display to display a first medical instrument image that has been selected from thumbnail images, the thumbnail images being based on a plurality of the image data obtained by the search, and a second medical instrument image in good order, the second medical instrument image being different from the first medical instrument image.

Other features of preferred embodiments of the present invention will be disclosed in the description of the specification.

Preferred embodiments of the present invention provide images of a plurality of medical instruments to be displayed in good order.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 4 is a diagram showing an example of data stored in an image storage according to the first preferred embodiment of the present invention.

FIG. 5C is a diagram showing a display screen on the terminal of the first preferred embodiment of the present invention.

FIG. 5D is a diagram showing a display screen on the terminal of the first preferred embodiment of the present invention.

FIG. 6 is a diagram showing an example of data stored in the image storage according to the first preferred embodiment of the present invention.

FIG. 8 is a diagram showing an example of data stored in an image storage according to the second preferred embodiment of the present invention.

FIG. 9 is a diagram showing an example of data stored in an image storage according to a third preferred embodiment of the present invention.

FIG. 11 is a diagram showing an example of data stored in an image storage according to a fourth preferred embodiment of the present invention.

FIG. 16 is a diagram schematically showing a configuration of an upper-level process data.

FIG. 17 is a diagram schematically showing a configuration of a main process data.

FIG. 18 is a diagram schematically showing a configuration of a sub process data.

FIG. 28 is a diagram illustrating that unregistered widgets of a sub process are successively displayed in a vertical direction in the order of 28A to 28D.

FIG. 33 is a diagram schematically showing a configuration of an upper-level process data.

FIG. 34 is a diagram schematically showing a configuration of a main process data.

FIG. 35 is a diagram schematically showing a configuration of a sub process data.

FIG. 45 is a diagram illustrating that unregistered widgets of a sub process are successively displayed in a vertical direction in the order of 45A to 45D.

FIG. 47 is a diagram schematically showing a configuration of a version management table.

FIG. 48 is a diagram schematically showing a configuration of a use history log.

DETAILED DESCRIPTION OF THE PREFERRED EMBODIMENTS

Figure 1:
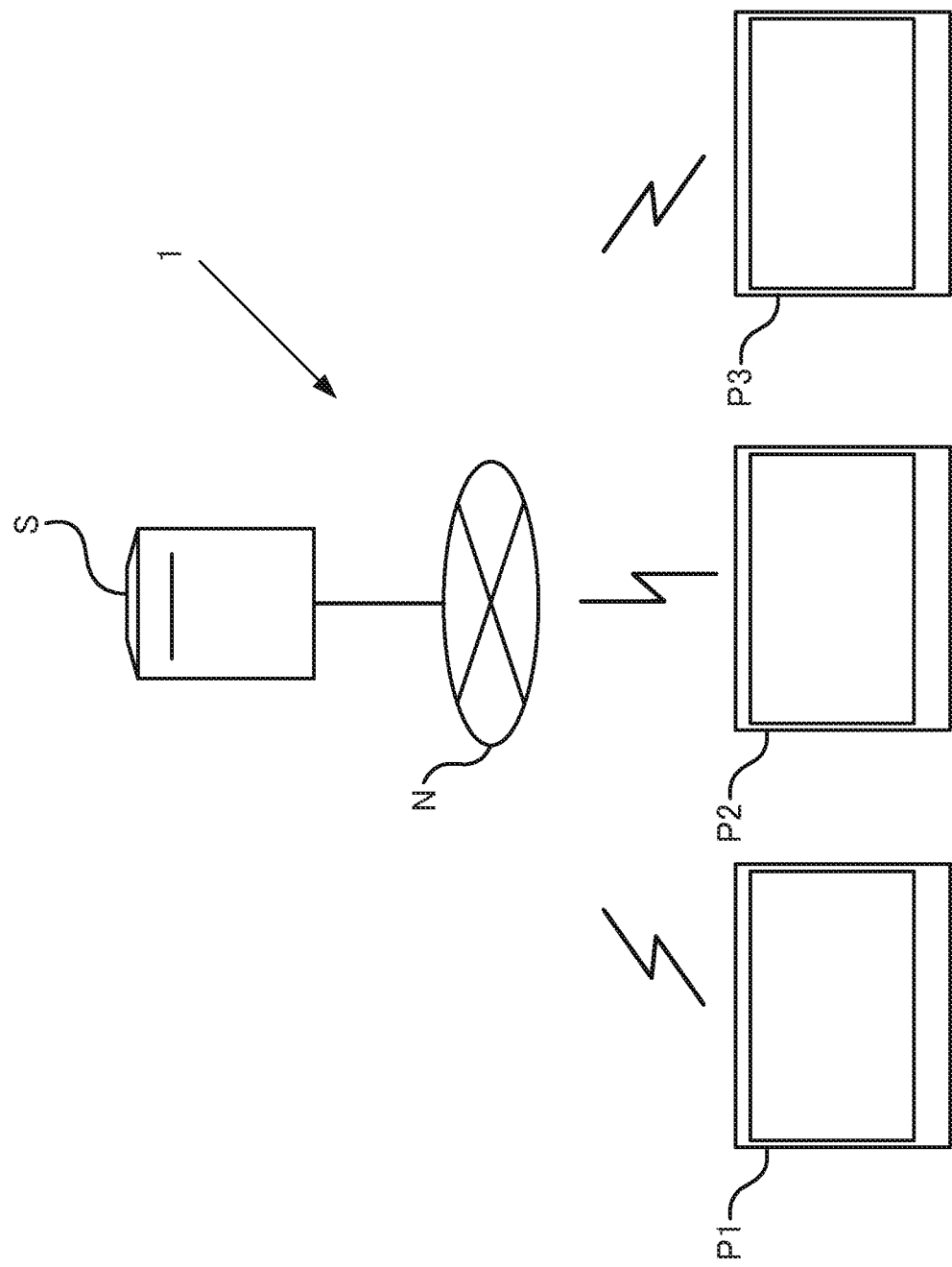
FIG. 1 is a diagrammatic representation showing a configuration of an operation assistance system according to a first preferred embodiment of the present invention.

In the descriptions of the specification and the drawings that follow, at least the following features are disclosed with reference to various preferred embodiments of the present invention.

That is, a medical instrument display in which a second medical instrument image has been selected from thumbnail images is disclosed. In this case, a plurality of images of an operator's free choice can be displayed in good order.

Furthermore, a medical instrument display in which the image data of a medical instrument are associated with image data of a similar medical instrument, and a display controller causes the second medical instrument image to be displayed based on an image data of a similar medical instrument associated with the first medical instrument image. With such medical instrument displays, similar images can be displayed in good order for a single image.

Furthermore, a medical instrument display in which a display controller is capable of causing the display to display either one of the first medical instrument image and the second medical instrument image is disclosed. With such medical instrument displays, only the image which an operator wants to focus on is able to be displayed among the images that have been displayed in good order.

Furthermore, a medical instrument display in which a display controller causes a designated area be enlarged and displayed, the designated area being in the first medical instrument image or the second medical instrument image that has been displayed, is disclosed. With such medical instrument displays, it is possible to enlarge and display an area which an operator wants to focus on, etc.

Furthermore, a medical instrument display in which image data of a medical instrument is associated with an enlarged image data in which the medical instrument has been partially enlarged, and the display controller causes an image based on the enlarged image data to be displayed is disclosed. With such medical instrument displays, it is possible to easily display an image of an area that should be focused on, etc.

Furthermore, a medical instrument display in which a medical instrument is a set including a plurality of instruments, the image data of a medical instrument are associated with image data of each of the instruments included in the set, and the display controller causes images based on the image data of the respective instruments to be displayed. With such medical instrument displays, it is possible to individually display instruments included in a medical instrument.

Alternatively, a medical instrument display including an image storage that stores a plurality of image data of a medical instrument corresponding to a set including a plurality of instruments; a data analyzer that searches image data stored in the image storage; and a display controller that causes a display to display an image based on the image data of a medical instrument, wherein at least one of the instruments included in one of the sets is assigned with an identifier, the data analyzer searches, based on the identifier, a plurality of medical images for an image data of a medical instrument that includes an instrument assigned with the identifier, and the display controller causes display of an image based on the searched image data is disclosed. With such medical instrument displays, it is possible to display, based on an identifier assigned to a certain instrument, an image of a set including the instrument.

Furthermore, a non-transitory computer-readable medium including a medical instrument display program for causing a computer including an image storage that stores a plurality of image data of a medical instrument and a display, to search the image data stored in the image storage on a certain condition; cause the display to display thumbnail images, the thumbnail images being based on a plurality of the image data obtained by the search; cause a first display portion of the display to display a first medical instrument image selected from the thumbnail images; and cause a second display portion that is different from the first display portion to display a second medical instrument image that is different from the first medical instrument image is disclosed. With such non-transitory computer-readable media including such programs, it is possible to display a plurality of images of a medical instrument in good order.

First Preferred Embodiment

Referring to FIGS. 1 to 6, an operation assistance system 1 according to a first preferred embodiment of the present invention is described. It should be noted that an "image" and an "image data" correspond to each other one by one and thus they may be equated with each other in the present specification.

Medical instruments are, for example, those used for surgery such as pairs of surgical forceps, scalpels, and rigid endoscopes and those used for examinations such as pairs of biopsy forceps, ultrasonic probes, and upper and lower endoscopes. Medical instruments in this preferred embodiment include a set of instruments (such as a surgical kit including pairs of forceps, scalpels, and pairs of scissors), for example.

As shown in FIG. 1, the operation assistance system includes a plurality of terminals (in this example, three terminals: a "terminal P1," a "terminal P2," and a "terminal P3") and a server S. The terminals P1 to P3 can communicate with the server S via a network N. The network N is, for example, a leased-line network in a hospital facility or the Internet.

The server S is a computer that accumulates and manages various kinds of information associated with medical instruments and exchanges various kinds of information with the terminals P1 to P3. Furthermore, the server S has a function of interfacing the exchange of information between or among the terminals. The server S can be installed in a hospital facility where each terminal is located or installed in a remote location such as a server provider and the like.

The terminals P1 to P3 are devices configured or programmed to enter and display various kinds of information associated with medical instruments and exchange information with the server S. Each terminal is a desktop personal computer or a mobile terminal (such as a laptop PC and a tablet computer). The terminals can be located at different areas (such as an area where used medical instruments are collected, an area where medical instruments are cleaned, an area where medical instruments are assembled, an area where medical instruments are sterilized, and an area where medical instruments are stored) in a hospital facility.

The terminals of this preferred embodiment serve as devices to display images of one or more medical instruments. An operator compares images of medical instruments that have been displayed on the terminal with the actual medical instruments close at hand to check whether a proper medical instrument is selected and the instruments contained in a set of medical instruments are complete. The terminals P1 to P3 according to the present preferred embodiment are examples of a "medical instrument display."

Figure 2:
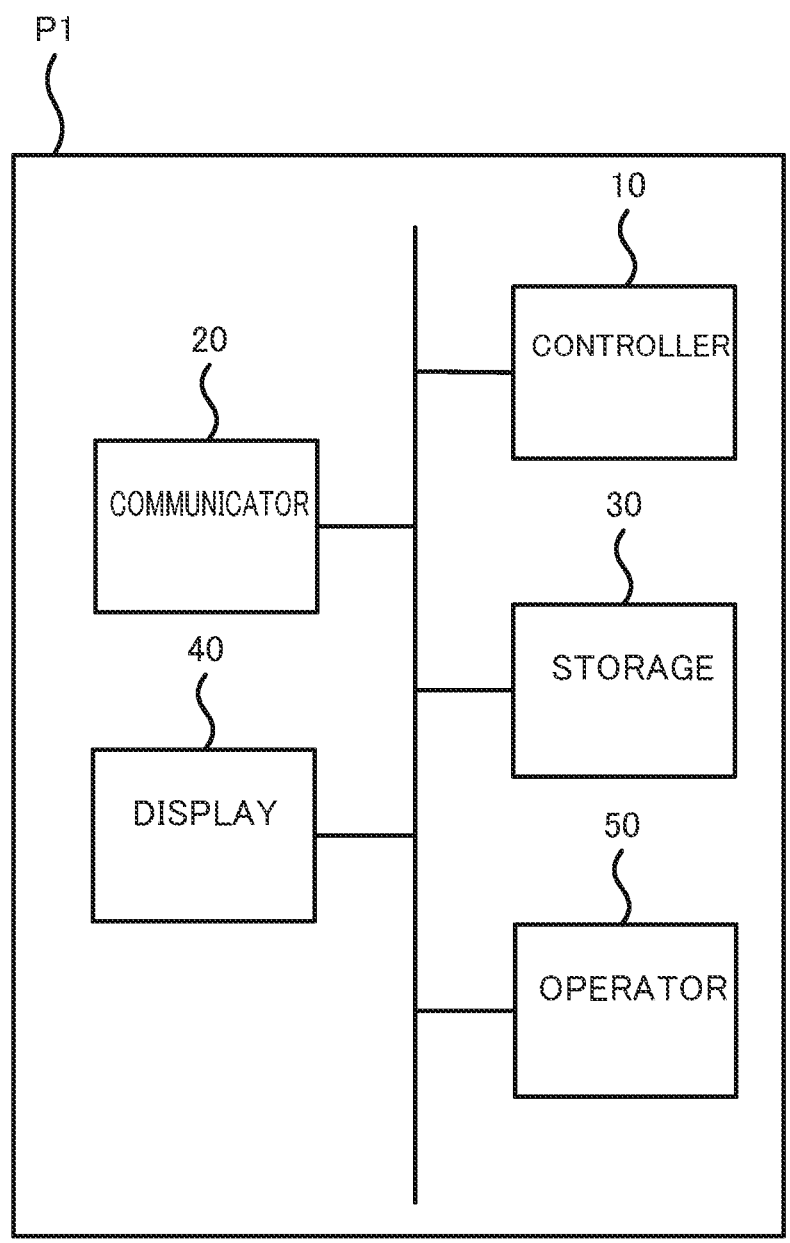
FIG. 2 is a diagram showing an exemplified hardware configuration of a medical instrument display according to the first preferred embodiment of the present invention.

Since these terminals have similar hardware configurations, the description is made using the terminal P1 as an example. As shown in FIG. 2, the terminal P1 preferably includes has a controller 10, a communicator 20, a storage 30, a display 40, and an operator 50.

The controller 10 includes a CPU and a memory (which are not shown). The CPU achieves different kinds of control functions by executing an operating program stored in the memory. The memory is a storage that stores a program or programs executed by the CPU or temporarily stores various pieces of information upon execution of the program(s).

The communicator 20 provides an interface for the communication with the server S. The storage 30 is a large-capacity storage that stores various kinds of data. The display 40 is a display that allows images of medical instruments to be displayed. The operator 50 is a structure with which an operator enters instructions to the terminal P1. The operator 50 is, for example, an input interface such as a mouse. Alternatively, the display 40 of a touch-panel screen type may double as the operator 50. The controller 10 detects an operation signal from the operator 50 and executes a corresponding processing.

Figure 3:
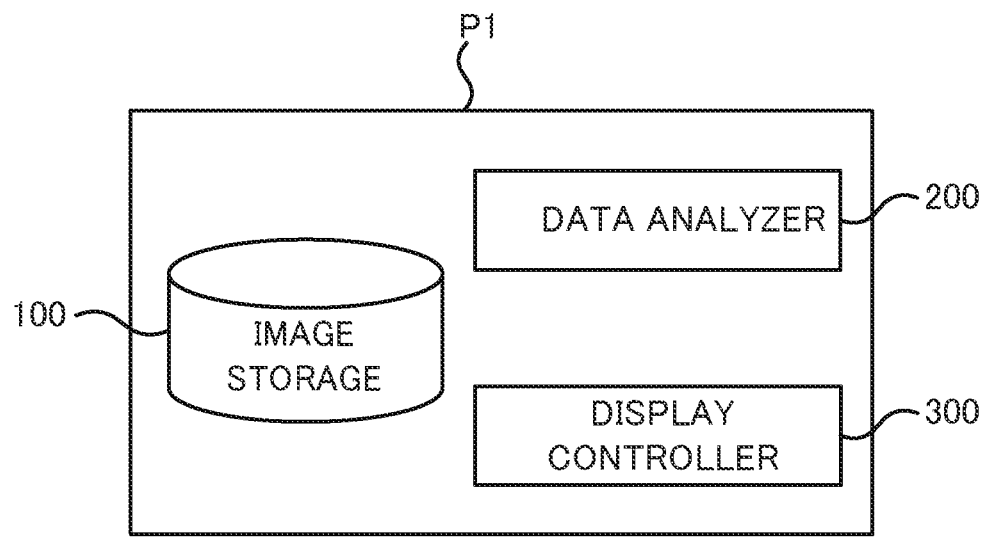
FIG. 3 is a diagram showing an exemplified software configuration of the medical instrument display according to the first preferred embodiment of the present invention.

FIG. 3 is a diagram showing an exemplified software configuration in the terminal P1. The terminal P1 includes an image storage 100, a data analyzer 200, and a display controller 300. The image storage 100 is configured as a portion of a storage region of the storage 30. The data analyzer 200 and the display controller 300 are achieved when the CPU of the controller 10 executes a program stored in the memory.

The image storage 100 stores a plurality of image data of a medical instrument. Each image data of a medical instrument is a data for displaying an image of the medical instrument on the display 40. Each image data is a photographed data itself obtained by taking a picture of a medical instrument beforehand or a CG data representing the shape of a medical instrument using computer graphics.

The image data are stored by, for example, taking, when a new medical instrument is bought, a picture of the medical instrument using a photographing device and importing that image data into a terminal. At that time, each image data of a medical instrument is assigned with a unique identifier (image ID). FIG. 4 shows an example of the data stored in the image storage 100. In this example, the image data are stored in the form of a table data in which unique image IDs as well as the names of medical instruments (the name of each instrument contained in a set when the medical instrument is a set), the number of them, and IDs for identification of medical instruments are associated thereto. The information associated with the image data is not limited to the example shown in FIG. 4 as long as it is the information for use in identifying the image data. Specific examples include the name of departments (e.g., brain surgery, general surgery, and otolaryngology) where the medical instrument is to be used, procedures, information about packages/containers, and methods of sterilization. The controller 10 can send the received image data to the server S along with, for example, its image ID.

The data analyzer 200 searches image data stored in the image storage 100 on a certain condition.

The certain condition is a condition such as a name of a medical instrument used to filter the image data. The certain condition can be entered by an operator via the operator 50. The data analyzer 200 searches the image storage 100 for the image or images that meet the received condition. The data analyzer 200 supplies the result of search (image data) to the display controller 300. This preferred embodiment is described on the assumption that two or more image data are retrieved after the search using the certain condition.

The display controller 300 performs various controls for the display in the terminal. In particular, the display controller 300 according to this preferred embodiment causes thumbnail images based on the image data obtained by the search be displayed. In addition, the display controller 300 according to this preferred embodiment causes the display 40 to display a first medical instrument image that has been selected from the thumbnail images and a second medical instrument image in good order, the second medical instrument image being different from the first medical instrument image. In this preferred embodiment, the second medical instrument image has been selected from the thumbnail images.

The display controller 300 according to this preferred embodiment is capable of causing the display 40 to display either one of the first medical instrument image and the second medical instrument image.

Here, controls performed by the display controller 300 are described using a specific example. FIGS. 5A to 5F show display screens on the display 40. Here, described is an example in which, in order to check whether all of the necessary instruments in a common surgical set for a surgical robot close at hand are complete, an image of the set and images of similar sets are made to be displayed. It is assumed that the operator knows that the set close at hand is the one of the sets used for the surgical robot but does not know the exact name of the set (common surgical set).

Figure 5A:
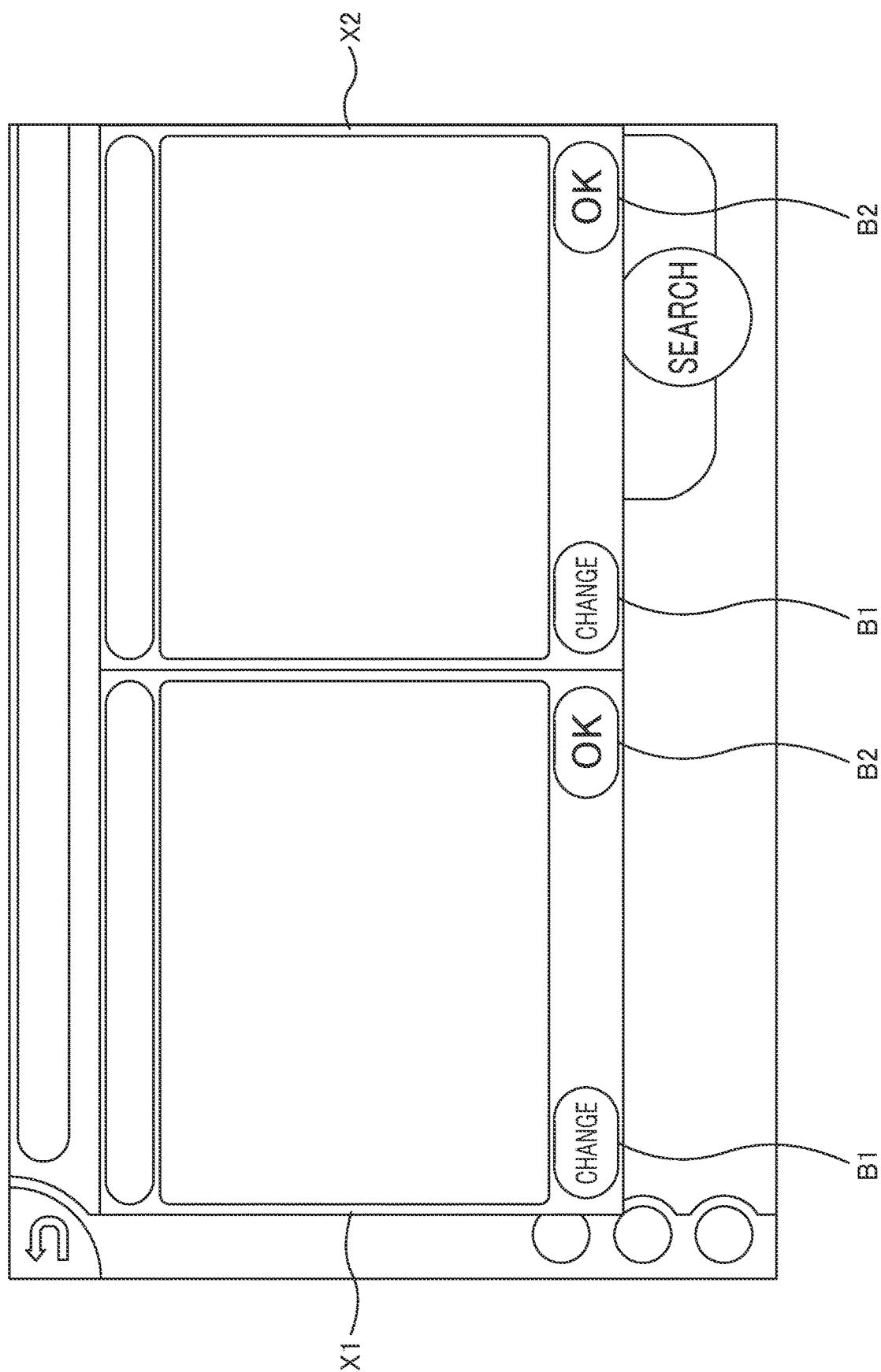
FIG. 5A is a diagram showing a display screen on a terminal of the first preferred embodiment of the present invention.
Figure 5B:
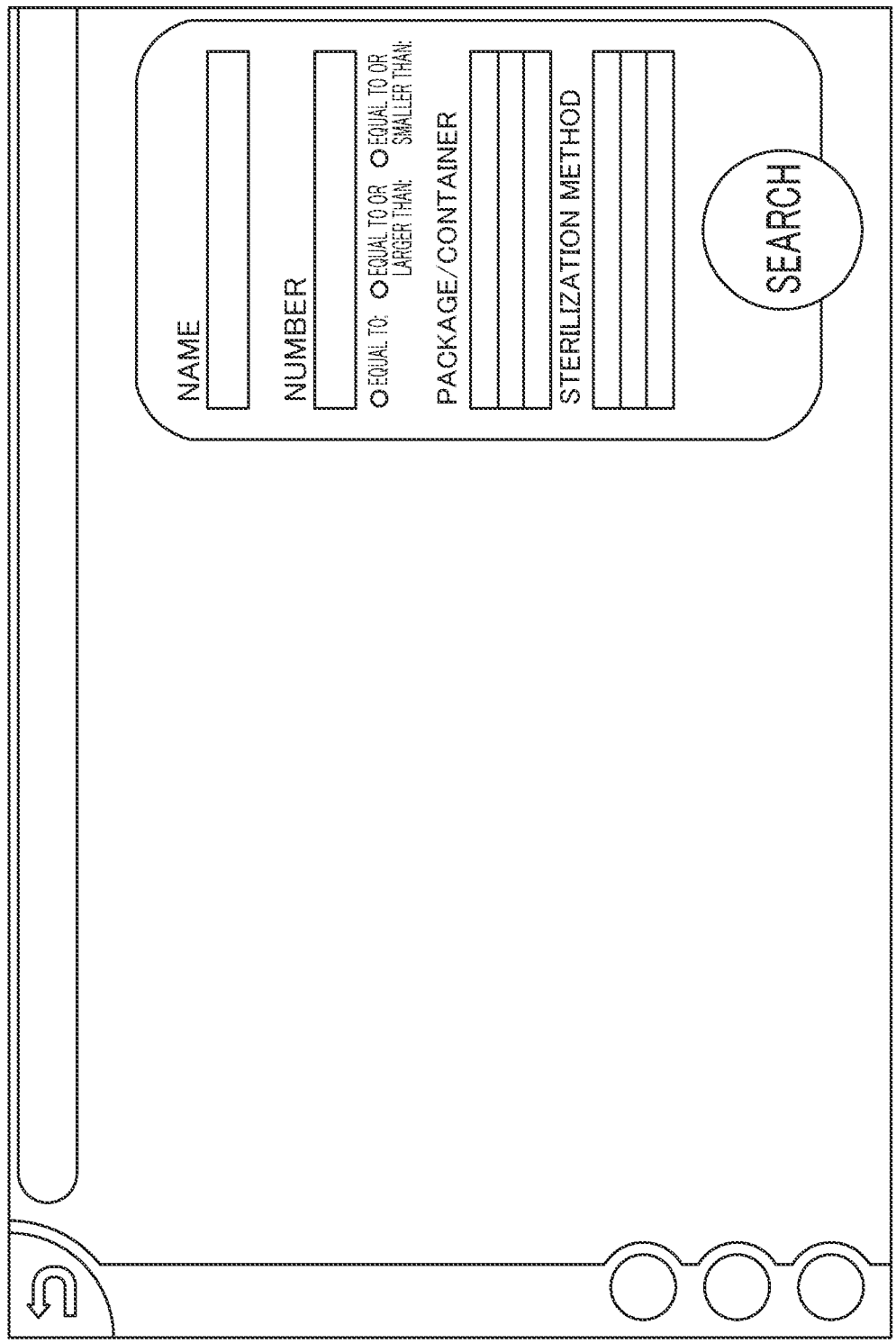
FIG. 5B is a diagram showing a display screen on the terminal of the first preferred embodiment of the present invention.

First, the display controller 300 causes the display 40 to display an instrument display screen to display medical instruments (see FIG. 5A). The instrument display screen includes a first display portion X1 to allow a medical instrument to be displayed and a second display portion X2 to allow a different medical instrument to be displayed. The display portions have a "change button B1" chosen when an image to be displayed is designated and an "OK button B2" chosen when only one of the images is to be displayed.

The operator chooses the change button B1 on the first display portion X1 of the instrument display screen. In this case, the display controller 300 switches the instrument display screen to a search screen (see FIG. 5B). The operator types the name "surgical robot" of the medical instrument he is searching for in the search screen. The data analyzer 200 searches the image storage 100 for image data with the text "search robot" included in the name of the medical instrument. The data analyzer 200 supplies the result(s) of the search (image data) to the display controller 300. In this example, it is assumed that fifteen image data (an image data J1 to the image data J15) have been retrieved. The information entered in the search screen is not limited to the name of the medical instrument and any information associated with the image data (e.g., the number, information about packages/containers, methods of sterilization) can be used.

Figure 5C:
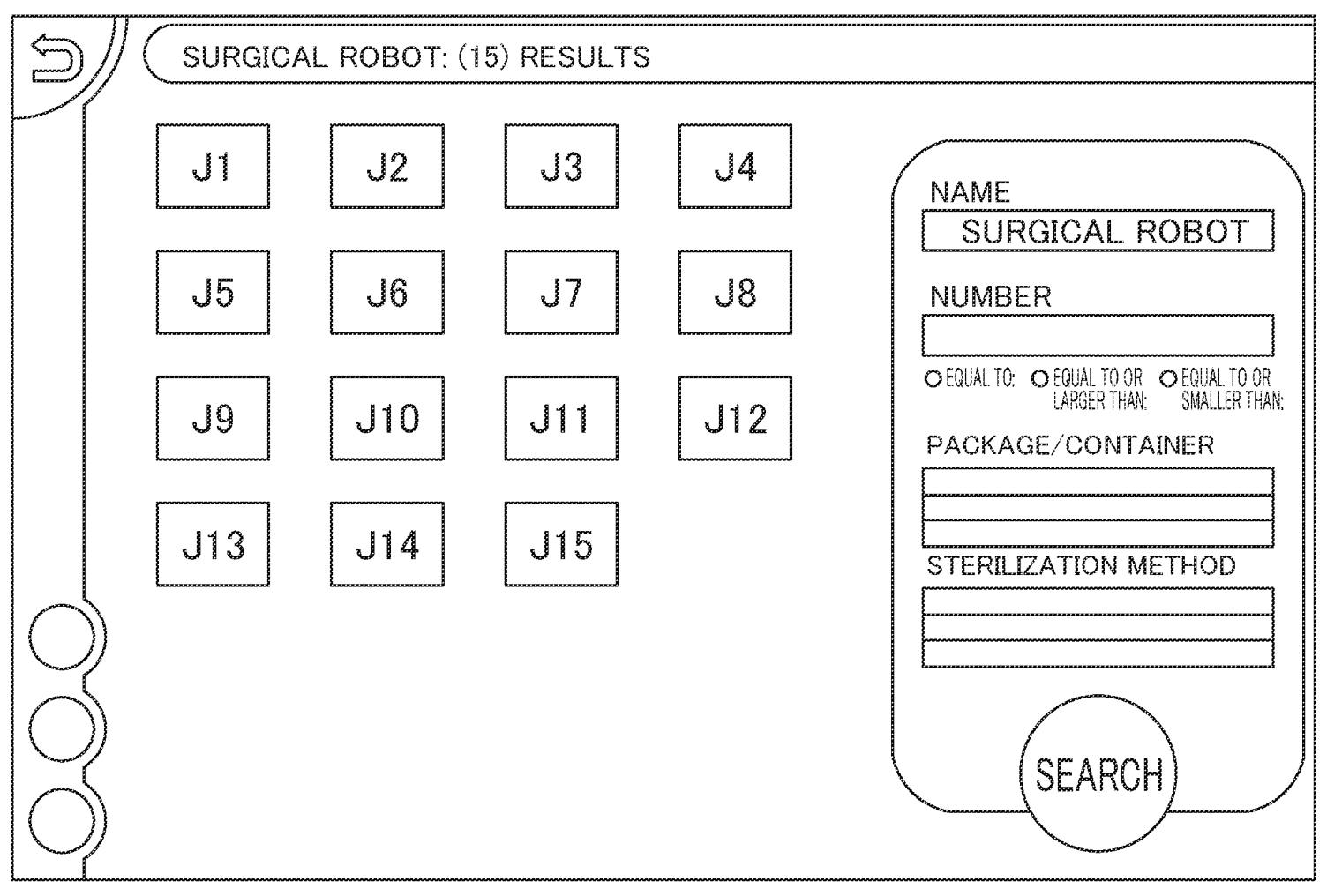

The display controller 300 generates thumbnail images (images J1 to J15) based on the retrieved image data J1 to J15 and causes the images to be displayed on the search screen (see FIG. 5C).

The operator looks at the thumbnail images and selects the image J1 (common surgical set) corresponding to a set close at hand. In this case, the display controller 300 causes the selected image J1 to be displayed on the first display portion X1 of the instrument display screen (see FIG. 5D). The image J1 is an example of a "first medical instrument image."

The operator can check whether the necessary instruments are complete by comparing the image J1 with the set of medical instruments close at hand.

Furthermore, when the thumbnail images contain one or more images other than the image J1 which the operator wants to check (such as when an image J2 similar to the image J1 is present), the operator chooses the change button B1 on the second display portion X2 of the instrument display screen. The display controller 300 switches the instrument display screen to the search screen where the thumbnail images are displayed (see FIG. 5C).

The operator looks at the thumbnail images and selects a desired image J2 (an image of additional surgical set). The display controller 300 causes the selected image J2 to be displayed on the second display portion X2 of the instrument display screen (see FIG. 5E). The image J2 is an example of a "second medical instrument image."

In this case, the operator can perform a more accurate checking operation by comparing the image J2 with the set of medical instruments close at hand or comparing two images with each other.

Figure 5E:
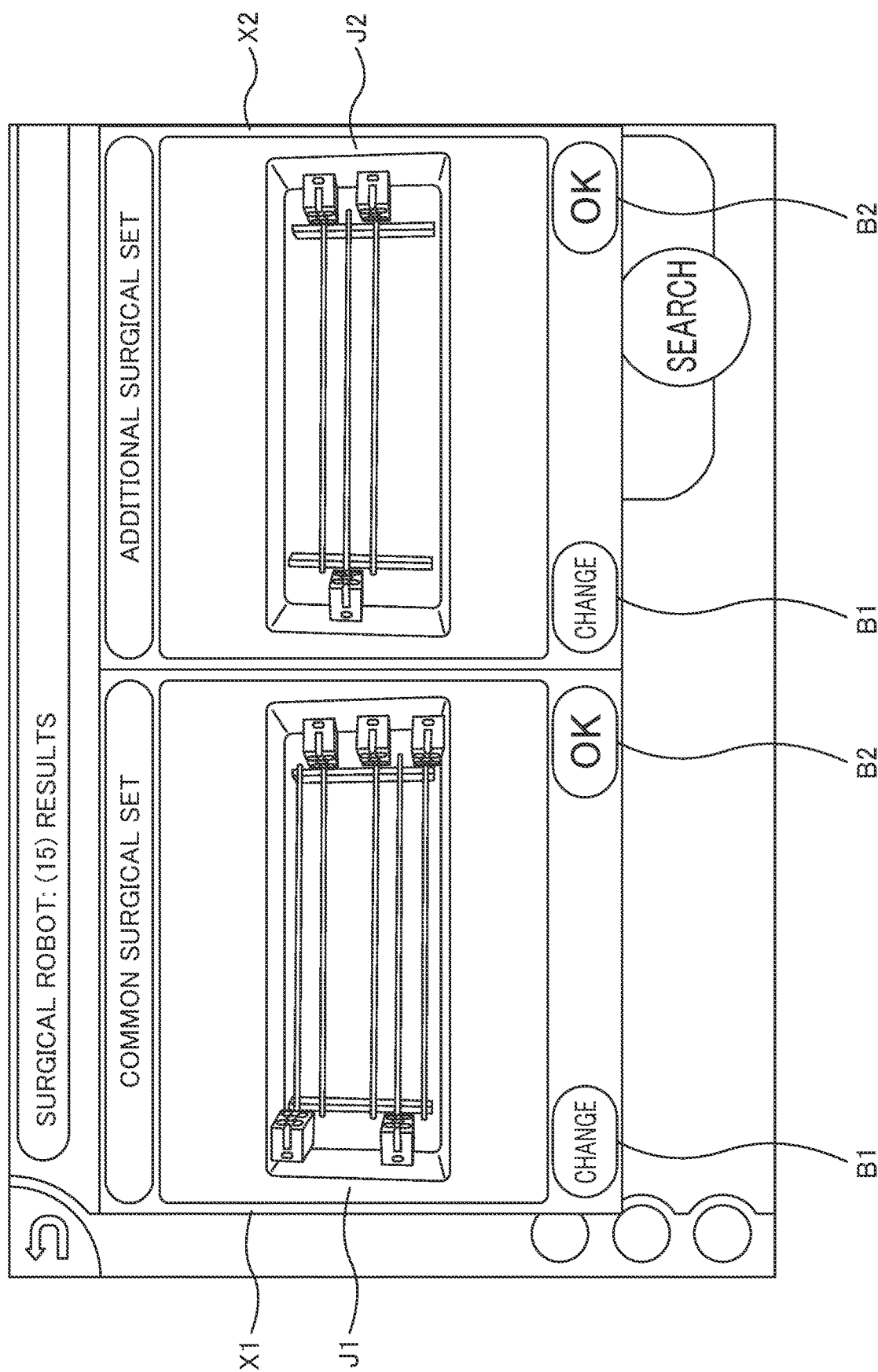
FIG. 5E is a diagram showing a display screen on the terminal of the first preferred embodiment of the present invention.
Figure 5F:
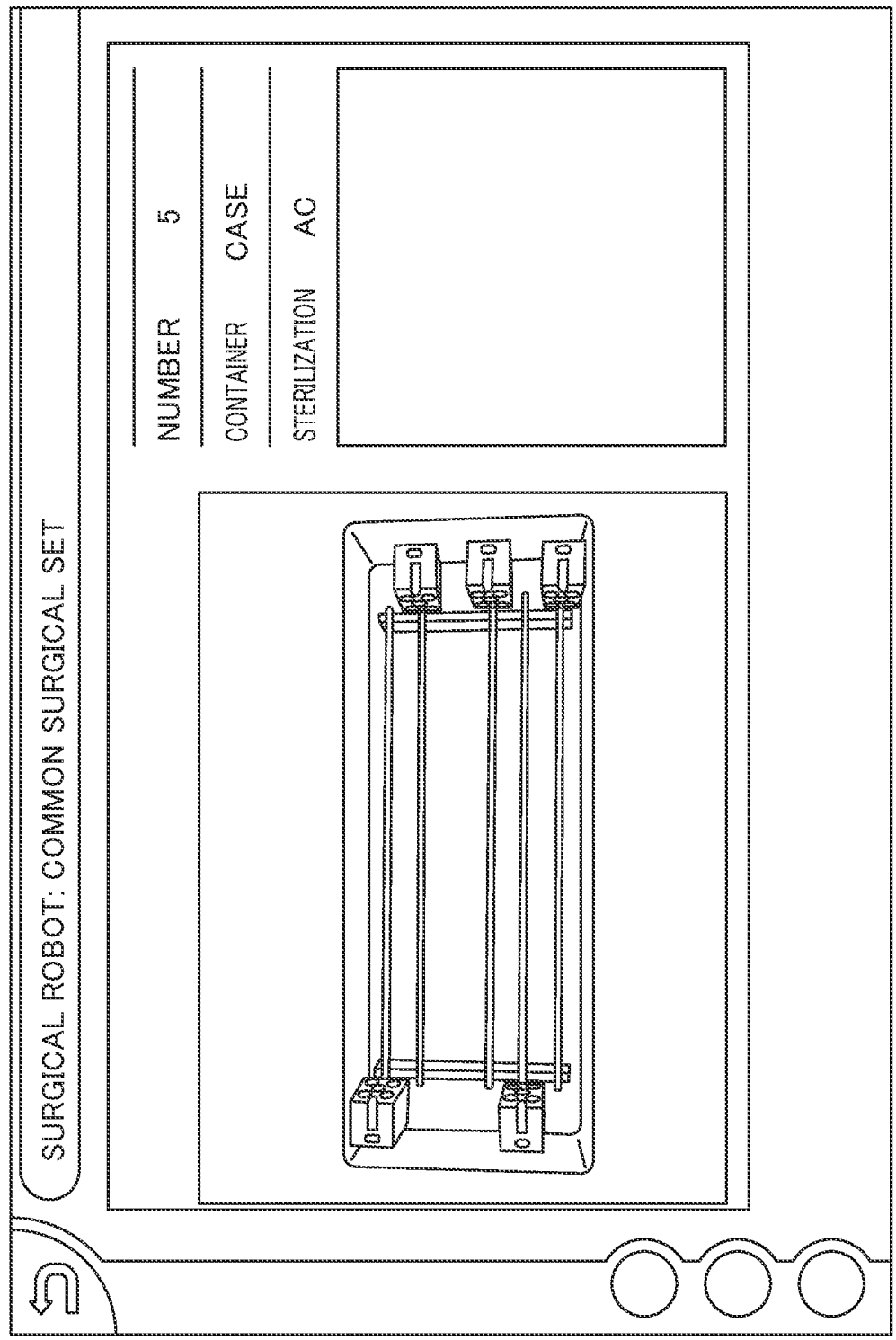
FIG. 5F is a diagram showing a display screen on the terminal of the first preferred embodiment of the present invention.

Furthermore, on the instrument display screen shown in FIG. 5E, when the operator chooses the OK button B2 on the first display portion X1, the display controller 300 is also capable of causing the display 40 to display only the image J1 of the selected first display portion X1 (the entire image J1 is to be enlarged and displayed) (see FIG. 5F). At this time, the display controller 300 is also capable of allowing various kinds of information (e.g., the number, containers, and methods of sterilization) to be displayed associated with the image J1 along with the image (see FIG. 5F).

As can be seen from the above, with the medical instrument displays (the terminals P1 to P3) according to this preferred embodiment, images of a plurality of medical instruments can be displayed in good order. Accordingly, the operator can perform checking operations for medical instruments close at hand while referring to the images, so that it is possible to prevent errors such as confusion of instrument choice or the use of a wrong procedure. Furthermore, by allowing thumbnail images to be displayed, the operator can select any images. Moreover, since only one image can be caused to be displayed after two or more images have been made to be displayed, it is easier for the operator to perform checking operations.

It should be noted that, in the above example, an image selected from the thumbnail images is displayed as the second medical instrument image, but it is not limited thereto. For example, it is possible to allow an image similar to the first medical instrument image to be displayed as the second medical instrument image.

In this case, the image storage 100 allows the image data of a medical instrument to be stored with association to image data of a similar medical instrument. FIG. 6 shows an example of data stored in the image storage 100. In this example, each image data is associated with an image ID (similar image ID) representing an image data of a similar medical instrument.

In addition, the display controller 300 causes the second medical instrument image to be displayed based on the image data of the similar medical instrument associated with the first medical instrument image. For example, when an image based on the image data J1 is displayed, the display controller 300 can automatically cause the second medical instrument image (the image J2) to be displayed on the second display portion X2 based on the image data J2 associated with the image data J1.

Furthermore, two or more image data may be associated with a single image data (see the image data J2 in FIG. 6). In this case, the display controller 300 can provide two or more display portions (a third display portion, a fourth display portion, . . . ) on the display 40 and cause all images to be displayed at the same time. Alternatively, the display controller 300 may also cause only one image among a plurality of images to be displayed on the second display portion X2 and switch images successively according to an instruction input (such as a touch on the display screen) from an operator. Alternatively, thumbnail images (images different from the aforementioned thumbnail images of medical instruments) based on similar image data may be caused to be displayed and an image selected by an operator may be caused to be displayed on the second display portion X2. Furthermore, each of the similar image data is related to frequencies of actual errors beforehand. The display controller 300 may identify the image data for which errors have occurred most frequently among the plurality of similar image data and cause an image based on the image data to be displayed preferentially.

Second Preferred Embodiment

Figure 7A:
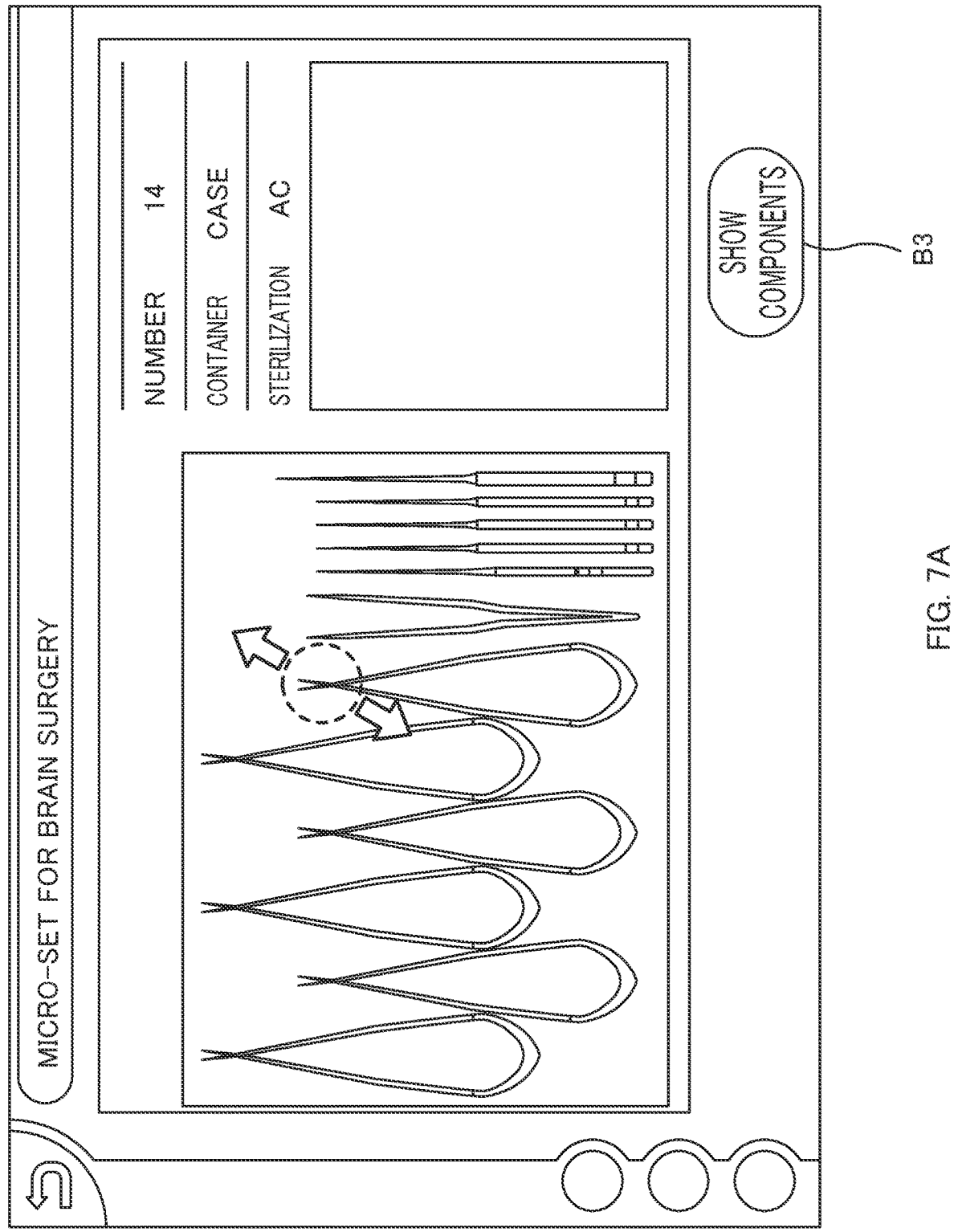
FIG. 7A is a diagram showing a display screen on a terminal of a second preferred embodiment of the present invention.

Referring to FIGS. 7A to 8, an operation assistance system 1 according to a second preferred embodiment of the present invention is described.

When comparing a medical instrument close at hand with images of medical instruments, particular attention should be paid for details such as the shapes of tips of the instruments included in the set. In this preferred embodiment, a configuration to enlarge and display a portion of a medical instrument in such cases is described. A detailed description of a configuration similar to the one in the first preferred embodiment is omitted.

The display controller 300 according to this preferred embodiment causes a designated area to be enlarged and displayed, the designated area being in the first medical instrument image or the second medical instrument image that has been displayed.

The designation of the area in the image is performed by an operator via the operator 50. For example, the operator touches the image displayed on the display 40 at a position where he wants to enlarge and spread fingers. The display controller 300 performs operations to identify coordinates at a touched position and enlarge the displayed image with the coordinates centered. If the operator pinches his fingers, the display controller 300 is able to perform operations to cause the image smaller. Operations to enlarge and reduce an image by spreading and pinching, respectively, can be performed using a known method.

Figure 7B:
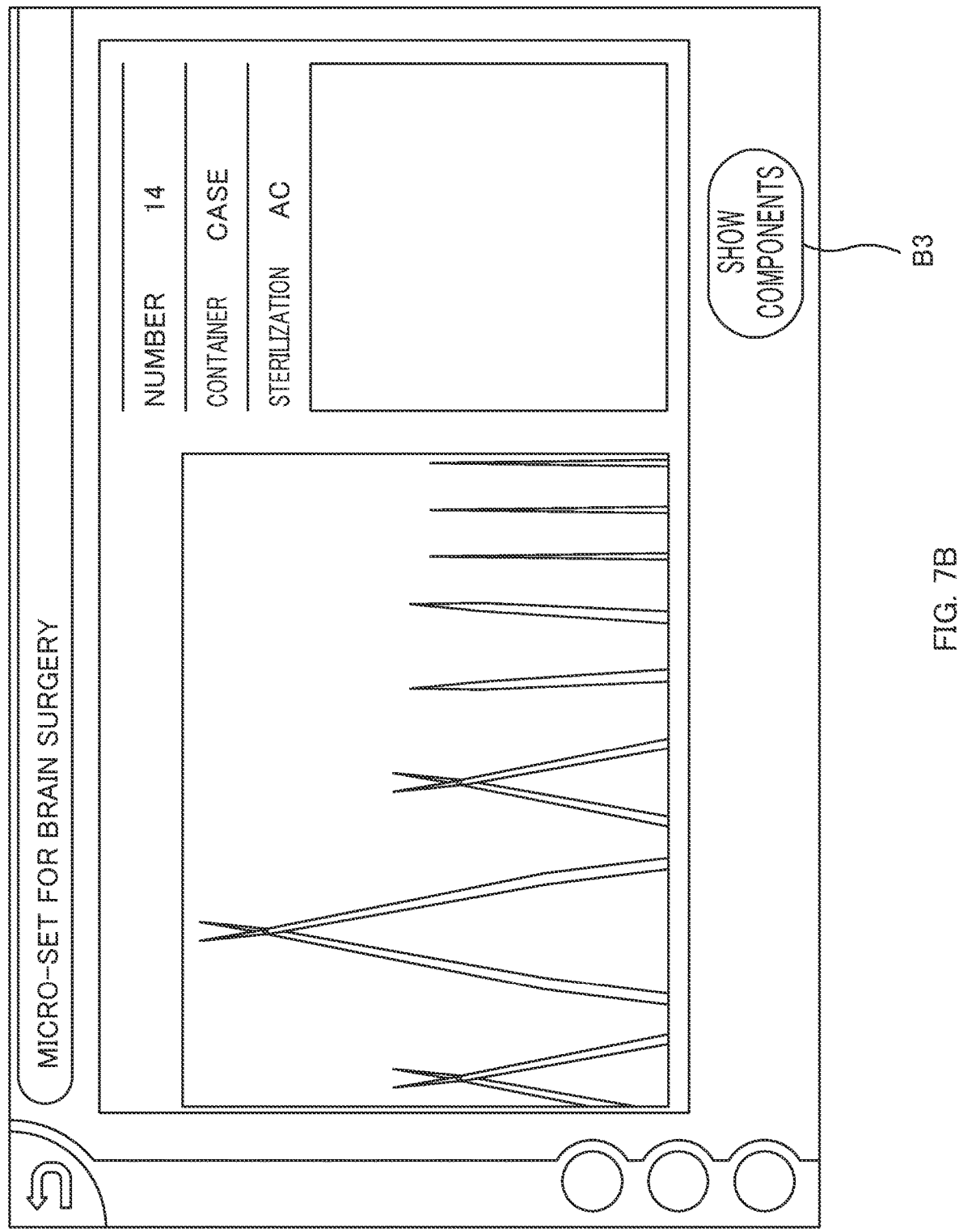
FIG. 7B is a diagram showing a display screen on the terminal of the second preferred embodiment of the present invention.

FIGS. 7A and 7B show display screens of the display 40. FIGS. 7A and 7B show display screens produced when one of two images displayed in good order is displayed as in the case of FIG. 5F. In this example, a micro-set for brain surgery that is an example of a medical instrument is displayed.

As is obvious from FIG. 7A, since the micro-set for brain surgery includes many instruments, it is difficult to check details such as the shapes of tips of the instruments. When the operator pinches his fingers on the place where he wants to enlarge (indicated by an arrow in FIG. 7A), the display controller 300 causes an enlarged image of that area to be displayed (see FIG. 7B). It should be noted that, in FIGS. 7A and 7B, a show components button B3 (described in detail in a third preferred embodiment) is displayed.

When two images are displayed as shown in FIG. 5E, the display controller 300 can cause one of the images for which an instruction input has been made to be enlarged and displayed (reduced and displayed). On the other hand, when one of the images is allowed to be enlarged and displayed (reduced and displayed), the display controller 300 can also cause the other image to be enlarged (reduced) and displayed. For example, when the image J1 is enlarged (magnification m) in the example of FIG. 5E, the display controller 300 identifies coordinates in the image J2 that are identical to the coordinates touched in the image J1 and causes the image J2 be enlarged by the same magnification m as the one used for the image J1 with the coordinates centered.

As can be seen from the above, with the medical instrument displays (the terminals P1 to P3) according to this preferred embodiment, it is possible to enlarge and display an area that is required to be focused on. Accordingly, the operator can check details, which contributes to more positive prevention of errors of instrument choice etc.

As an example of enlarging and displaying a portion of an image of a medical instrument, an image data of a medical instrument may be associated with an enlarged image data in which the medical instrument has been partially enlarged and an image based on that image data may be displayed.

The enlarged image data uses a data obtained by photographing an area that should be focused on (e.g., only a tip portion of one instrument included in a set) when, for example, a medical instrument is to be registered. The enlarged image data is stored in the image storage 100 with association to the image data of a medical instrument. FIG. 8 shows an example of data stored in the image storage 100. For example, an image data J30 for a micro-set for brain surgery is associated with enlarged image data EJ1 to EJ14 for areas that should be focused on. It should be noted that at least one enlarged image data will work.

On the instrument display screen, when an operator gives an instruction to allow an enlarged image to be displayed (e.g., when he chooses an enlarge-and-display button displayed on the screen), the display controller 300 causes the display display an image based on an enlarged image data. The enlarged image may be displayed in good order with an image of a medical instrument or be displayed in a separate screen. When there are a plurality of enlarged images, the display controller 300 may cause one of the images of the plurality of enlarged images to be displayed and switch images successively according to an instruction input from the operator (e.g., a touch on the display screen). Alternatively, thumbnail images based on the plurality of enlarged image data (images different from thumbnail images of medical instruments of the first preferred embodiment) may be caused to be displayed, and an enlarged image selected by the operator may be caused to be displayed on the display 40.

As can be seen from the above, with the medical instrument displays (the terminals P1 to P3) according to this preferred embodiment, an enlarged image corresponding to, for example, an area that should be focused on for a certain medical instrument is associated beforehand. By causing the enlarged image to be displayed, the operator can easily grasp the area that should be focused on etc.

Third Preferred Embodiment

Figure 10:
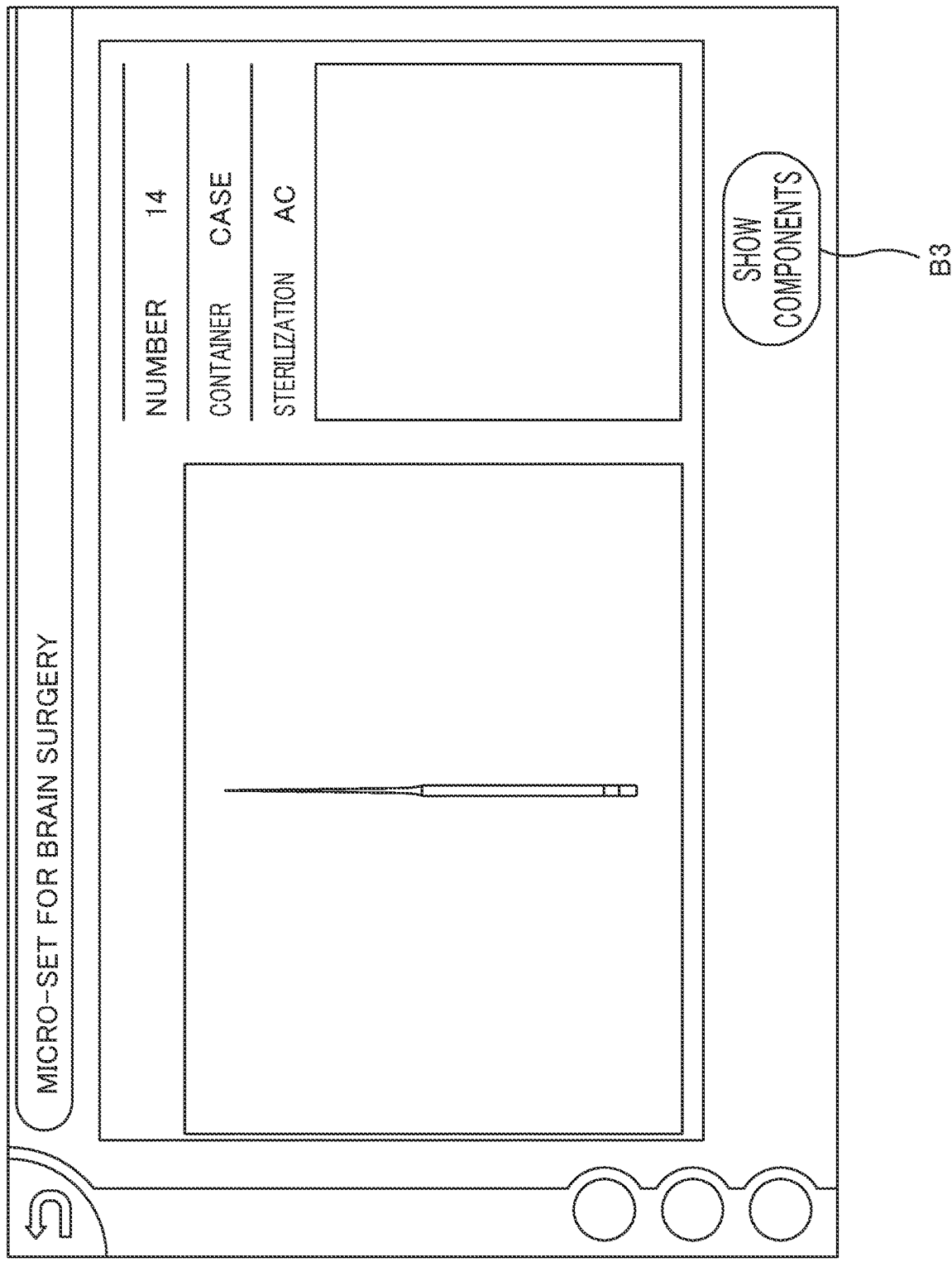
FIG. 10 is a diagram showing a display screen on a terminal of the third preferred embodiment of the present invention.

Referring to FIGS. 9 and 10, the operation assistance system 1 according to a third preferred embodiment of the present invention is described.

Since a set of a medical instrument includes a plurality of instruments, it is sometimes hard to check the individual instruments only by showing an image of the set. This preferred embodiment describes a configuration used to display individual instruments included in a set of a medical instrument. Detailed descriptions of the configuration that is similar to those in, for example, the first preferred embodiment are omitted.

In this preferred embodiment, each image data of a medical instrument (each image data of a set of the medical instrument) is associated with image data of instruments included in the set.

For the image data of each instrument, data obtained by photographing individual instruments when, for example, a set of a medical instrument was registered is used. The image data of each instrument (individual image data) is made to be stored in the image storage 100 with association to the image data of the medical instrument. FIG. 9 shows an example of the data stored in the image storage 100. For example, one of individual image data (IJ1 to IJ14) is associated with a raspatory ε-1, a raspatory ε-2, a pair of forceps ζ-3, ..., and tweezers η-14 included in a micro-set for brain surgery. The individual image data may be associated with only some of the instruments, such as those to which special attention should be paid, among the instruments included in a set.

The display controller 300 causes images based on image data of each of the instruments to be displayed. Specifically, the display controller 300 causes the "show components button B3" to be displayed on the instrument display screen (see FIG. 7A). When an operator chooses this button, the display controller 300 causes the display 40 to display images of the instruments included in the set (see FIG. 10). The images of the instruments may be caused to be displayed in good order with the image of the set or displayed on a separate screen (FIG. 10). Furthermore, when there are a plurality of images of instruments, the display controller 300 causes one of the images of the images of the plurality of instruments to be displayed and the images may be switched successively according to an instruction input (such as a touch on the display screen) from the operator. Alternatively, thumbnail images based on the image data (images different from thumbnail images of medical instruments of the first preferred embodiment) may be caused to be displayed, and an image of the instrument selected by the operator may be caused to be displayed on the display 40.

As can be seen from the above, with the medical instrument displays (the terminals P1 to P3) according to this preferred embodiment, images of the individual instruments included in a set of a medical instrument can be displayed. Accordingly, the operator can check details about the individual instruments, which contributes to more positive prevention of errors of instrument choice etc.

Fourth Preferred Embodiment

Referring to FIG. 11, an operation assistance system according to a fourth preferred embodiment of the present invention is described.

For metal medical instruments, it is possible to imprint a two-dimensional symbol on them by processing. The two-dimensional symbol is an identifier unique to each medical instrument. By reading the two-dimensional symbol using a special-purpose reader, it is possible to identify one of the medical instruments from a plurality of medical instruments. Here, some sets of medical instruments contain instruments on which a symbol can be imprinted and those on which a symbol cannot be imprinted (e.g., instruments made of resin). In this preferred embodiment, described is a configuration with which, when at least one instrument of a set is assigned with an identifier, an image of the set is made easily displayable. Detailed descriptions of the configuration that is similar to those in, for example, the first preferred embodiment are omitted.

The image storage 100 according to this preferred embodiment stores a plurality of image data of a medical instrument corresponding to a set including a plurality of instruments. FIG. 11 shows an example of data stored in the image storage 100. Of the instruments contained in a surgical robot common surgical set, for instruments α and β imprinted with two-dimensional symbols, individual instrument IDs (E1, E2) corresponding to the two-dimensional symbols are stored with association to image data. The identifier need only be assigned to at least one of the instruments contained in a single set.

The data analyzer 200 according to this preferred embodiment searches a plurality of medical images based on the identifier for image data of the medical instrument containing the instrument assigned with the identifier. The data analyzer 200 supplies the searched image data to the display controller 300.

The display controller 300 according to this preferred embodiment causes the display 40 to display an image based on the searched image data.

As a specific example, it is assumed that an instrument close at hand is assigned with a two-dimensional symbol (identifier E-1). An operator reads the two-dimensional symbol using a reader (not shown). The reader may be a dedicated reader or using, for example, an application that has been installed on the terminal. The data analyzer 200 searches the data stored in the image storage 100 based on the identifier E-1 read by the reader to identify a set (surgical robot common surgical set) to which the identifier E-1 has been assigned. The data analyzer 200 supplies the image data J1 for the identified set to the display controller 300. The display controller 300 causes the image of the surgical robot common surgical set be displayed based on the image data J1.

As can be seen from the above, with the medical instrument displays (the terminals P1 to P3) according to this preferred embodiment, based on the identifier assigned to a certain instrument, an image of a set containing that instrument can be caused to be displayed.

While this preferred embodiment has been described taking the two-dimensional symbol as an example, the identifier is not limited thereto. For example, an identifier may be directly put on or printed on an instrument. Alternatively, for medical instruments such as endoscopes, an electromagnetic tag such as RFID may be used as an identifier.

Fifth Preferred Embodiment

The invention according to this preferred embodiment relates to programs, GUI devices, and display methods for displaying a widget representing a process on a screen.

Conventionally, management systems have been used for the purpose of, for example, managing inventory of articles such as medical instruments. For example, in a technique described in JP-A-2005-237586, data such as the number of times each surgical instrument was used, the time at which it was sterilized, a person who sterilized it, a storage location, the time at which storage was started, and a warden are managed in the database using an identification tag assigned to surgical instruments that can be re-used.

Further, for example, in a technique described in JP-A-2008-54732, since information indicating the completion of cleaning and information indicating the cleaning date are recorded in an IC tag for an endoscope after cleaning of that endoscope has been completed, no such information is recorded in an IC tag for an endoscope that has not yet been cleaned. Therefore, before the use of an endoscope, by reading the information stored in the IC tag for the endoscope by an IC tag reader, it is possible to recognize whether the endoscope has already been cleaned or not.

By the way, articles such as medical instruments can exhibit their performance by being properly handled. Therefore, an instruction manual describing accurate handling of articles is required, and users handle the articles while reading the instruction manual. For example, as a handling operation for medical instruments such as surgical instruments, the medical instruments are disassembled, cleaned, assembled after the cleaning, after which the medical instruments are sterilized. At that time, an operator performs operations while checking a way of handling using an instruction manual.

The instruction manuals, however, contain explanations on functions not used in the actual site of use, and the description of the instruction manual is long. On the other hand, the content of the instruction manual may be insufficient for the explanation. Therefore, for the site of use where articles such as medical instruments are used, new descriptions may be prepared based on the instruction manual. In preparing descriptions, a word processor function of a computer or the like may be used, but word processor functions of computers are for general purposes and are not directed to prepare descriptions of articles such as medical instruments. In particular, a creator is required to get used to a user interface of the computer, and fails to prepare descriptions easily.

Therefore, the invention according to this preferred embodiment has been made in view of the above circumstances, and the problem to be solved by the invention according to this preferred embodiment is to allow even users unfamiliar with user interfaces to intuitively enter data continuously.

According to the present preferred embodiment, a non-transitory computer-readable medium includes a program for causing a computer, the computer operating a screen of a display according to an operation of an input and being capable of reading a storage in which a plurality of image data showing a medical instrument are stored, to execute: a first display step of causing the display to display the screen such that a first unregistered widget is displayed on the screen, the first unregistered widget representing a main process that is a handling operation for a medical instrument and having no image shown therein; after the first display step, a selection step of selecting one or more image data from the plurality of image data according to an operation of the input; and after the selection step, a second display step of causing the display to display the screen so as to change and display the first unregistered widget in the screen into a registered widget, the registered widget including an image of the image data selected in the selection step shown therein and representing the main process; displaying a second unregistered widget on the screen at a position adjacent to the registered widget in either one of vertical and lateral directions of the screen, the second unregistered widget representing the main process and having no image shown therein; and displaying a third unregistered widget on the screen at a position adjacent to the registered widget in the other of the vertical and lateral directions of the screen, the third unregistered widget representing a sub process of the main process and having no image shown therein.

Other features of the invention according to this preferred embodiment are disclosed in the descriptions of the specification and the drawings that follow.

In the invention according to this preferred embodiment, it is possible for even users unfamiliar with user interfaces to intuitively enter data continuously.

In the descriptions of the specification and the drawings that follow, at least the following features are disclosed.

A non-transitory computer-readable program for causing a computer, the computer operating a screen of a display according to an operation of an input and being capable of reading a storage in which a plurality of image data showing a medical instrument are stored, to execute: a first display step of causing the display to display the screen such that a first unregistered widget is displayed on the screen, the first unregistered widget representing a main process that is a handling operation for a medical instrument and having no image shown therein; after the first display step, a selection step of selecting one or more image data from the plurality of image data according to an operation of the input; and after the selection step, a second display step of causing the display to display the screen so as to change and display the first unregistered widget in the screen into a registered widget, the registered widget having an image of the image data selected in the selection step shown therein and representing the main process; displaying a second unregistered widget on the screen at a position adjacent to the registered widget in either one of vertical and lateral directions of the screen, the second unregistered widget representing the main process and having no image shown therein; and displaying a third unregistered widget on the screen at a position adjacent to the registered widget in the other of the vertical and lateral directions of the screen, the third unregistered widget representing a sub process of the main process and having no image shown therein is disclosed.

A GUI device including an input, a display, a storage in which a plurality of image data showing a medical instrument are stored, and a computer that operates a screen of the display according to an operation of the input and is capable of reading the storage, wherein the computer executes: a first display step of causing the display to display the screen such that a first unregistered widget is displayed on the screen, the first unregistered widget representing a main process that is a handling operation for a medical instrument and having no image shown therein; after the first display step, a selection step of selecting one or more image data from the plurality of image data according to an operation of the input; and after the selection step, a second display step of causing the display to display the screen so as to change and display the first unregistered widget in the screen into a registered widget, the registered widget having an image of the image data selected in the selection step shown therein and representing the main process; displaying a second unregistered widget on the screen at a position adjacent to the registered widget in either one of vertical and lateral directions of the screen, the second unregistered widget representing the main process and having no image shown therein; and displaying a third unregistered widget on the screen at a position adjacent to the registered widget in the other of the vertical and lateral directions of the screen, the third unregistered widget representing a sub process of the main process and having no image shown therein.

A display method executed by a computer operating a screen of a display according to an operation of an input and being capable of reading a storage in which a plurality of image data showing a medical instrument are stored, the method including: a first display step of causing the display to display the screen such that a first unregistered widget is displayed on the screen, the first unregistered widget representing a main process that is a handling operation for a medical instrument and having no image shown therein; after the first display step, a selection step of selecting one or more image data from the plurality of image data according to an operation of the input; and after the selection step, a second display step of causing the display to display the screen so as to change and display the first unregistered widget in the screen into a registered widget, the registered widget having an image of the image data selected in the selection step shown therein and representing the main process; displaying a second unregistered widget on the screen at a position adjacent to the registered widget in either one of vertical and lateral directions of the screen, the second unregistered widget representing the main process and having no image shown therein; and displaying a third unregistered widget on the screen at a position adjacent to the registered widget in the other of the vertical and lateral directions of the screen, the third unregistered widget representing a sub process of the main process and having no image shown therein.

With the non-transitory computer-readable media including programs, GUI devices, and display methods mentioned above, when a user operates an input, an image data showing a medical instrument is selected. Then, on the screen of the display, the first unregistered widget representing the main process is changed to the registered widget having an image of that image data shown therein. The second unregistered widget representing the main process is displayed at a position adjacent to the registered widget in either one of the vertical and lateral directions of the screen, and the third unregistered widget representing the sub process of the main process is displayed at a position adjacent to the registered widget in one of the vertical and lateral directions of the screen. Accordingly, it is possible to prod a user to select a new image using the second and third unregistered widgets, and the user can easily perform a subsequent entry operation; therefore, the user can perform entry operations continuously.

Furthermore, it is possible to intuitively recognize the order of main processes and the order of sub processes from the arrangement of the widgets.

Preferably, by the program, the computer further executes: a second selection step of selecting one or more image data from the plurality of image data according to an operation of the input after the second display step; and after the second selection step, a third display step of causing the display to display the screen so as to change and display the third unregistered widget in the screen into a second registered widget, the second registered widget having an image of the image data selected in the second selection step shown therein and representing the sub process; and displaying a fourth unregistered widget on the screen at a position adjacent to the second registered widget in the other direction of the screen, the fourth unregistered widget representing a sub process of the main process and having no image shown therein.

According to the above, when a user further operates the input, an image data showing a medical instrument is selected. Then, on the screen of the display, the third unregistered widget representing the sub process is changed into the second registered widget having an image of the image data shown therein. The fourth unregistered widget representing the sub process is displayed at a position adjacent to the second registered widget in the other direction of the vertical and lateral directions of the screen. Accordingly, it is possible to prod a user to select a new image using the fourth unregistered widget, and the user can easily perform a subsequent entry operation; therefore, the user can perform entry operations continuously.

Referring to the drawings, a fifth preferred embodiment of the present invention is described below. The preferred embodiment described below includes various limitations that are technically preferable for the purpose of implementing the present invention; therefore, the scope of the present invention is not limited to the following preferred embodiment and illustrated examples.

Figure 12:
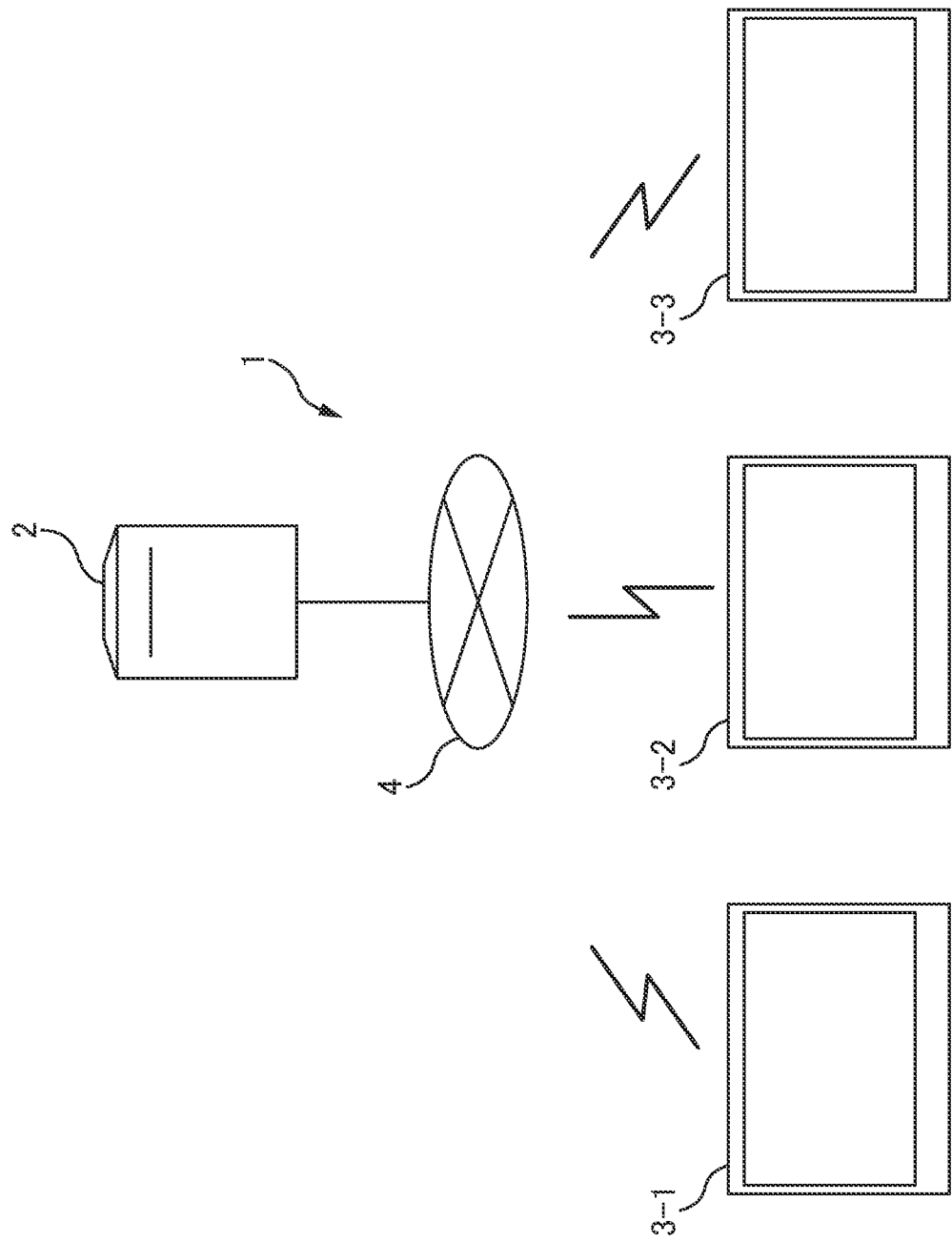
FIG. 12 is a diagram showing a configuration of a network system.

As shown in FIG. 12, a network system (operation flow creation assistance system) 1 includes a server 2, a plurality of terminals 3 (in this example, three terminals 3-1, 3-2, and 3-3) and a communication network 4. The terminals 3-1 to 3-3 can communicate with the server 2 via the network 4. Each of the terminals 31 to 3-3 is a desktop type, laptop type or tablet type computer system. Each of the terminals 3-1 to 3-3 may be a portable computer system or a computer system on a desk. The server 2 is a tower type, desktop type, rack mount type or blade type computer system. The network 4 is a dedicated line network running in a hospital facility, for example, a LAN (Local Area Network) using cables or radio frequencies.

This system 1 is a device that assists creation of contents (hereinafter, referred to as an operation flow content) for expressing a flow of a medical instrument handling operation in order to visually present, to an operator, details of the medical instrument handling operation related to handling of medical instruments. Creation of operation flow contents will be described in detail later and the medical instrument handling operation as well as a way of use of the system 1 at that time are described first below.

The medical instrument handling operation refers to an operation performed for surgeries in which medical instruments are used. Medical instruments refer to instruments such as endoscopes, ultrasonic probes, pairs of forceps, pairs of scissors, scalpels, scalpel handles, cannulas, tweezers, retractors, scales, Sondes, elevators, raspas, suction tubes, rib spreaders, rib contractors, needle holders, syringes, metal balls, kidney dishes, cups, pins, mirrors, files, opening devices, Klemmes, handpieces, Elevatoriums, chisels, curettes, raspatories, mirrors, suture needles, rongeurs, water receivers, needles, spatulas, bougies, vent tubes, bone impactors, rongeurs, needle-nose pliers, hammers, goniometers, perforators, droppers, metal swabs, enemas, syringes and the like. Combinations of a plurality of instruments (such as surgical kits including pairs of forceps, scalpels, pairs of scissors) are also included in medical instruments.

Figure 13:
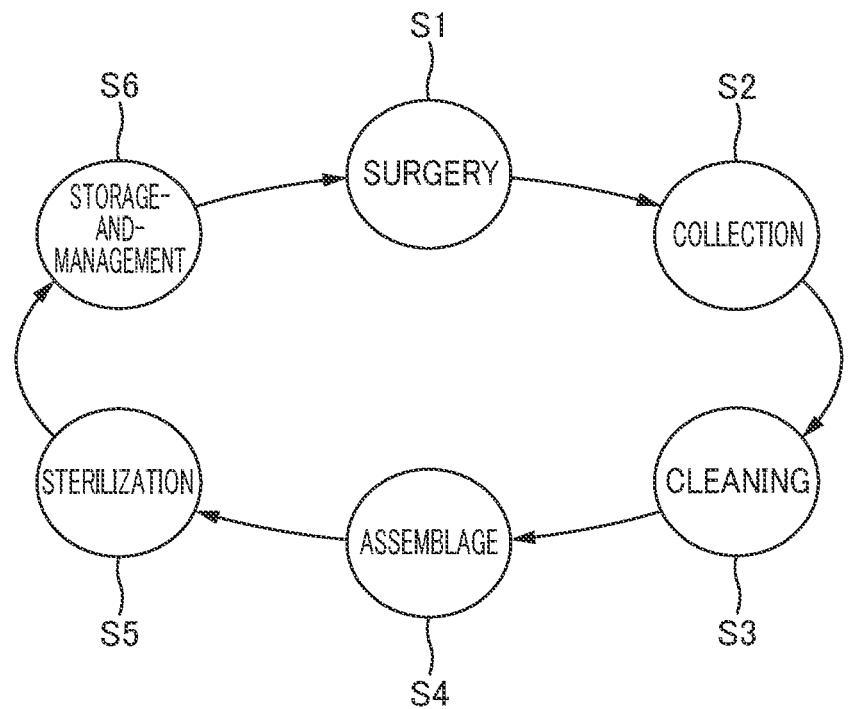
FIG. 13 is a chart showing an operation cycle in which medical instruments are handled.

FIG. 13 is a chart showing an operation cycle in which medical instruments are handled. As shown in FIG. 13, examples of the medical instrument handling operation include a collection operation S2, a cleaning operation S3, an assemblage operation S4, a sterilization operation S5, and a storage-and-management operation S6. Medical instruments are handled in any of the operations S2 to S6.

Specifically, when a physician used a medical instrument during a surgery S1, the medical instrument is collected after the surgery S1 (the collection operation S2). Then, the collected medical instrument is disassembled and cleaned using a cleaning device (the cleaning operation S3). Then, the cleaned medical instrument is assembled (the assemblage operation S4). Then, the assembled medical instrument is subjected to a sterilization (the sterilization operation S5). Then, the sterilized medical instrument is stored for surgery (the storage-and-management operation S6). The stored medical instrument will be used for a surgery S1 again.

The system 1 is used for the medical instrument handling operation such as the collection operation S2, the cleaning operation S3, the assemblage operation S4, the sterilization operation S5, and the storage-and-management operation S6.

Although details are described later, an operation flow content is created by user's operating the terminals 3-1 to 3-3 or the server 2 of the system 1 and the created operation flow content is recorded in the storage of the server 2. The operation flow content recorded in the storage of the server 2 is also synchronized with (recorded on) the storages of the terminals 3-1 to 3-3. Subsequently, by the operator's operating the terminal 3-1 in performing the medical instrument handling operation, a flow and details of the medical instrument handling operation are presented to the terminal 3-1; therefore, the operator can proceed the medical instrument handling operation while looking at the terminal 3-1 to check the details of the operation. Here, the medical instrument handling operation includes one or more upper-level processes at the uppermost level. Each upper-level process includes one or more main processes at a middle-upper level. Each main process includes one or more sub processes at the lowermost level. In other words, each main process represents detailed operations required for completing the operation of the upper-level process having that main process as a component. Detailed operations of the main process are those obtained by segmenting operations of the upper-level process. Each sub process represents detailed operations required for completing the operation of the main process having that sub process as a component. Detailed operations of the sub process are those obtained by segmenting operations of the main process.

Figure 14:
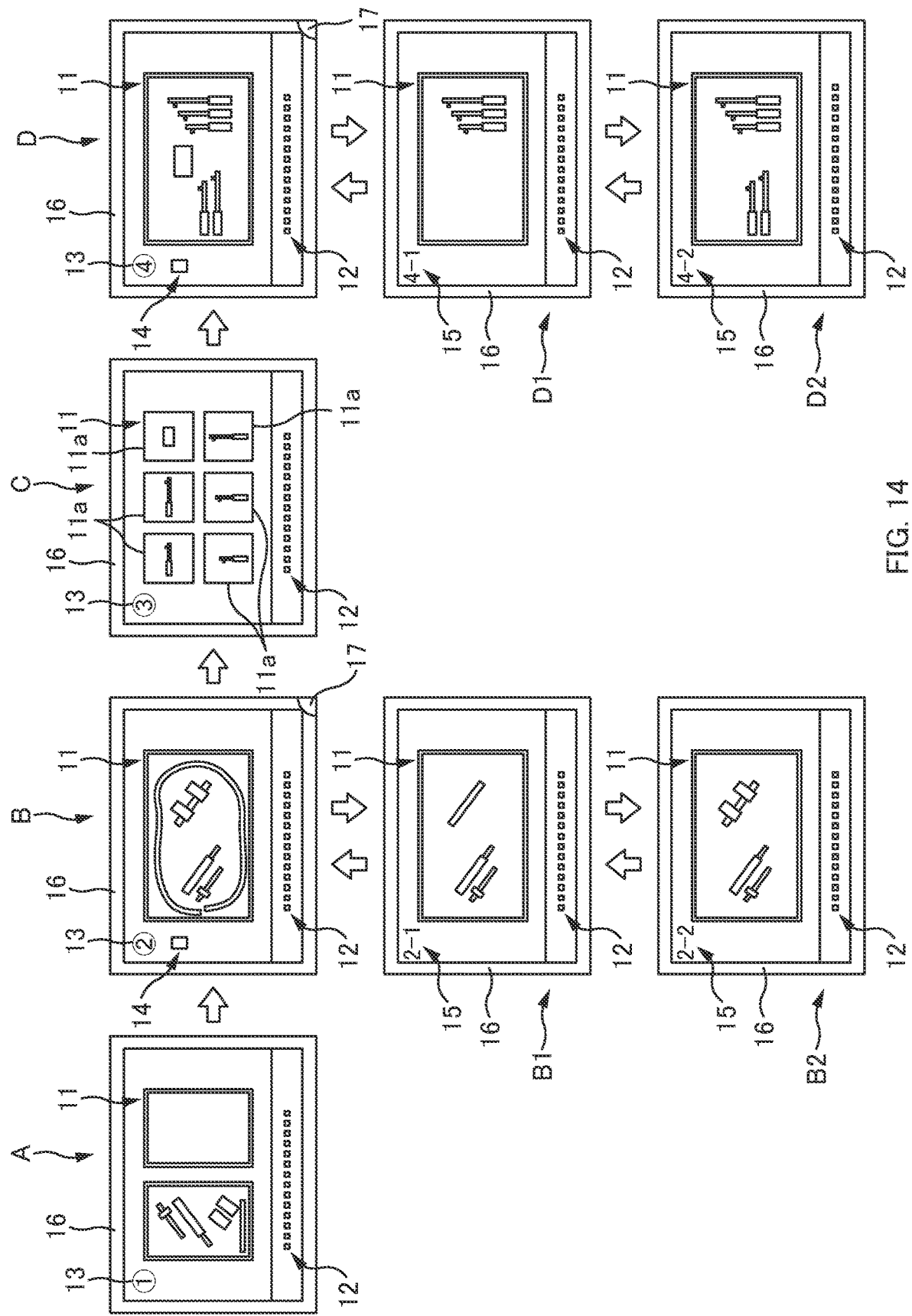
FIG. 14 is an explanatory diagram of a screen transition.

Referring to FIG. 14, what is displayed on the terminal 3-1 is described. Here, FIG. 14 is a diagram showing transitions of the screen displayed on the display of the terminal 3-1 according to an operation flow content.

When an operator is going to perform a certain upper-level process during a medical instrument handling operation, he selects a certain option (the certain option corresponds to a certain upper-level process) from a plurality of options (options and the upper-level processes correspond to each other one by one) by operating the terminal 3-1 while looking at a process selection screen (option list screen) displayed on the terminal 3-1. Here, the operation is displayed in the form of, for example, a widget (on the widget, an image designated by an image designation data of an upper-level process data 45 described later is displayed), an icon (a thumbnail of an image designated by an image designation data of an upper-level process data 45 described later), a button, or a radio button, etc.

Thereafter, when the operator operates the terminal 3-1 (for example, a flick operation, a swipe operation, a tap operation, a multi-tap operation, a scroll operation or a drag operation) as the operation proceeds in a certain upper-level process, the view of the display of the terminal 3-1 changes from a screen A, to a screen B, a screen C, and then a screen D in this order. The screens A to D are associated with main processes of a certain upper-level process in the medical instrument handling operation. More specifically, they are for displaying details of the operation in each main process and the state of the medical instrument(s) for this operation. Furthermore, on the screens A to D, information (for example, a name of an operation of an upper-level process and an outline of an operation of an upper-level process) for specifying the upper-level process including the processes associated with the screens A to D is displayed. The number of the main processes of each upper-level process in the medical instrument handling operation is not limited to four, and the number of the screens related to the main processes is equal to the number of the main processes.

Further, when the operator operates the terminal 3-1 while the screen B is being displayed on the display of the terminal 3-1, the view of the display of the terminal 3-1 changes from the screen B to a screen B1. Moreover, by the operator's operating the terminal 3-1, the view of the display of the terminal 3-1 changes from the screen B1 to a screen B2, from the screen B2 to the screen B1, from the screen B1 to the screen B. The screens B1 and B2 are associated with sub processes (detailed processes) of the main process associated with the screen B. More specifically, they are for displaying details of the operation in each sub process and the state of the medical instrument(s) for this operation.

Similarly, when the screen D is displayed on the display of the terminal 3-1, transitions occur from the screen D to a screen D1 and from the screen D1 to a screen D2 by the operation of the terminal 3-1 by the operator. The screens D1 and D2 are associated with sub processes of the main process related to the screen D. More specifically, they are for displaying details of the operation in each sub process and the state of the medical instrument(s) for this operation. It should be noted that the number of sub processes of each main process associated with the screens B and D is not limited to two, and the number of screens associated with the sub processes is equal to the number of sub processes.

The main process is classified as different types: a normal operation process, a quality important operation process, or a count operation process. In the screens A to D, one can understand which type each main process belongs to. For example, a process classification display 16 is displayed in the periphery of each of the screens A to D and the color of the process classification display 16 indicates the type of the main process. For example, because the main process associated with the screen A is the normal operation process, the process classification display 16 of the screen A is drawn in blue. Because the main processes associated with the screens B and D are the quality important operation process, the process classification display 16 of the screen C is drawn in red. Because the main process associated with the screen C is the count operation process, the process classification display 16 of the screen C is drawn in red. On the other hand, the kind of the sub processes is only the normal operation process. However, it is possible to visually determine which of the main process and the sub process the displayed screen is associated with, because the color of the process classification display 16 used in the case of the sub process (e.g., green) and the color of the process classification display 16 used when the main process is the normal operation process (e.g., blue) are different from each other.

An instrument display 11 and an operation detail display 12 are displayed on any of the screens A to D, B1, B2, D1, and D2. On the operation detail display 12, details of the operation of that process are displayed with a text. On the instrument display 11, the state of the medical instrument(s) for the operation of that process is displayed with an image.

On the screens A to D, an order display 13 indicating the page number or the main process order is displayed. The page number represents the display order of the screens A to D in ascending order with respect to the screen A as a reference. The main process order represents the order of the main processes of each of the screens A to D in ascending order with respect to the main process related to the screen A. The number of pages and the main process order may be represented by numerals (text), or may be represented by, for example, a symbol, a mark, a pattern, or an indicator.

On the screen B, a tag display 14 indicating a tag is displayed. The tag (for example, a text "detail" or "CHECK") displayed on the tag display 14 indicates that the main process associated with the screen B has a sub process. Since the main process associated with the screen C has a sub process, a tag display 14 is also displayed on the screen D. Since the main processes associated with the screens A and C have no sub process, no tag display is displayed on the screens A and C.

On the screens B1, B2, D1, and D2, an order display indicating a sub process order is displayed. The sub process order represents the order of sub processes of the main process in ascending order. The sub process order may be represented by a number (text), or may be represented by, for example, a symbol, a mark, a pattern, or an indicator.

When the screen A is being displayed, the operator can check the details of the operation of the process by viewing the operation detail display 12 of the screen A. In addition, by viewing the instrument display 11 of the screen A, he can compare the actual medical instrument handled and images of medical instruments on the instrument display 11, whereby it is possible to check whether the operation of that process has proceeded accurately. In other words, if the state of the actual medical instrument handled is about the same as the medical instrument image on the instrument display 11, it can be recognized that the operation in that process is accurate, and if the state of the actual medical instrument is different from the medical instrument image on the instrument display 11, it can be recognized that the operation in that process is inaccurate.

By the operator's operating the terminal 3-1 as the medical instrument handling operation proceeds, the view of the display of the terminal 3-1 changes from the screen A to the screen B, the screen C, and then to the screen D in this order. Therefore, the operator can visually recognize details of the operation and the accuracy of the operation in each process.

The main processes associated with the screens B and D are quality important operation processes. The operations to change the screens B and D of the quality important operation process to the subsequent screen is different from the operations for changing the screens of the normal operation process and the count operation process to their subsequent screens. That is, a confirmation button 17 is displayed at the lower right of the screens B and D, and the screen turns to a next screen when an operation (for example, single click, double click, tap, double tap, and long press) of selecting and determining the confirmation button 17 is performed. If this operation of selecting and determining the confirmation button 17 is not performed, no next screen is displayed. Thus, the quality of the quality important operation is guaranteed by making an operator do careful operations and checking. When an operation of selecting and determining the confirmation button 17 is performed after the display of the screen D, the screen of the terminal 3-1 returns to the process selection screen or turns to a screen related to a subsequent upper-level process. The screen transition of the terminal 3-1 is performed in a similar manner when the operator operates the terminal 3-1 as the next upper-level process proceeds.

The main process associated with the screen C is the count operation process, but the operation to change the screen C to a next screen of the count operation process is different from an operations for changing the screens of the normal operation process and the quality important operation process to their subsequent screens. Specifically, a plurality of widgets 11a are displayed on the instrument display 11 of the screen C and images of components of a medical instrument are displayed on these widgets 11a. The operator operates the terminal 3-1 while comparing components of an actual medical instrument with the widgets 11a. Specifically, if the components displayed on the widgets 11a are included in the actual medical instrument, the operator selects that widget 11a by operating the terminal 3-1. In this way, after all the widgets 11a are selected, the screen C is turned to a next screen. Accordingly, with the screen C is displayed, the screen C does not turn to any subsequent screens unless operations of checking the presence or absence of the actual components of the medical instrument and operations of counting these components has been completed. This forces the operator to perform such operations.

It should be noted that when the operator performs another upper-level process in the medical instrument handling operation, the screen of the terminal 3-1 will shift in a similar manner by operating the terminal 3-1 as the operation of the upper-level process proceeds.

A user creates, by using the terminals 3-1 to 3-3 or the server 2 of the system 1, an operation flow content for achieving screen transitions as mentioned above. The terminal 3-1 is described in detail below under the assumption that an operation flow content is created using the terminal 3-1.

Figure 15:
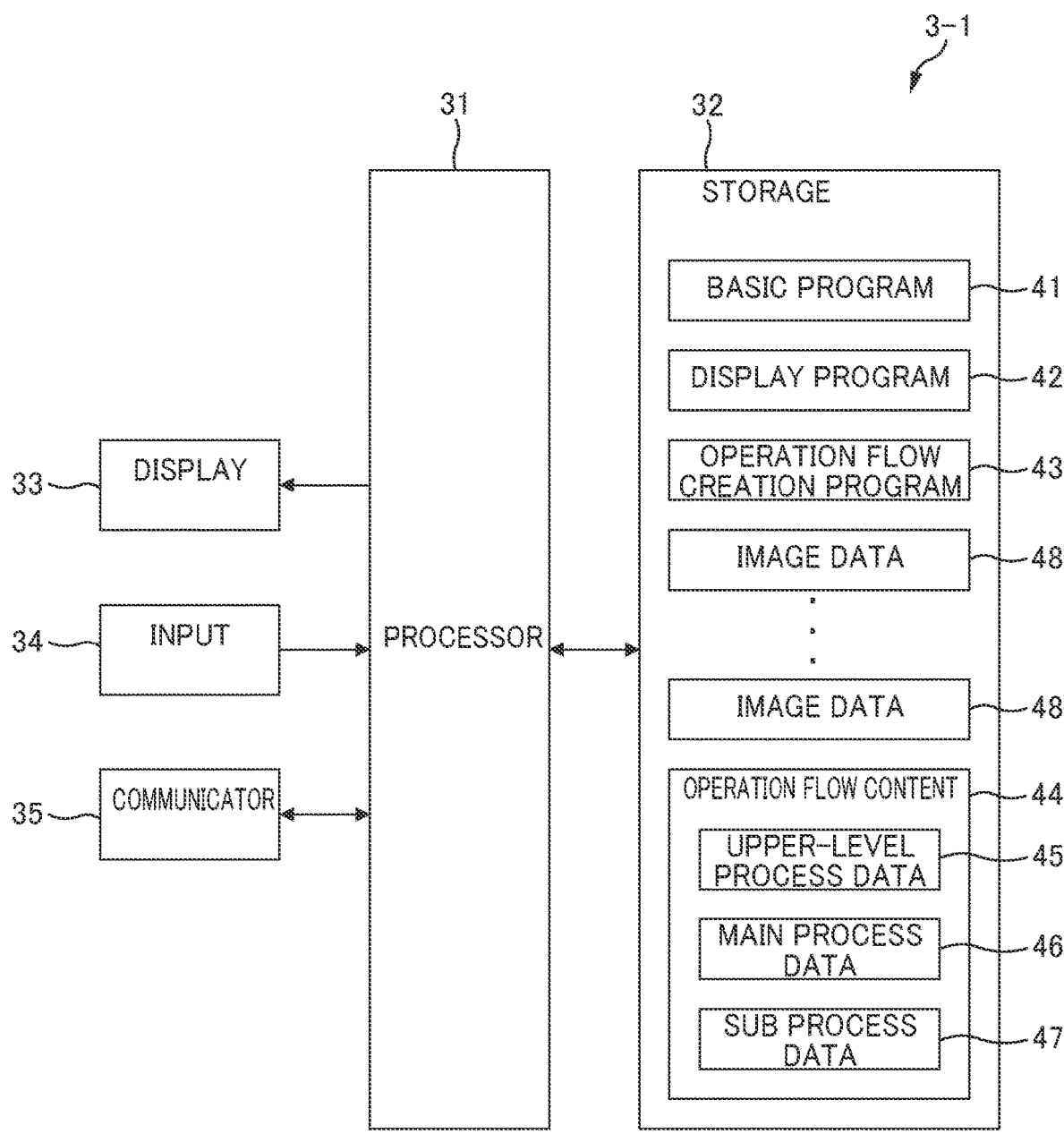
FIG. 15 is a block diagram of a terminal as a GUI device.

The terminal 3-1 is an assistance device that assists creation of operation flow contents and a GUI (Graphical User Interface) device that controls display of widgets. As shown in FIG. 15, this terminal 3-1 includes, as hardware, a processor 31, a storage 32, a display 33, an input 34, and a communicator 35.

The processor 31 is a computer including a CPU, a GPU, a ROM, a RAM, a bus, a hardware interface, and the like. The storage 32 is a storage including a semiconductor memory, a hard disk drive, and the like that is readable and writable by the processor 31. The display 33 is a display that performs screen display. The input 34 is an input such as a touch panel, a switch, a keyboard, and a pointing device. The communicator 35 is a network adapter (for example, a network interface card, a wireless LAN slave).

It should be noted that each of the terminals 3-2 and 3-3 and the server 2 also includes a processor, a storage, a display, an input, and a communicator as in the case of the terminal 3-1.

In the storage 32, a plurality of image data 48 that can be read by the processor 31 are recorded. The image data are images having a medical instrument shown therein to indicate a state of the medical instrument due to operations in each process. The image data 48 have their unique data (e.g., a file name or an identifier) and each image data 48 can be distinguished from other image data 48 according to the unique data.

The image data 48 is recorded in advance in the storage 32 for each type, state, component, combination, etc. of a medical instrument. Every time a medical instrument is introduced (transferred, purchased, stocked, lent) to a hospital, image data obtained by photographing the medical instrument and its components using an electronic camera are stored in a database of a storage of the server 2 and the image data thereof are also synchronized with (recorded on) the storage 32 as the image data 48.

In the storage 32, an operation flow content 44 is recorded. The operation flow content 44 is created in a manner described later and is used to change screens as a medical instrument handling operation proceeds, as mentioned above. The operation flow content 44 includes an upper-level process data 45 for each upper-level process, a main process data 46 for each main process, and a sub process data 47 for each sub process.

FIG. 16 is a diagram showing a data configuration of the upper-level process data 45. The upper-level process data includes an upper-level process order data, an operation name data, and an image designation data. The upper-level process order data represents the order of the upper-level process. The operation name data is a text data representing an operation name that briefly and simply shows details of the operation of the upper-level process. The image designation data is for designating a particular image data 48 from the plurality of image data 48. More specifically, it is a unique data (e.g., a file name or an identifier) of a particular image data 48. As described above, in the process selection screen, images designated by the image designation data of the upper-level process data 45 is displayed.

FIG. 17 is a diagram showing a data configuration of the main process data 46. The main process data 46 includes an upper-level process order data, a main process order data, an operation detail data, a classification data, an image designation data, and a sub process presence/absence data.

The upper-level process order data represents the order of the upper-level process to which the main process belongs. The main process data 46 and the upper-level process data 45 having the same value of the upper-level process order data are associated with each other.

The main process order data represents the order of the main process. In displaying each of the screens A to D, the main process order data is referred to by the processor 31 and a view of the order display 13 is determined by the processor 31 according to the main process order data and the order of displaying the screens A to D is determined by the processor 31.

The operation detail data is a text data representing details of the operation of the main process. In displaying each of the screens A to D, the operation detail data is referred to by the processor 31 and a view of the operation detail display 12 is determined by the processor 31 according to the operation detail data.

The classification data represents a type of the main process. Values of the classification data are a "normal operation," a "quality important operation," and a "count operation." Which one of the normal operation process, the quality important operation process, and the count operation process the main process is classified can be understood based on the classification data. In displaying each of the screens A to D, the classification data is referred to by the processor 31 and the color of the process classification display 16 is determined by the processor 31 according to the classification data.

The image designation data is for designating a particular image data 48 from the plurality of image data 48. More specifically, it represents a unique data (e.g., a file name or an identifier) of a particular image data 48. In displaying each of the screens A to D, the image designation data is referred to by the processor 31, the image data 48 designated according to the image designation data is read by the processor 31, and that image is displayed on the instrument display 11 by the processor 31.

The sub process presence/absence data represents whether a main process has a sub process or not. In displaying each of the screens A to D, the sub process presence/absence data is referred to by the processor 31 and whether a tag of the tag display 14 is to be displayed or not is determined by the processor 31. In displaying each of the screens A to D, when an operator operates the input 34, the sub process presence/absence data is referred to by the processor 31 and whether the screens A to D of the main process are to be changed to the screens B1 and D1 is determined by the processor 31.

FIG. 18 is a diagram showing a data configuration of the sub process data 47. Each sub process data 47 includes an upper-level process order data, a main process order data, a sub process order data, an operation detail data, and an image designation data.

The upper-level process order data represents the order of the upper-level process to which the sub process belongs. The sub process data 47 and the upper-level process data 45 having the same value of the upper-level process order data are associated with each other.

The main process order data represents the order of the main process to which the sub process belongs. The sub process data 47 and the main process data 46 having the same value of the main process order data are associated with each other. The sub process order data represents the order of the sub process. Transitions of the screens B to B1, the screens B1 to B2, the screens D to D1, and the screens D1 to D2 are performed based on the main process order data and the sub process order data. In displaying each of the screens B1, B2, D1, and D2, the main process order data and the sub process order are referred to by the processor 31, and a view of the order display 15 is determined by the processor 31 according to the main process order data and the sub process order.

The operation detail data is a text data representing details of the operation of the sub process. In displaying each of the screens B1, B2, D1, and D2, the operation detail data is referred to by the processor 31 and a view of the operation detail display 12 is determined by the processor 31 according to the operation detail data.

The image designation data is for designating a particular image data 48 from the plurality of image data 48. More specifically, it is a unique data (e.g., a file name or an identifier) of a particular image data 48. In displaying each of the screens B1, B2, D1, and D2, the image designation data is referred to by the processor 31, the image data 48 designated according to the image designation data is read by the processor 31, and that image is displayed on the instrument display 11.

As shown in FIG. 15, a basic program 41, a display program 42, and an operation flow creation assistance program (GUI program) 43 that can be executed by the processor 31 are stored in the storage 32.

The basic program 41 is for achieving an OS (Operating System) and a GUI (Graphical User Interface) of the OS. By starting and executing the basic program 41 by the processor 31, the storage 32, the display 33, the input 34, and the communicator 35 are controlled by the processor 31, and data are exchanged among them. For example, the processor 31 records date in and reads data from the storage 32. Further, the processor 31 supplies a video signal according to an arithmetic processing operation to the display 33, and a screen according to the video signal is displayed on the display 33. When the input 34 is operated, a signal according to how it was operated is supplied to the processor 31, and the processor performs an arithmetic processing operation according to the signal received from the input 34. Furthermore, since the communicator 35 is connected to a communication network 4 according to a predetermined protocol by being controlled by the processor 31, the processor 31, the server 2, and the terminals 3-2 and 3-3 are allowed to communicate wirelessly with each other via the communication network 4.

The display program 42 has been installed on the OS of the basic program 41 and can be executed by the processor 31 on the OS. The processor 31 reads the operation flow content 44 by the display program 42 being started and executed by the processor 31, and the processor 31 controls the display 33 so that transition of the screens (e.g., the screens A to D, B1, B2, D1, and D2) according to the operation flow content 44 will proceed according to how the input 34 was operated by the operator. Here, in displaying each of the screens (e.g., the screens A to D, B1, B2, D1, and D2) to be changed, the processor 31 determines views of the instrument display 11, the operation detail display 12, the order display 13, the tag display 14, the order display 15, and the process classification display according to the operation flow content 44 and generates each screen by rendering these views. The screens A to D, B1, B2, D1, and D2 that are examples of the transition of the screen are as described above.

The operation flow creation assistance program 43 has been installed on the OS of the basic program 41 and can be executed by the processor 31 on the OS. The GUI is operated by the input 34 by the operation flow creation assistance program 43 being started and executed by the processor 31 and the GUI is displayed on the display 33.

Figure 19:
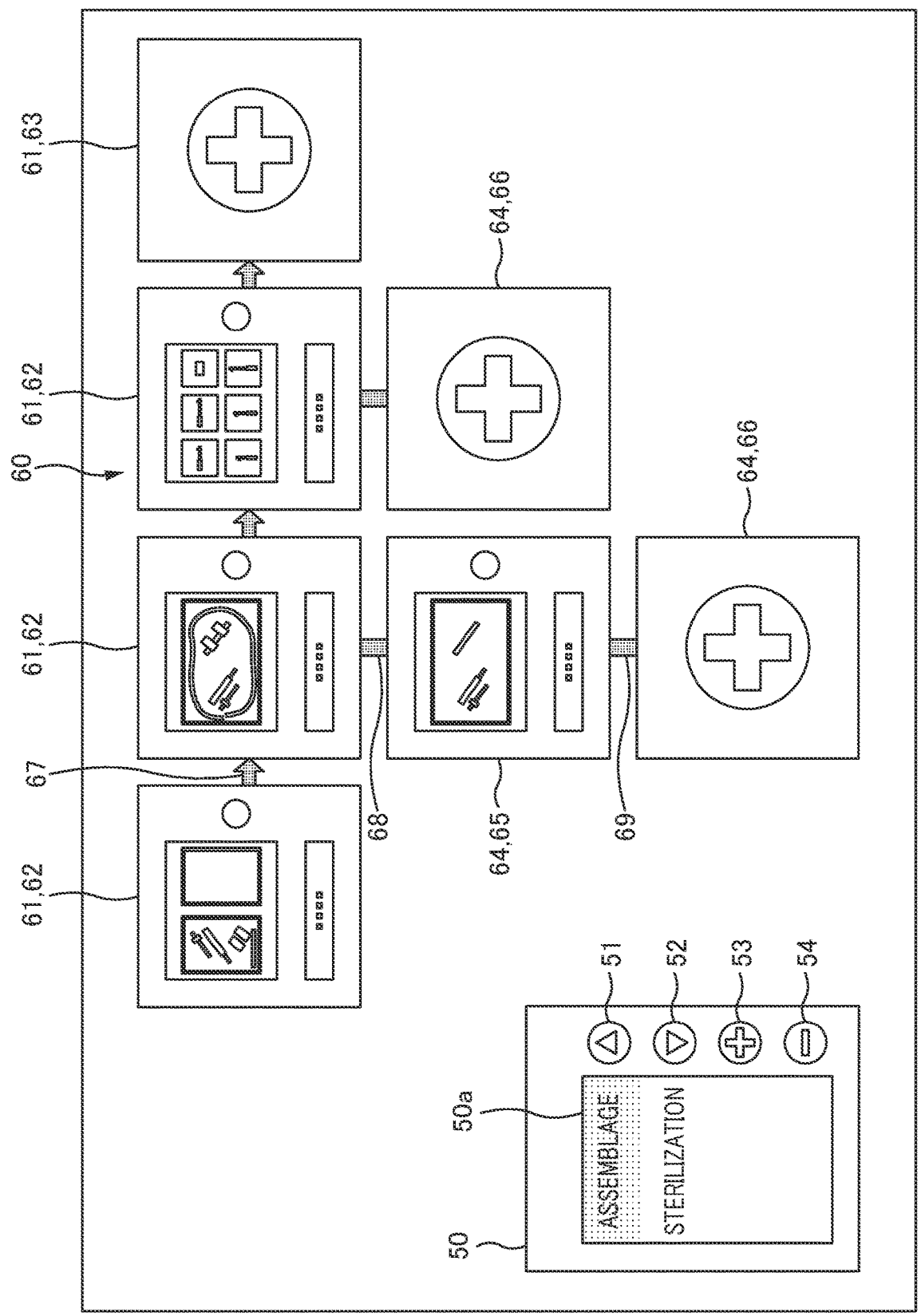
FIG. 19 a diagram showing an operation flow creation screen displayed on a display of a terminal.

FIG. 19 is an example of an operation flow creation screen displayed on the display 33. The operation flow creation screen shown in FIG. 19 is a GUI achieved when the processor 31 controls the display 33 according to the operation flow creation assistance program 43. Accordingly, when a user operates the input 34, the operation flow creation screen is operated by the processor 31 according to how it was operated.

The operation flow creation screen shown in FIG. 19 is for creating the orders and details of the operation of the main process and sub process belonging to a certain upper-level process. That is, under the assumption that the operation flow creation screen is a page, an operation flow creation screen is displayed for each upper-level process.

Here, the processor 31 generates an operation flow creation screen according to the operation flow creation assistance program 43, and supplies a video signal according to the operation flow creation screen to the display 33, whereby the operation flow creation screen as shown in FIG. 19 is displayed on the display 33. Upon generating the operation flow creation screen, the processor 31 arranges a page manipulation widget 50 and process widgets 61 and 64 on the operation flow creation screen and combines the page manipulation widget 50 and the process widgets 61 and 64 with the operation flow creation screen. Therefore, the page manipulation widget 50 is displayed on the left side of the operation flow creation screen displayed on the display 33, and the process widgets 61 and 64 representing the main and sub processes, respectively, belonging to an upper-level process of the medical instrument handling operation are displayed in an array arrangement in an area 60 on the right side of the page manipulation widget 50.

Each widget 61 displayed at the uppermost row of the operation flow creation screen is a main process widget representing each main process belonging to an upper-level process of the medical instrument handling operation and the other widgets, i.e., the widgets 64 are sub process widgets each representing a sub process belonging to the upper-level process of the medical instrument handling operation. These main process widgets 61 are arranged in a line in the lateral direction from the left to the right in the order of the main processes. When there are sub processes of the main process, the sub process widget 64 representing each sub process of the main process is arranged vertically from the top to the bottom of the screen under the main process widget 61 in the order of the sub processes.

A link mark 67 is displayed between the left and right sides of the adjacent main process widgets 61. The link mark 67 indicates that the main process is followed by the next main process.

When there are sub processes of the main process, a link mark 68 is displayed between the main process widget 61 and the sub process widget 64 on the lower side thereof. The link mark 68 indicates that the main process represented by the main process widget 61 on its upper side includes sub processes.

A link mark 69 is displayed between the upper and lower sides of the adjacent sub process widgets 64. The link mark 69 indicates that the sub process is followed by the next sub process.

Depending on the data of the operation flow content 44, the area 60 of the operation flow creation screen may be blank (a state in which the process widgets 61 and 64 and the link marks 67 to 69 are not displayed) in some cases.

Each main process widget 61 is associated with the main process data 46 on a one-to-one basis, and the association between the main process widget 61 and the main process data 46 is achieved by the main process order data. In other words, when generating and displaying the operation flow creation screen, the processor 31 refers to the main process order data of the main process data 46 to determine, based on the main process order data, a position where the main process widget is displayed in the operation flow creation screen. Therefore, the main process order data of the main process data 46 represents the position where the main process widget 61 associated with the main process data 46 is displayed (the place from the left of the screen).

When the main process data 46 is generated in the storage 32 by the processor 31, the processor 31 performs processing in such a way as adding the main process widget 61 to the operation flow creation screen. On the contrary, when the main process data 46 is deleted from the storage 32 by the processor 31, the processor 31 performs processing in such a way as deleting the main process widget 61 associated with the main process data 46 from the operation flow creation screen. The addition and deletion of the main process widget 61 will be described in detail later.

Each sub process widget 64 is associated with the sub process data 47 on a one-to-one basis, and the association between the sub process widget 64 and the sub process data 47 is achieved by the main process order data and the sub process order data. In other words, when generating and displaying the operation flow creation screen, the processor 31 refers to the main process order data and the sub process order data of the sub process data 47 to determine a position where the sub process widget 64 is displayed in the operation flow creation screen. Therefore, the main process order data and the sub process order data of the sub process data 47 represent the position where the sub process widget 64 associated with the sub process data 47 is displayed (the main process order data represents the place from the left of the screen and the sub process order data represents the place from the top of the screen).

Further, when the sub process data 47 is generated in the storage 32 by the processor 31, the processor 31 performs processing in such a way as adding the sub process widget 64 to the operation flow creation screen. On the contrary, when the sub process data 47 is deleted from the storage 32 by the processor 31, the processor 31 performs processing in such a way as deleting the sub process widget 64 associated with the sub process data 47 from the operation flow creation screen. The addition and deletion of the sub process widget 64 will be described in detail later.

Figure 20:
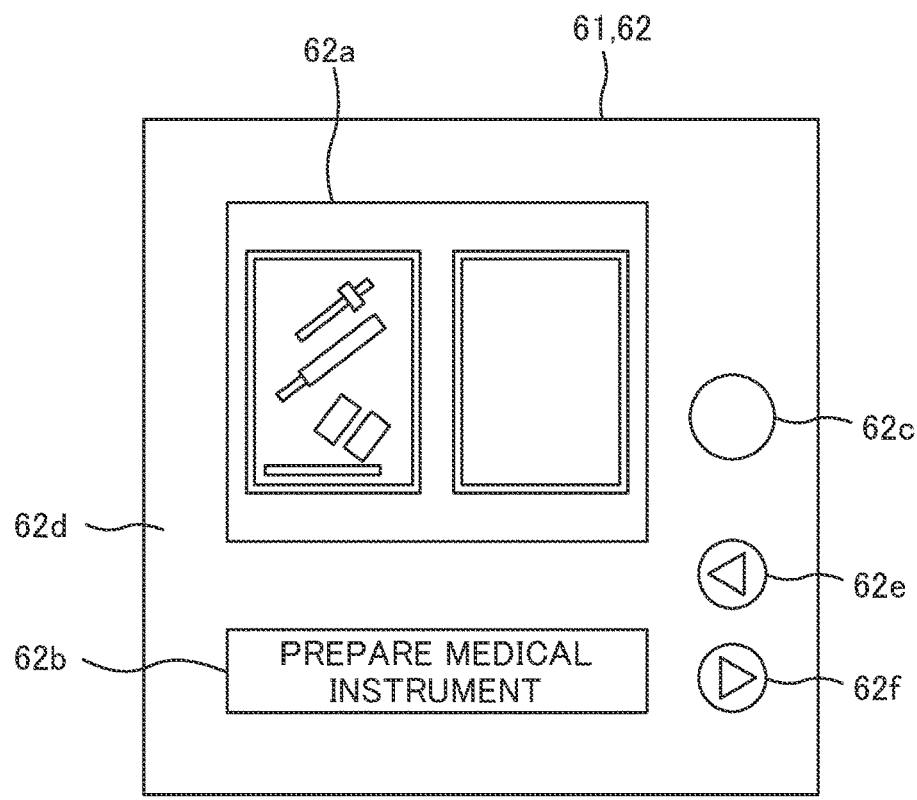
FIG. 20 is a diagram showing a registered widget of a main process displayed on the operation flow creation screen.
Figure 21:
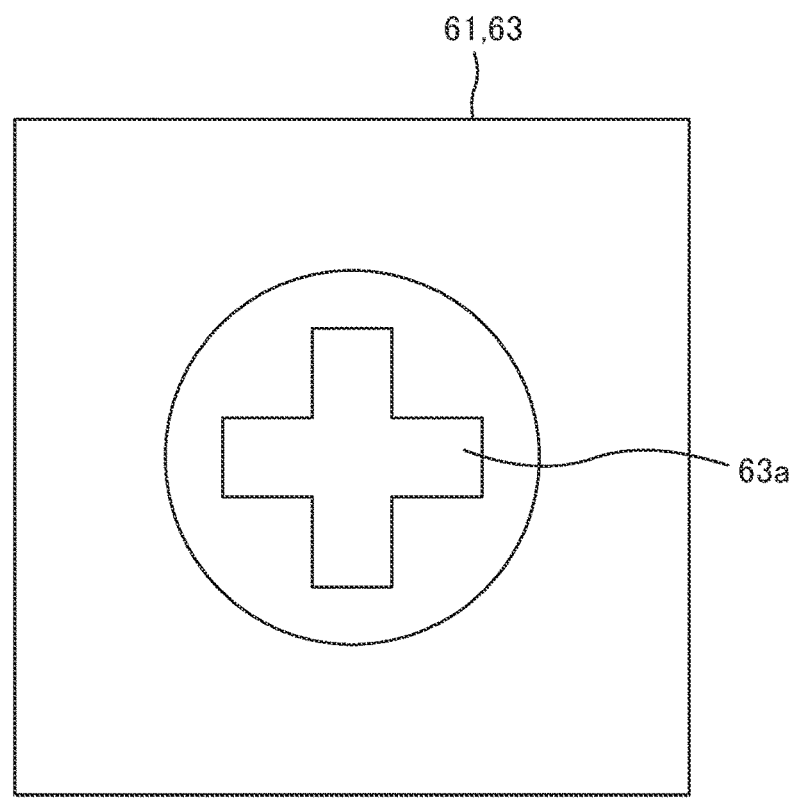
FIG. 21 is a diagram showing an unregistered widget of a main process displayed on the operation flow creation screen.

Each of the main process widgets 61 is classified as an operation registered widget 62 (hereinafter referred to as the registered widget 62) as shown in FIG. 20 and an operation unregistered widget 63 (hereinafter referred to as the unregistered widget 63) as shown in FIG. 21. The registered widget 62 indicates that an operation detail data, a classification data, and an image designation data have been registered in the main process data 46 associated with that registered widget 62 (the main process widget 61). The unregistered widget 63 indicates that a main process order data has been registered in the main process data 46 associated with that unregistered widget 63 (the main process widget 61), but an operation detail data, a classification data, and an image designation data have not yet been registered.

Figure 22:
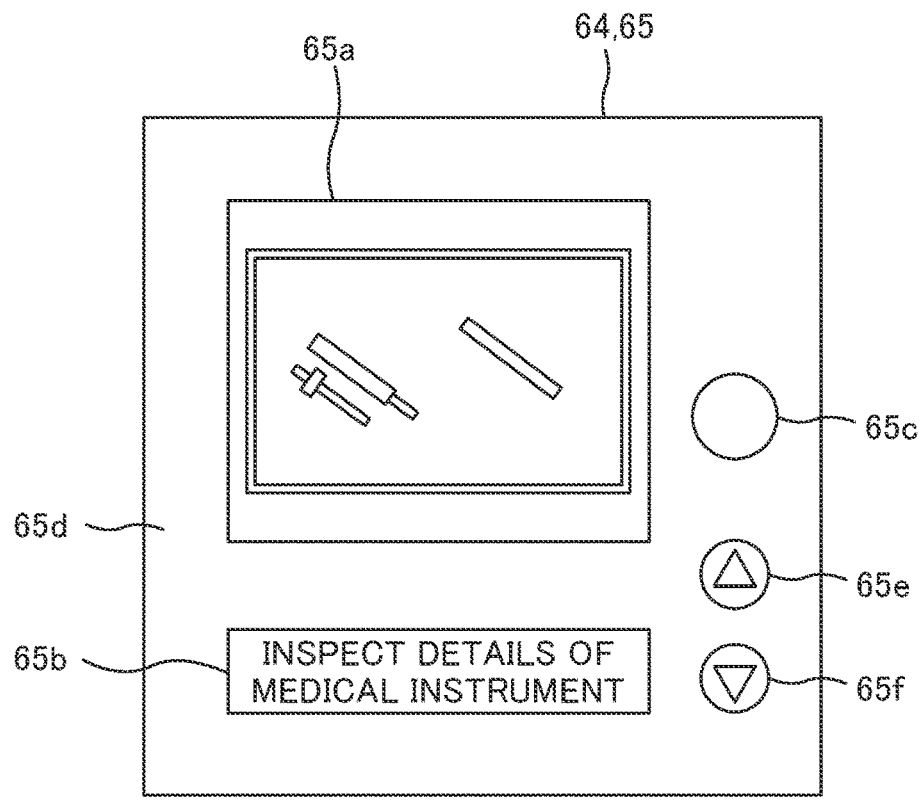
FIG. 22 is a diagram showing a registered widget of a sub process displayed on the operation flow creation screen.
Figure 23:
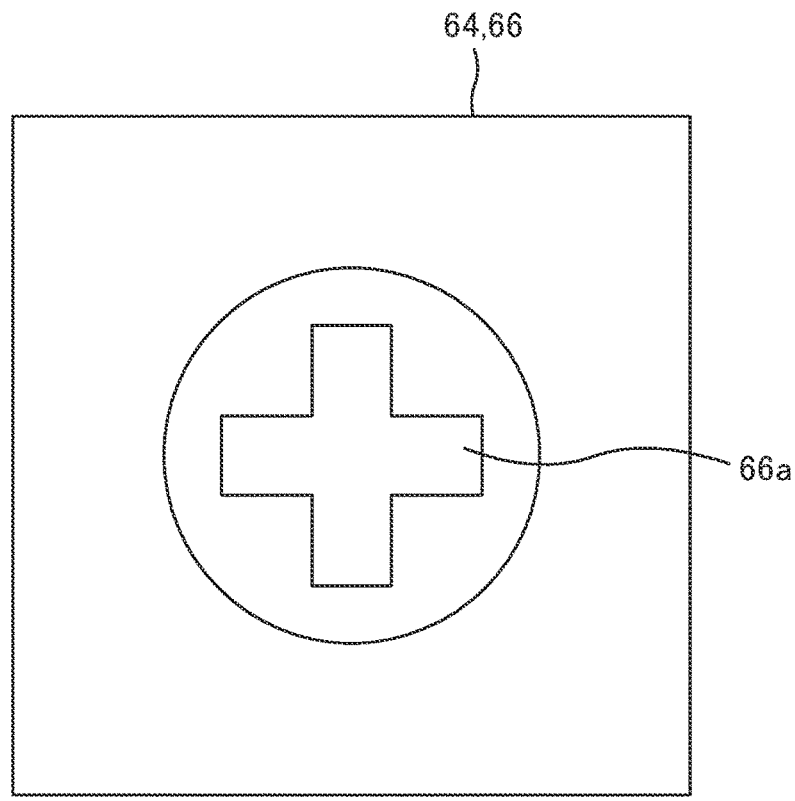
FIG. 23 is a diagram showing an unregistered widget of a sub process displayed on the operation flow creation screen.

Each of the sub process widgets 64 is also classified as an operation registered widget 65 (hereinafter referred to as the registered widget 65) as shown in FIG. 22 and an operation unregistered widget 63 (hereinafter referred to as the operation unregistered widget 63) as shown in FIG. 23. The registered widget 65 indicates that an operation detail data and an image designation data have been registered in the sub process data 47 associated with that registered widget 65 (the sub process widget 64). The unregistered widget 66 indicates that a main process order data and a sub process order data have been registered in the sub process data 47 associated with that unregistered widget 66 (the sub process widget 64), but an operation detail data and an image designation data have not yet been registered.

In the unregistered widgets 63 and 66, buttons 63*a* and 66*a* are displayed.

In the registered widgets 62 and 65, instrument displays 62*a* and 65*a*, operation detail displays 62*b* and 65*b*, edit buttons 62*c* and 65*c*, raising buttons 62*e* and 65*e*, and lowering buttons 62*f* and 65*f* are displayed.

An image of the image data 48 designated by the image designation data of the main process data 46 associated with the registered widget 62 (the main process widget 61) is displayed on the instrument display 62*a*. The content of the operation detail data of the main process data 46 associated with the registered widget 62 (the main process widget 61) is displayed on the operation detail display 62*b* as a text. That is, in generating and displaying the operation flow creation screen, the processor 31 refers to the operation detail data and the image designation data of the main process data 46 and determines a display image of the instrument display 62*a* and a display text of the operation detail display 62*b* based on the operation detail data and the image designation data.

An image of the image data 48 designated by the image designation data of the sub process data 47 associated with the registered widget 65 (the sub process widget 64) is displayed on the instrument display 65*a*. The content of the operation detail data of the sub process data 47 associated with the registered widget 65 (the sub process widget 64) is displayed on the operation detail display 65*b* as a text. That is, in generating and displaying the operation flow creation screen, the processor 31 refers to the operation detail data and the image designation data of the sub process data 47 and determines a display image of the instrument display 65*a* and a display text of the operation detail display 65*b* based on the operation detail data and the image designation data.

The registered widget 62 is classified as a normal operation process widget representing a normal operation process (detailed operation process), a quality important operation process widget representing a quality important operation process, and a count operation process widget representing a count operation process. Such classification is achieved by the classification data of the main process data associated with the registered widget 62. That is, the classification data of the main process data 46 represents the type of the registered widget 62 associated with the main process data 46. Then, the normal operation process widget, the quality important operation process widget and the count operation process widget are visually distinguishably displayed. That is, in generating and displaying the operation flow creation screen, the processor 31 refers to the classification data of the main process data 46 and determines the color of a background 62d of the registered widget 62 in the operation flow creation screen based on the classification data. For example, the background 62d of the registered widget 62 classified as a normal operation process widget is drawn in blue, and the backgrounds 62d of the registered widgets 62 classified as the quality important operation process widget and the count operation process widget are drawn in red. It should be noted that a background 65d of the registered widget (the sub process widget 64) is drawn in green, and the registered widget 65 and the registered widget 62 can be visually distinguished from each other.

As shown in FIG. 19, a list box 50a, a back button 51, a forward button 52, an add button 53, and a delete button 54 are displayed in the page manipulation widget 50. In the list box 50a, the contents of the operation name data of each of the upper-level process data 45 are displayed as a list (choice) in order, from the top, according to the order of the upper-level process.

Those selected from the list displayed in the list box 50a and those not selected are displayed so as to be visually distinguishable. For example, the selected list is displayed with a hatching, and the unselected list is displayed without hatching. The view of the area 60 of the operation flow creation screen is determined based on the main process data 46 and the sub process data 45 with their respective upper-level process order data identical to that of the upper-level process data 45 corresponding to the selected list.

The back button 51 and the forward button 52 are for changing the selection in the list box 50a. That is, when the back button 51 is selected and determined by the processor 31 according to an operation of the input 34 by the user, the selection (e.g., a hatching) is changed to one list above by the processor 31 and a view of the area 60 of the operation flow creation screen is changed based on the main process data 46 and the sub process data 45 with their respective upper-level process order data identical to that of the upper-level process data 45 corresponding to the selected list after the change. On the other hand, when the forward button 52 is selected and determined by the processor 31 according to how the input 34 was operated by the user, the selection (e.g., a hatching) is changed to one list below by the processor 31 and a view of the area 60 of the operation flow creation screen is changed based on the main process data 46 and the sub process data 45 with their respective upper-level process order data identical to that of the upper-level process data 45 corresponding to the selected list after the change.

The add button 53 of the page manipulation widget 50 is for adding a list to the list box 50a and newly generating the upper-level process data 45. That is, when a user selects one of the lists in the list boxes 50a by operating the input 34, the upper-level process data 45 corresponding to the selected list is selected by the processor 31. Thereafter, when the user selects and determines the add button 53 by operating the input 34, an operation name select screen or an operation name input screen is displayed. On the screen, when the user enters or selects an operation name by operating the input 34, a new upper-level process data 45 is generated in the storage 32 by the processor 31. Furthermore, returning to the operation flow creation screen, a list is added immediately below the selection list in the list box 50a, and one registered widget 62 (the main process widget 61) is displayed in the area 60 of the operation flow creation screen.

Here, in the list added to the list box 50a, an operation name that has been selected or entered on the operation name select screen or the operation name input screen is displayed. In a newly created upper-level process data 45, the operation name that has been selected or entered on the operation name select screen or the operation name input screen is registered as an operation name data. Furthermore, a value obtained by adding 1 to the value of the upper-level process order data of the selected upper-level process data 45 is registered in the upper-level process order data of the newly created upper-level process data 45. Moreover, 1 is added to values of the upper-level process order data of the upper-level process data 45 after the selected upper-level process data 45 (one having a larger value than the upper-level process order data of the selected upper process data 45) and the upper-level process order data of the main process data 46 and the sub process data 47 associated therewith, which are updated.

The delete button 54 of the page manipulation widget 50 is for deleting one list from the list box 50a and deleting one upper-level process data 45 and the main process data 46 and the sub process data 47 associated therewith from the storage 32.

Specifically, when a user selects a certain list in the list box 50a by operating the input 34, the upper-level process data 45 corresponding to the selected list is selected by the processor 31. Thereafter, the user selects and determines the delete button 54 by operating the input 34. Then, the selected upper-level process data 45 and the main process data 46 and the sub process data 47 associated therewith are deleted from the storage 32 by the processor 31. In addition, 1 is subtracted from values of the upper-level process data 45 after the deleted upper-level process data 45 (one having a larger value than the upper-level process order data of the deleted upper-level process data 45) and the main process data 46 and the sub process data 47 associated therewith, which are updated. Furthermore, a selection list in the list box 50a is deleted, and the view of the area 60 of the operation flow creation screen is changed based on the main process data 46 and the sub process data 45 with their respective upper-level process order data identical to that of the upper-level process data 45 immediately prior to or after the deleted upper-level process data 45.

As described above, each of the main process widgets 61 is classified as the registered widget 62 (see FIG. 20) and the unregistered widget 63 (FIG. 21). The main process widget can be changed from the unregistered widget 63 to the registered widget 62. Hereinafter, a process of changing the display of the main process widget 61 from the unregistered widget 63 to the registered widget 62 is described in detail.

Figure 24:
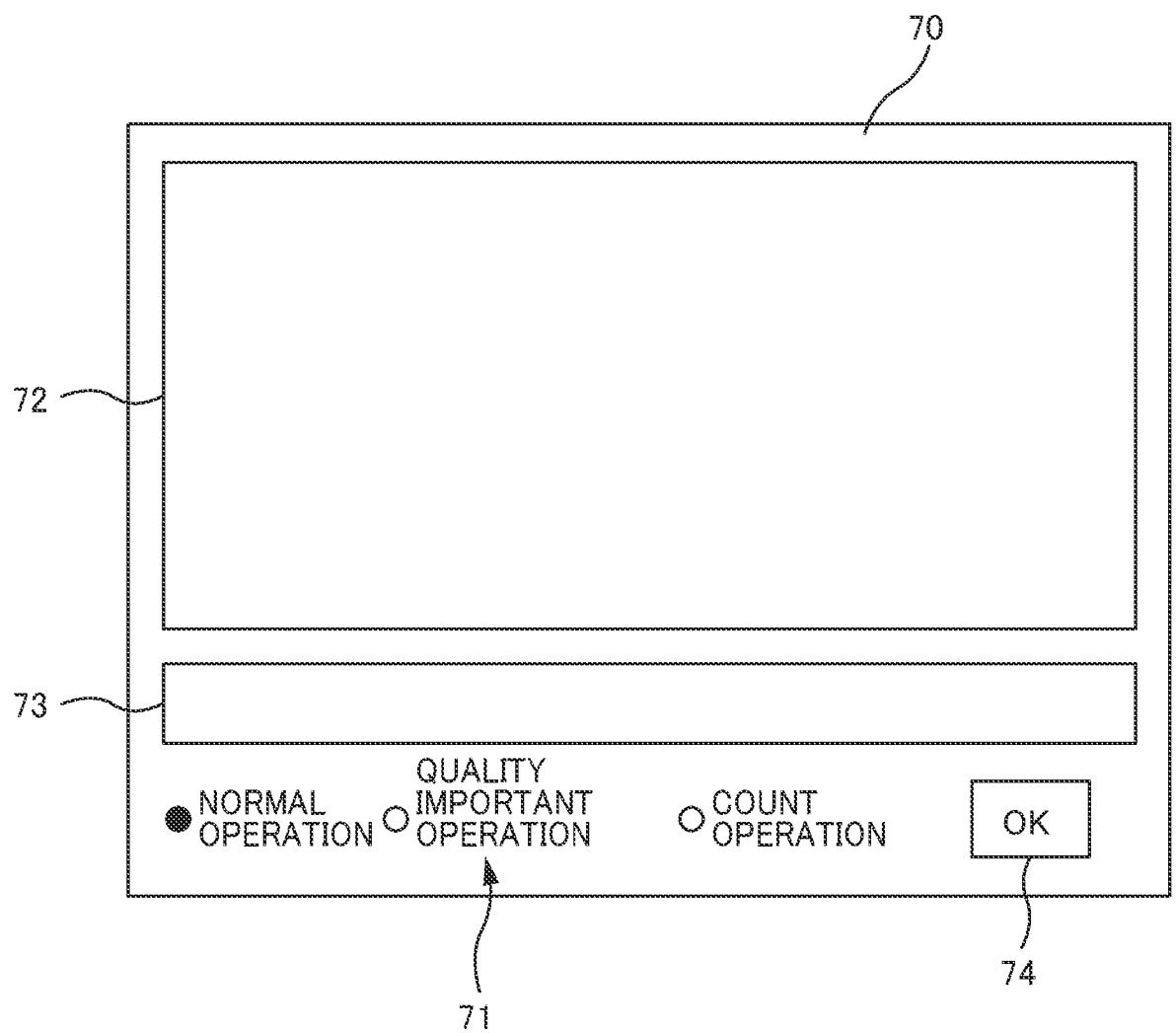
FIG. 24 is a diagram showing a data registration widget displayed on the operation flow creation screen.

When the unregistered widget 63 (in particular, a button 63a) is selected and determined by the processor 31 according to how the input 34 was operated by the user, a data registration widget 70 as shown in FIG. 24 is additionally displayed on the operation flow creation screen by the processor 31. In the data registration widget 70, a radio button 71, a selected image display 72, a text entry box 73, and a determination button 74 are displayed.

Thereafter, one of the plurality of options (a "normal operation," a "quality important operation," and a "count operation") of the radio button 71 is selected by the processor 31 according to how the input 34 was operated by the user. Further, when the user operates the input 34, a text according to how it was operated is entered into the text entry box 73. Further, according to how the input 34 was operated by the user, one or more image data 48 are selected from the plurality of image data 48 by the processor 31, and the image of the selected image data 48 is displayed on the selected image display 72 by the processor 31. Here, when the option of the "count operation" of the radio button 71 is selected, two or more image data 48 can be selected from the plurality of image data 48, and the images of the selected plurality of image data 48 are displayed in the selected image display 72 by the processor 31 in such a way as arranging them like an array in the selected image display 72. On the other hand, when the option of the "normal operation" or the "quality important operation" of the radio button 71 is selected, one image data 48 can be selected from the plurality of image data 48, and the image of the selected one image data 48 is displayed on the selected image display 72 by the processor 31 in the selected image display 72.

Thereafter, the determination button 74 is selected and determined by the processor 31 according to how the input 34 was operated by the user. As a result, the main process data 46 associated with the unregistered widget 63 is updated. Specifically, the option selected in the radio button 71 is recorded in the storage 32 by the processor 31 as classification data of the main process data 46 associated with the unregistered widget 63. Further, the text entered into the text entry box 73 is recorded in the storage 32 by the processor 31 as the operation detail data of the main process data 46 associated with the unregistered widget 63. Furthermore, a unique data (e.g., a file name or an identifier) of the selected image data 48 of the image displayed on the selected image display 72 is recorded in the storage 32 by the processor 31 as the image designation data of the main process data 46 associated with the unregistered widget 63.

When the main process data 46 associated with the unregistered widget 63 is updated as described above, as shown in FIGS. 25A and 25B, an operation flow creation screen is displayed on the display 33 by the processor 31 in such a way as changing the unregistered widget 63 to the registered widget 62. At this time, the processor 31 refers to the updated main process data 46 and generates the registered widget 62 on the operation flow creation screen based on the main process data 46. That is, the processor 31 determines the display text of the operation detail display 62b of the registered widget 62 based on the operation detail data of the updated main process data 46, determines a display image of the instrument display 62a among the plurality of image data 48 based on the image designation data of the main process data 46, and determines the color of the background 62d based on the classification data of the main process data 46. Here, the screen shown in FIG. 25A is an example of the operation flow creation screen before the display of the unregistered widget 63 is changed to the registered widget 62, and the screen shown in FIG. 25B is an example of the operation flow creation screen after the unregistered widget 63 has been changed and displayed as the registered widget 62.

Figure 25A:
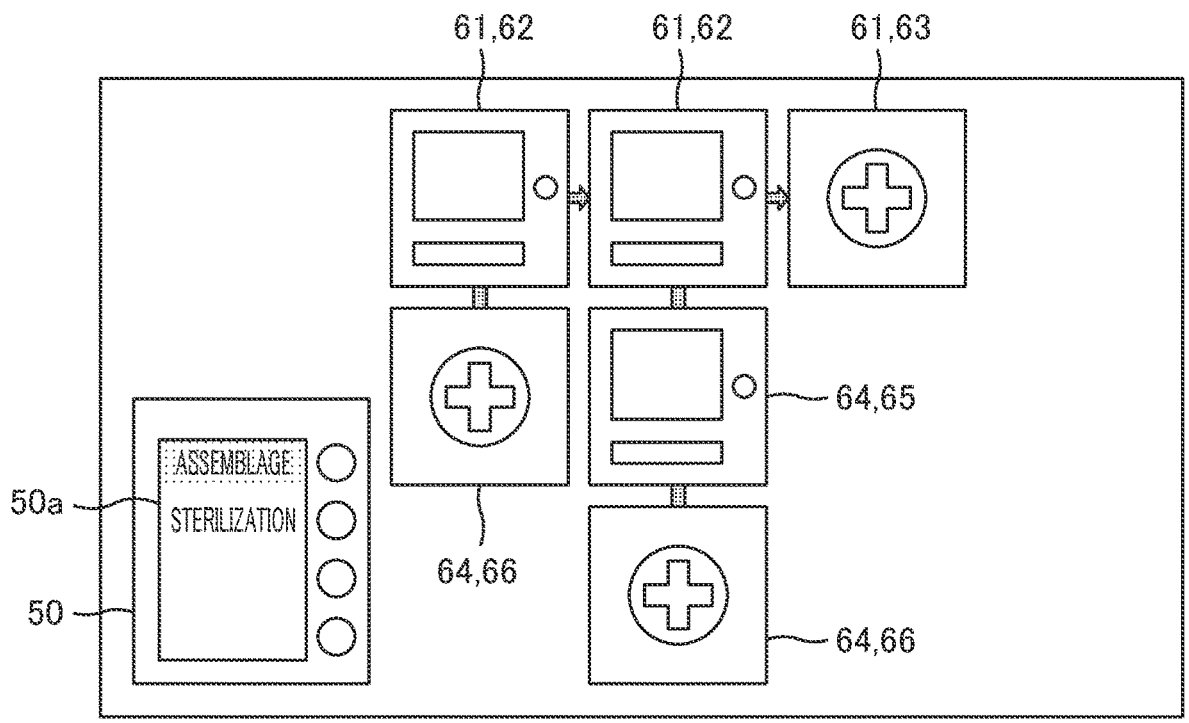
FIG. 25A is a diagram showing the operation flow creation screen before unregistered widgets of a main process are changed to registered widgets.
Figure 25B:
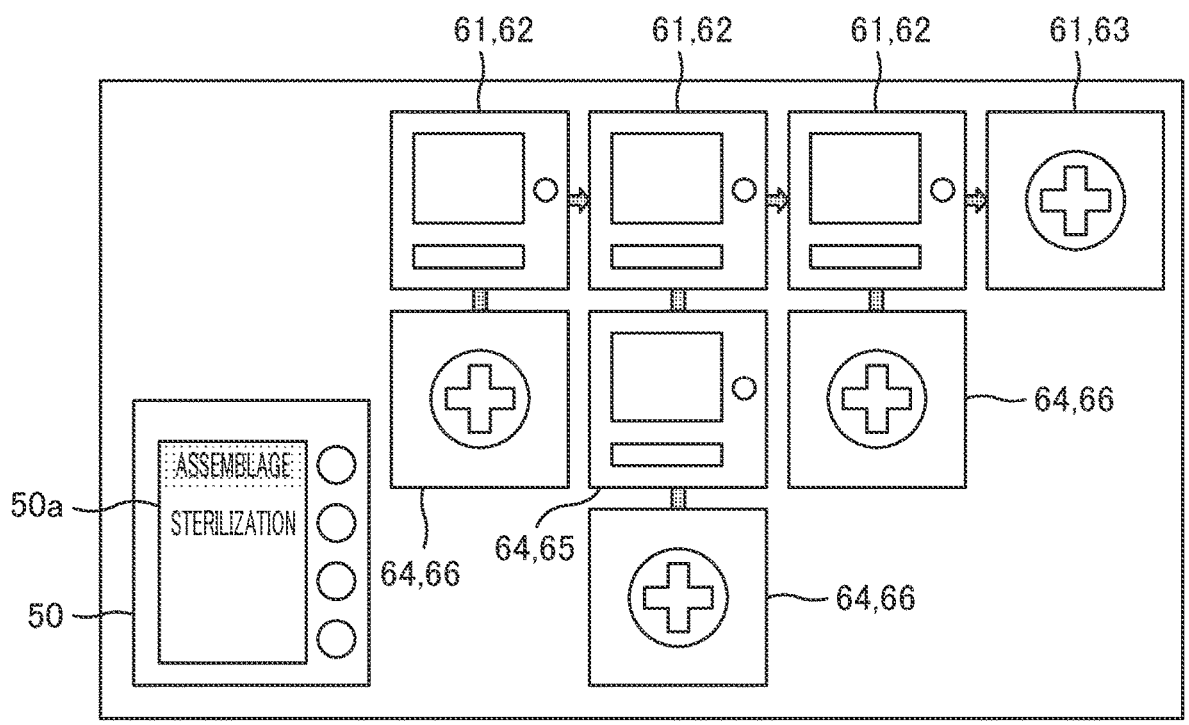
FIG. 25B is a diagram showing the operation flow creation screen after the unregistered widgets of the main process have been changed to registered widgets.
Figure 26A:
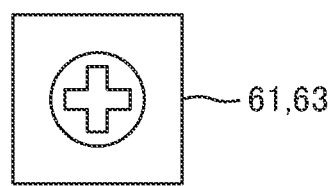
FIG. 26 is a diagram illustrating that unregistered widgets of a main process and a sub process are successively displayed in a lateral direction in the order of 26A to 26D.
Figure 26B:
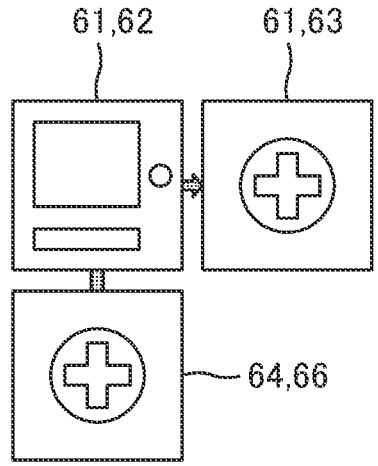
Figure 26C:
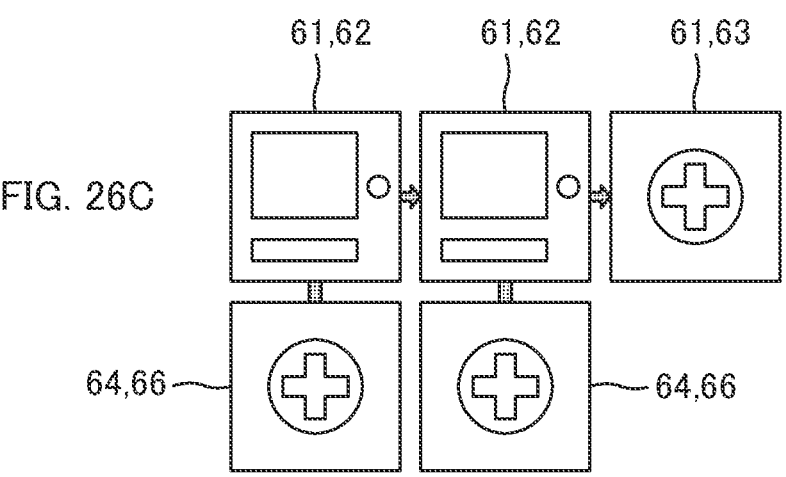
Figure 26D:
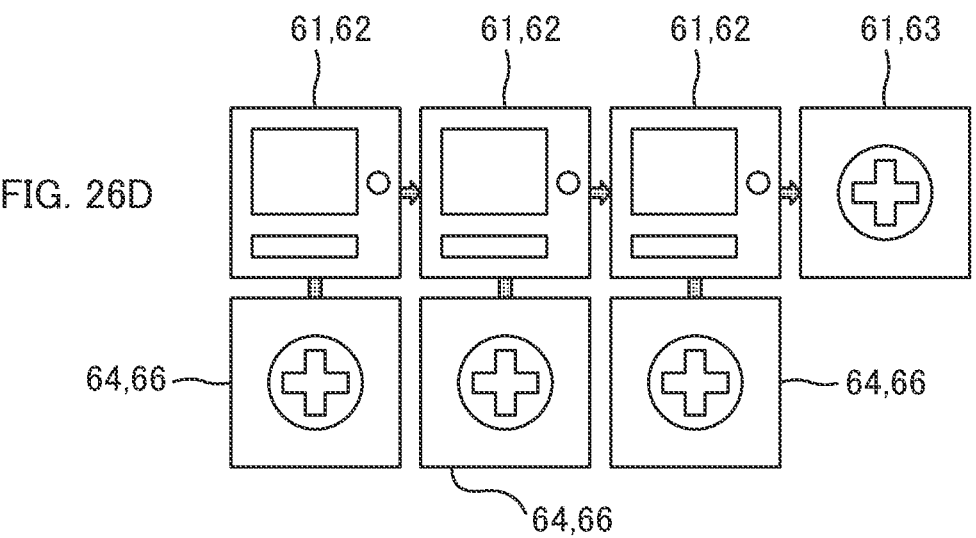

When the unregistered widget 63 is changed to the registered widget 62 as described above, the operation flow creation screen is displayed on the display 33 by the processor in such a way as adding a new sub process widget 64 (in particular, an unregistered widget 66) at a position adjacent to the lower end of the changed registered widget 62 (see FIGS. 25A and 25B). Further, a new sub process data 47 is generated on the storage 32 by the processor 31. A value of the upper-level process order data of the upper-level process data 45 corresponding to the selection list in the list box 50a is registered in the upper-level process order data of the newly generated sub process data 47. The value of the main process order data of the main process data 46 associated with the registered widget 62 changed from the unregistered widget 63 is registered in the main process order data of the newly generated sub process data 47. In addition, a value of "1" is registered in the sub process order data of the newly generated sub process data 47. Since the image designation data and the operation detail data of the newly generated sub process data 47 have not yet been registered at this point of time, a newly displayed sub process widget 64 is the unregistered widget 66 (see FIG. 25B)).

When the unregistered widget 63 is changed to the registered widget 62 as described above, the operation flow creation screen is displayed on the display 33 by the processor 31 in such a way as adding a new main process widget 61 (in particular, the unregistered widget 63) at a position adjacent to the right end of the changed registered widget 62 (see FIGS. 25A and 25B). Further, a main process data 46 is generated on the storage 32 by the processor 31. A value of the upper-level process order data of the upper-level process data 45 corresponding to the selection list in the list box 50a is registered in the upper-level process order data of the newly generated main process data 46. A value obtained by adding 1 to the value of the main process order data of the main process data 46 associated with the registered widget 62 changed from the unregistered widget 63 is registered in the main process order data of the newly generated main process data 46. Since the operation detail data, the classification data, and the image designation data of the newly generated main process data 46 are not registered at this point of time, a newly displayed main process widget 61 is the unregistered widget 63 (see FIG. 25B)).

Therefore, when the user repeatedly performs operations as mentioned above, as shown in FIGS. 26A to 26D, the unregistered widgets 63 (the main process widgets 61) and the unregistered widgets 66 (the sub process widgets 64) are displayed successively from the left to the right of the operation flow creation screen as in the order of FIGS. 26A to 26D and the change of the display from the unregistered widget 63 to the registered widget 62 is performed successively from the left to the right of the operation flow creation screen as in the order of FIGS. 26A to 26D.

Each of the sub process widgets 64 is also classified as the registered widget 65 (see FIG. 22) and the unregistered widget 66 (FIG. 23). The sub process widget 64 can be changed from the unregistered widget 66 to the registered widget 65. Hereinafter, a process of changing the display of the sub process widget 64 from the unregistered widget 66 to the registered widget 65 is described.

When the unregistered widget 66 (in particular, a button 66a) is selected and determined by the processor 31 according to how the input 34 was operated by the user, the data registration widget 70 (see FIG. 24) is displayed. At this time, however, no radio button 71 is displayed on the data registration widget 70. Then, as in the case of changing the main process widgets 61 from the unregistered widget 63 to the registered widget 62, the user operates the data registration widget 70 using the input 34 and the sub process data 47 associated with the unregistered widget 66 is updated.

Specifically, the text entered into the text entry box 73 is recorded in the storage 32 by the processor 31 as the operation detail data of the sub process data 47 associated with the unregistered widget 66. Furthermore, a unique data (e.g., a file name or an identifier) of the selected image data 48 of the image displayed on the selected image display 72 is recorded in the storage 32 by the processor 31 as the image designation data of the sub process data 47 associated with the unregistered widget 66.

When the sub process data 47 associated with the unregistered widget 66 is updated as described above, as shown in FIGS. 27A and 27B, an operation flow creation screen is displayed on the display 33 by the processor 31 in such a way as changing the unregistered widget 66 to the registered widget 65. At this time, the processor 31 refers to the updated sub process data 47 and generates the registered widget 65 on the operation flow creation screen based on the sub process data 47. That is, the processor 31 determines the display text of the operation detail display 65b of the registered widget 65 based on the operation detail data of the updated sub process data 47 and determines a display image of the instrument display 65a among the plurality of image data 48 based on the image designation data of the sub process data 47. Here, the screen shown in FIG. 27A is an example of the operation flow creation screen before the display of the unregistered widget 66 is changed to the registered widget 65, and the screen shown in FIG. 27B is an example of the operation flow creation screen after the unregistered widget 66 has been changed and displayed as the registered widget 65.

Figure 27A:
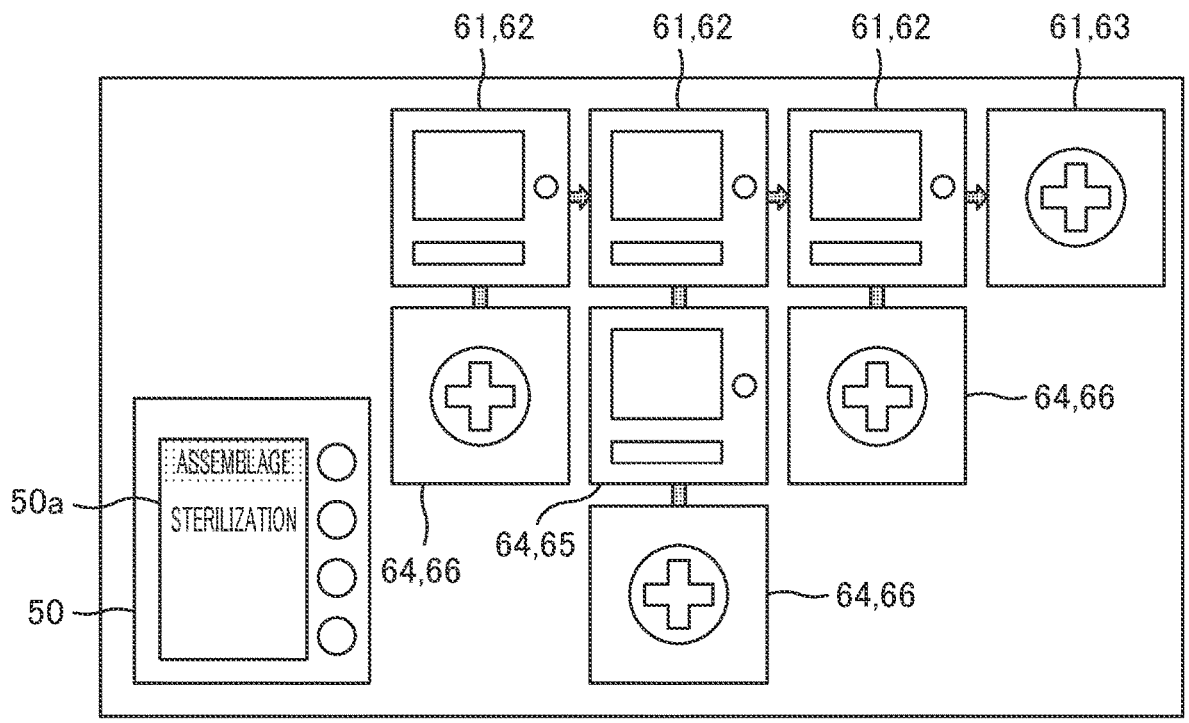
FIG. 27A is a diagram showing the operation flow creation screen before unregistered widgets of a sub process are changed to registered widgets.
Figure 27B:
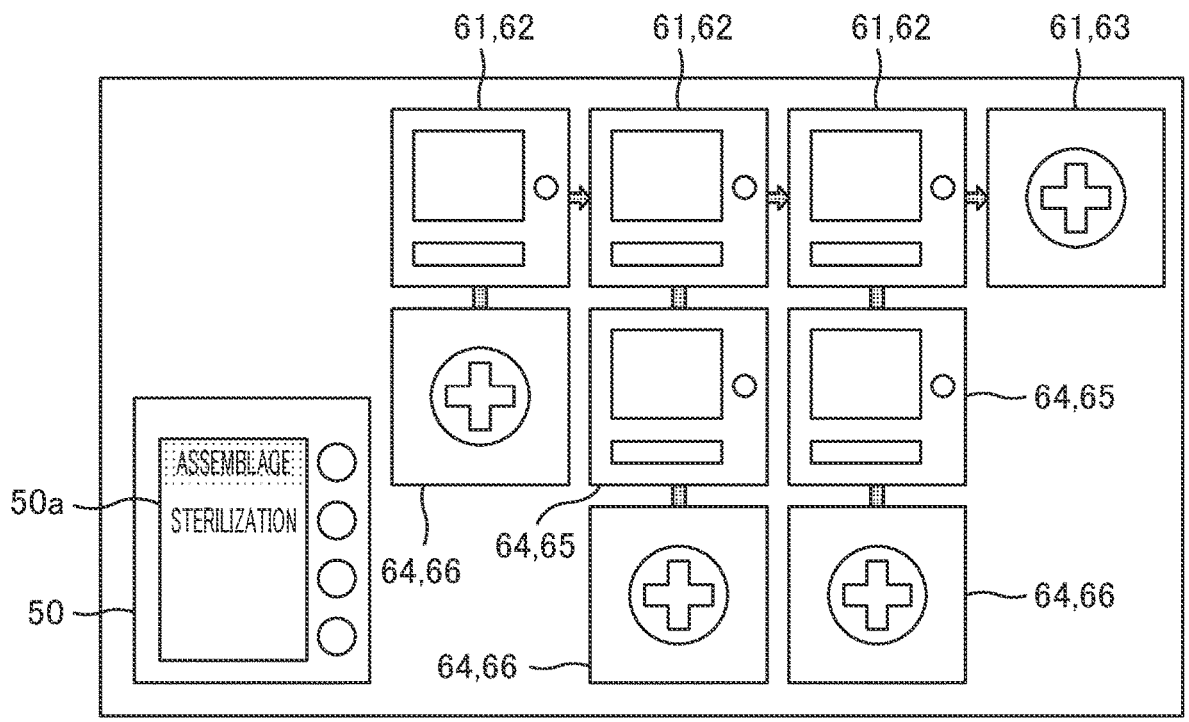
FIG. 27B is a diagram showing the operation flow creation screen after the unregistered widgets of the sub process have been changed to registered widgets.

When the unregistered widget 66 is changed to the registered widget 65 as described above, the operation flow creation screen is displayed on the display 33 by the processor in such a way as adding a new sub process widget 64 (in particular, an unregistered widget 66) at a position adjacent to the lower end of the changed registered widget 65 (see FIGS. 27A and 27B). Further, a new sub process data 47 is generated on the storage 32 by the processor 31. A value of the upper-level process order data of the upper-level process data 45 corresponding to the selection list in the list box 50a is registered in the upper-level process order data of the newly generated sub process data 47. The value of the main process order data of the main process data 46 associated with the registered widget 65 changed from the unregistered widget 66 is registered in the main process order data of the newly generated sub process data 47. A value obtained by adding 1 to the value of the sub process order data of the main process data 46 associated with the registered widget 65 changed from the unregistered widget 66 is registered in the sub process order data of the newly generated sub process data 47. Since the image designation data and the operation detail data of the newly generated sub process data 47 have not yet been registered at this point of time, a newly displayed sub process widget 64 is the unregistered widget 66 (see FIG. 27B)).

Accordingly, when the user repeatedly performs the above-described operations, as shown in FIGS. 28A to 28D, the unregistered widgets 66 (the sub process widgets 64) are displayed one after another from the top to the bottom of the operation flow creation screen in the order shown in FIGS. 28A to 28D and the change of the display from the unregistered widget 66 to the registered widget 65 is performed successively from the top to the bottom of the operation flow creation screen in the order shown in FIGS. 28A to 28D.

The edit buttons 62c and 65c are displayed in the registered widgets 62 and 65 (see FIGS. 20 and 22). These edit buttons 62c and 65c are for changing or deleting a portion of the process data 45 and 46. In other words, when the edit button 62c of one of the registered widgets 62 is selected and determined by the processor 31 according to how the input 34 was operated by the user, it is possible to partially change or delete the main process data 46 associated with the selected registered widget 62.

Thereafter, according to how the input 34 was operated by the user, the operation detail data, the classification data or the image designation data of the main process data 46 associated with the selected registered widget 62 is changed by the processor 31. The main process data 46 after the change is updated and recorded in the storage 32 by the processor 31. Then, the processor 31 refers to the updated main process data 46, and based on that main process data 46, it changes the display of the instrument display 62a, the operation detail display 62b or the background 62d of the registered widget 62 in the operation flow creation screen.

On the other hand, when the operation detail data, the classification data, and the image designation data of the main process data 46 associated with the selected registered widget 62 are deleted by the processor 31 according to how the input 34 was operated by the user, the main process data 46 after the change is updated and recorded in the storage 32 by the processor 31. Then, the operation flow creation screen is displayed on the display 33 by the processor 31 in such a way as changing the selected registered widget 62 to the unregistered widget 63.

Similarly, when the edit button 65c of one of the registered widgets 65 is selected and determined by the processor 31 by the user's operating the input 34, it is possible to partially change or delete the sub process data 65 associated with the selected registered widget 65.

The raising buttons 62e and 65e and the lowering buttons 62f and 65f are arranged in the registered widgets 62 and 65 (see FIGS. 20 and 22). The raising buttons 62e and 65e are for moving up the order of the registered widgets 62 and 65 and the lowering buttons 62f and 65f are for moving down the order of the registered widgets 62 and 65. That is, when the raising button 62e (or the lowering button 62f) of one of the registered widgets 62 (the main process widgets 61) is selected and determined by the processor 31 by the user's operating the input 34, the processor 31 causes the display 33 display the operation flow creation screen in such a way as permuting a column of the selected registered widget 62 (the main process widget 61) and the underneath sub process widget and a column of the main process widget 61 and the underneath sub process widget 64 next to the selected registered widget (the main process widget 61) on its left (on its right for the lowering button 62f). Along with this, the processor 31 replaces the main process order data of the process data 46 and 47 associated with the selected process widgets 61 and 64 with the main process order data of the process data 46 and 47 associated with the process widgets 61 and 64 on their left (or on their right for the lowering button 62f) and updates and records the process data 46 and 47 after the replacement in the storage 32.

As described above, for the user, replacement of the two main process widgets 61 and replacement of the orders of the main process can be easily achieved.

When the raising button 65e (or the lowering button 65f) of one of the registered widgets 65 (the sub process widgets 64) is selected and determined by the processor 31 by the user's operating the input 34, the processor 31 causes the display 33 display the operation flow creation screen in such a way as permuting the selected sub process widget 64 and the adjacent sub process widget 64 above (underneath for the lowering button 65f). Along with this, the processor 31 replaces the sub process order data of the sub process data 47 associated with the selected sub process widget 64 with the sub process order data of the sub process data 47 associated with the sub process widget 64 above (or underneath for the lowering button 65f) and updates and records the sub process data 47 after the replacement in the storage 32.

As described above, for the user, replacement of the two sub process widgets 64 and replacement of the orders of the sub process can be easily achieved.

When a printer is connected to the terminal 3-1, printing can be performed. That is, when the user operates the input 34 to cause the processor 31 execute a printing process, the processor 31 converts the area 60 of the operation flow creation screen into print data and transmits the print data to the printer. As a result, the image of the area 60 of the operation flow creation screen is formed on the medium (for example, paper) by the printer.

According to the above preferred embodiment, the following effects can be obtained.

(1) By using the system 1 as described above, it is possible to easily create a manual (the screen transition achieved by the operation flow contents 44 and the display program 42) of handling operations for medical instruments. In other words, the GUI operation flow creation screen is superior in visibility and operability, and the user can intuitively operate the GUI operation flow creation screen with the input 34 while looking at the operation flow creation screen of the display 33.

(2) As described above, when the operation detail data, the image designation data and the classification data are added to the main process data 46 associated with the unregistered widget 63, the unregistered widget 63 is changed to the registered widget 62 and the unregistered widget 63 is automatically displayed on its right and the unregistered widget 66 is automatically displayed underneath. Therefore, even a user unfamiliar with the user interface can intuitively continue to create the process data 45 and 47 associated with the newly displayed unregistered widgets 63 and 66. In other words, it is possible to continuously create a manual of handling operations for medical instruments.

(3) As described above, when the operation detail data, the image designation data, and the classification data are added to the sub process data 47 associated with unregistered widget 66, the unregistered widget 66 is changed to the registered widget 65, and the unregistered widget 66 is automatically displayed below. Therefore, even a user unfamiliar with the user interface can intuitively continue to create the process data 47 associated with the newly displayed unregistered widget 66. In other words, it is possible to continuously create a manual of handling operation procedures for medical instruments.

(4) By using the data registration widget 70 as shown in FIG. 24, it is possible to easily enter the operation detail data, the image designation data, and the classification data into the process data 45 and 47.

(5) Since the registered widgets 62 (the main process widgets 61) are aligned in the order of processes, the user or the like can intuitively recognize the order of the main processes of the handling operations for medical instruments. The order of the sub processes of the main processes can also be recognized intuitively by the registered widgets 65 (the sub process widgets 64).

(6) Regardless of which user or users create(s) a manual (the screen transition achieved by the operation flow content 44 and the display program 42) of handling operations for medical instruments using the system 1, the manual follows a certain style (template). Therefore, regardless of which user or users create(s) a manual, the quality of the manual satisfies certain criteria.

(1) In the above preferred embodiments, the operation flow content 44 is created using the terminal 3-1, but the operation flow content 44 may be created using the terminal 3-2, 3-3 or the server 2. That is, each of the terminals 3-1, 3-2, 3-3 and the server 2 is an assistance device and a GUI device. The display program 42, the operation flow creation program 43, and the image data 48 are synchronized among the terminals 3-1, 3-2, and 3-3 and the server 2, and the operation flow content 44 created by any of the terminals 3-1 to 3-3 and the server 2 is also synchronized among the terminals 3-1, 3-2, and 3-3 and the server 2.

(2) In the above preferred embodiments, the main process widgets 61 are arranged in the uppermost row in the lateral direction in the operation flow creation screen, and the sub process widgets 64 are arranged in the vertical direction under each main process widget 61. Alternatively, the main process widgets 61 may be arranged in the vertical direction on the left side (or the right side) of the operation flow creation screen and the sub process widgets 64 may be arranged in the lateral direction on the left side (the left side) of each main process widget 61. In this case, if the user repeatedly performs the operation described above, the unregistered widgets 63 (the main process widgets 61) and the unregistered widgets 66 (the sub process widgets 64) are sequentially displayed from the left to the right (or from the right to the left) of the operation flow creation screen, and the change of the display from the unregistered widget 66 to the registered widget 65 is executed from the left to the right (or from the right to the left) of the operation flow creation screen one after another.

(3) In the above preferred embodiments, each image data 48 shows a medical instrument and the manual to be created (the screen transition achieved by the operation flow content and the display program 42) is the manual of handling operations for medical instruments. On the other hand, the image data 48 may show items other than medical instruments (a display screen of a display displayed by application software, a personal computer, a mobile phone, a home appliance, household goods, furniture, a fitting, a machine tool, a cutting machine, etc.), and the manual to be created (the screen transition achieved by the operation flow content 44 and the display program 42) may be a manual of handling operations for articles other than medical instruments.

Sixth Preferred Embodiment

The invention according to this preferred embodiment relates to programs for recording information about a certain version of a content.

Conventionally, management systems have been used for the purpose of, for example, managing inventory of articles such as medical instruments. For example, in a technique described in JP-A-2005-237586, data such as the number of times each surgical instrument was used, the time at which it was sterilized, a person who sterilized it, a storage location, the time at which storage was started, and a warden are managed in the database using an identification tag assigned to surgical instruments that can be re-used.

Further, for example, in a technique described in JP-A-2008-54732, since information indicating the completion of cleaning and information indicating the cleaning date are recorded in an IC tag for an endoscope after cleaning of that endoscope has been completed, no such information is recorded in an IC tag for an endoscope that has not yet been cleaned. Therefore, before the use of an endoscope, by reading the information stored in the IC tag for the endoscope by an IC tag reader, it is possible to recognize whether the endoscope has already been cleaned or not.

By the way, articles such as medical instruments can exhibit their performance by being properly handled. Therefore, an instruction manual describing accurate handling of articles is required, and users handle the articles while reading the instruction manual. For example, as a handling operation for medical instruments such as surgical instruments, the medical instruments are disassembled, cleaned, assembled after the cleaning, after which the medical instruments are sterilized. At that time, an operator performs operations while checking a way of handling using an instruction manual.

The instruction manuals, however, contain explanations on functions not used in the actual site of use, and the description of the instruction manual is long. On the other hand, the contents of the instruction manual may be insufficient for the explanation. Therefore, for the site of use where articles such as medical instruments are used, new descriptions may be prepared based on the instruction manual. If the instruction manual has some problems, it is necessary to revise the instruction manual in order to solve the problems. Repeated revisions of the instruction manual, however, causes it difficult to judge when, who, and what each revision was done.

Therefore, the invention according to this preferred embodiment has been made in view of the above circumstances, and the problem to be solved by the invention according to this preferred embodiment is to cause it possible to know information about revised versions such as information of the time, the editor (s), and the reason(s).

According to a preferred embodiment of the present invention, a non-transitory computer-readable medium includes a program for causing a computer, the computer having a function of editing contents for representing a flow of a medical instrument handling operation and a function of recording the contents in a storage according to versions thereof, to execute: a storage step of storing a certain version of the contents; and a recording step of recording a version information about the certain version in the storage.

Other features of the invention according to this preferred embodiment are disclosed in the descriptions of the specification and the drawings that follow.

With the invention according to this preferred embodiment, whenever a version of a content is recorded, a version information such as a version number, a save time, and an editor is recorded in a storage. Accordingly, it is possible to know the version information related to a version.

In the descriptions of the specification and the drawings that follow, at least the following features are disclosed.

According to a preferred embodiment of the present invention, a non-transitory computer-readable medium includes a program for causing a computer, the computer having a function of editing contents for representing a flow of a medical instrument handling operation and a function of recording the contents in a storage according to versions thereof, to execute: a storage step of storing a certain version of the contents; and a recording step of recording a version information about the certain version in the storage is disclosed.

With the program mentioned above, since the version information is stored in the storage, it is possible to know the version information.

Preferably, the version information includes an information representing the number of the certain version.

According to the above, since the information representing the version number is stored in the storage, it is possible to know a certain version of a content is which version.

The version information includes an information representing a storage time of the certain version.

According to the above, since the information representing the storage time is recorded in the storage, it is possible to know a storage time of a certain version of a content.

Preferably, the version information includes an information representing an editor who has edited the contents and stored the certain version.

According to the above, since the information representing the editor is stored in the storage, it is possible to know an editor of a certain version of a content.

Preferably, the version information includes an information representing a reason why the contents have been edited.

According to the above, since the information representing the reason for edition is recorded in the storage, it is possible to know a reason for edition of a certain version of a content.

Preferably, the program is for causing the computer to execute: a read step of reading the certain version from the storage for the use of the contents; and a second record step of recording, in the storage, a time-of-use information representing a read time of the certain version.

According to the above, it is possible to know a read time and a time of use of a certain version.

Preferably, the second record step is for recording, in the storage, an information representing a user who has made a certain version be read using the contents in association to the time-of-use information.

According to the above, it is possible to know a user of a certain version of a content.

Referring to the drawings, a preferred embodiment of the present invention is described below. The preferred embodiment described below includes various limitations that are technically preferable for the purpose of implementing the present invention; therefore, the scope of the present invention is not limited to the following preferred embodiment and illustrated examples.

Figure 29:
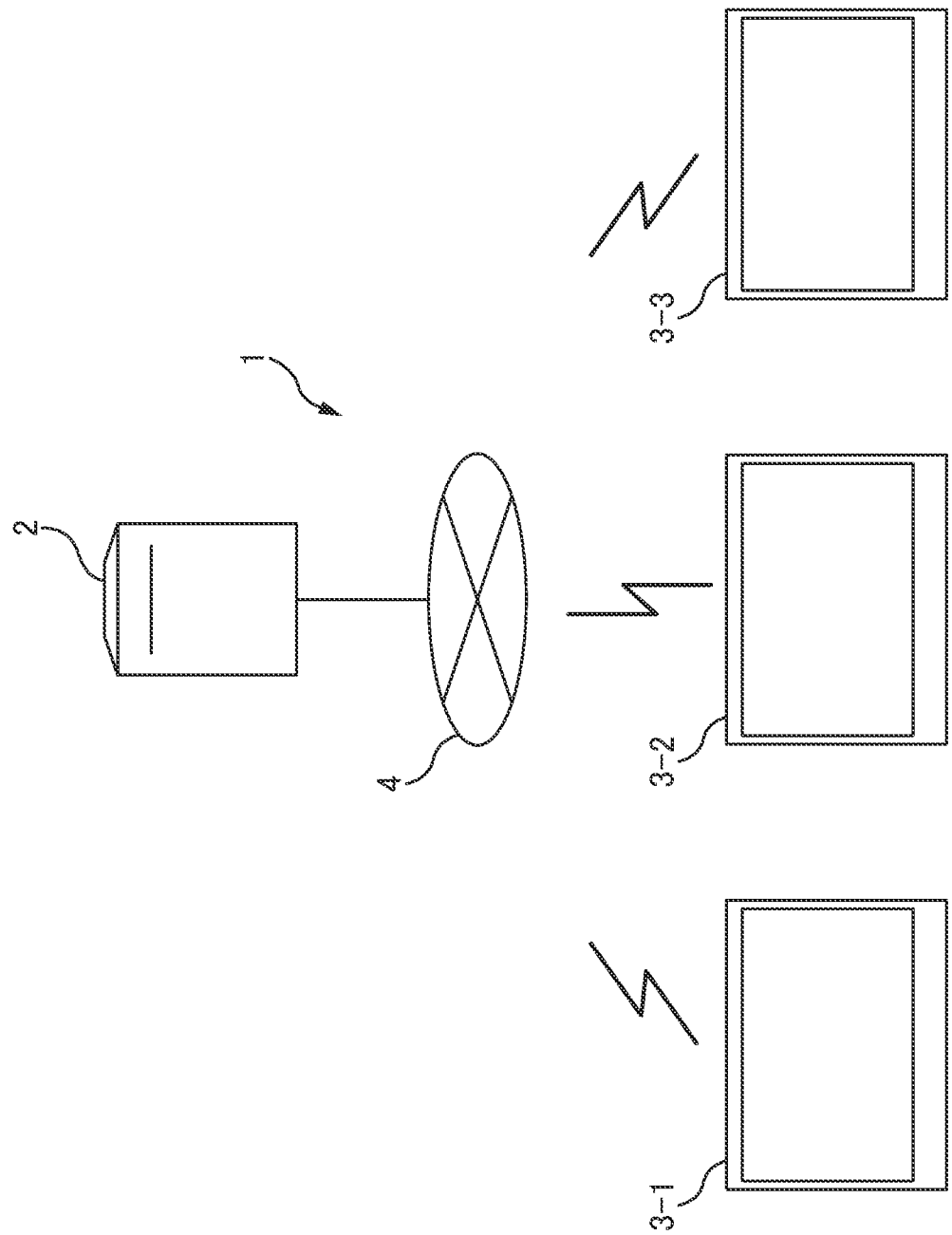
FIG. 29 is a diagram showing a configuration of a network system.

As shown in FIG. 29, a network system 1 includes a server 2, a plurality of terminals 3 (in this example, three terminals 3-1, 3-2, and 3-3) and a communication network 4. The terminals 3-1 to 3-3 can communicate with the server 2 via the network 4. Each of the terminals 31 to 3-3 is a desktop type, laptop type or tablet type computer system. Each of the terminals 3-1 to 3-3 may be a portable computer system or a computer system on a desk. The server 2 is a tower type, desktop type, rack mount type or blade type computer system. The network 4 is a dedicated line network running in a hospital facility, for example, a LAN (Local Area Network) using cables or radio frequencies.

This system 1 is a device that assists creation of contents (hereinafter, referred to as operation flow contents) for expressing a flow of a medical instrument handling operation in order to visually present, to an operator, details of the medical instrument handling operation related to handling of medical instruments. In other words, the editor who has logged in with his own user ID and password can edit a new or existing operation flow content by operating one of the server 2 and the terminals 3-1 to 3-3 of the system 1. In updating the operation flow content, instead of overwriting the file of the operation flow content before the update with the file of the operation flow content after the update, a file of the updated operation flow content is stored as a new edition (version) besides a file of the operation flow content before the update. As a result, the edition (version) of the operation flow content is managed by the system 1. The management of the version of the operation flow content will be described in detail later.

The system 1 is a device that expresses a flow of a medical instrument handling operation based on the edited operation flow content. In other words, by operator's operating one of the server 2 and the terminals 3-1 to 3-3 of the system 1 in a logged-in state with his own user ID and password, the operation flow content is used (in detail, one of files 115 (see FIG. 46) described later is opened), and a flow of a medical instrument handling operation based on the operation flow content is expressed. In using operation flow contents, a use history (by whom and which version of the operation flow content was used) is recorded and accumulated. Recording and accumulation of the use history will be described in detail later.

The medical instrument handling operation as well as a way of use of the system 1 at that time are described first below.

The medical instrument handling operation refers to an operation performed for surgeries in which medical instruments are used. Medical instruments refer to instruments such as endoscopes, ultrasonic probes, pairs of forceps, pairs of scissors, scalpels, scalpel handles, cannulas, tweezers, retractors, scales, Sondes, elevators, raspas, suction tubes, rib spreaders, rib contractors, needle holders, syringes, metal balls, kidney dishes, cups, pins, mirrors, files, opening devices, Klemmes, handpieces, Elevatoriums, chisels, curettes, raspatories, mirrors, suture needles, rongeurs, water receivers, needles, spatulas, bougies, vent tubes, bone impactors, rongeurs, needle-nose pliers, hammers, goniometers, perforators, droppers, metal swabs, enemas, syringes and the like. Combinations of a plurality of instruments (such as surgical kits including pairs of forceps, scalpels, pairs of scissors) are also included in medical instruments.

Figure 30:
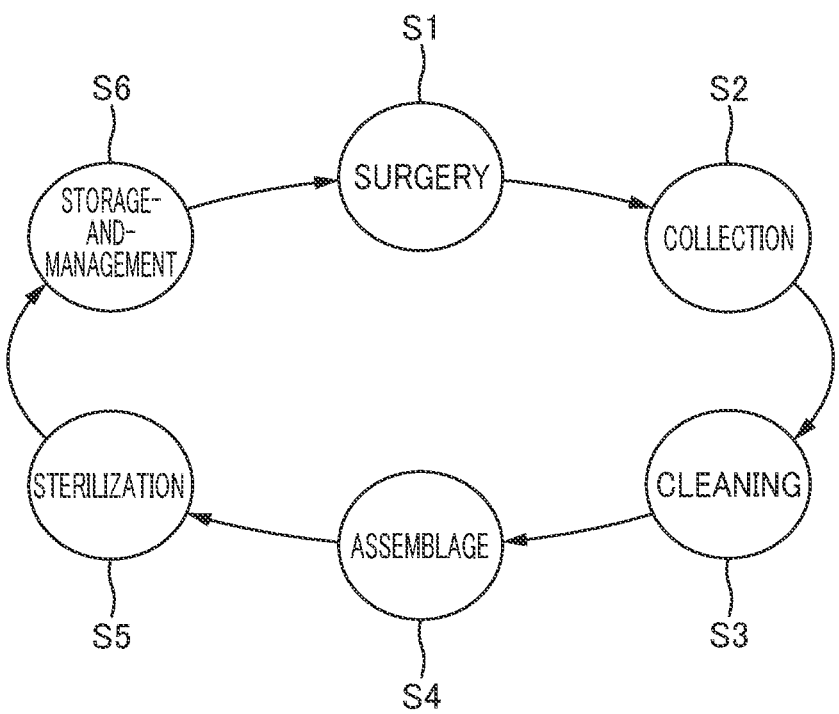
FIG. 30 is a chart showing an operation cycle in which medical instruments are handled.

FIG. 30 is a chart showing an operation cycle in which medical instruments are handled. As shown in FIG. 30, examples of the medical instrument handling operation include a collection operation S2, a cleaning operation S3, an assemblage operation S4, a sterilization operation S5, and a storage-and-management operation S6. Medical instruments are handled in any of the operations S2 to S6.

Specifically, when a physician used a medical instrument during a surgery S1, the medical instrument is collected after the surgery S1 (the collection operation S2). Then, the collected medical instrument is disassembled and cleaned using a cleaning device (the cleaning operation S3). Then, the cleaned medical instrument is assembled (the assemblage operation S4). Then, the assembled medical instrument is subjected to a sterilization (the sterilization operation S5). Then, the sterilized medical instrument is stored for surgery (the storage-and-management operation S6). The stored medical instrument will be used for a surgery S1 again.

The system 1 is used for the medical instrument handling operation such as the collection operation S2, the cleaning operation S3, the assemblage operation S4, the sterilization operation S5, and the storage-and-management operation S6.

Although details are described later, an operation flow content is edited by editor's operating the terminals 3-1 to 3-3 or the server 2 of the system 1 and the edited operation flow content is recorded in the storage of the server 2. The operation flow content recorded in the storage of the server 2 is also synchronized with (recorded on) the storages of the terminals 3-1 to 3-3. Subsequently, by the operator's operating the terminal 3-1 in performing the medical instrument handling operation, a flow and details of the medical instrument handling operation are presented to the terminal 3-1; therefore, the operator can proceed the medical instrument handling operation while looking at the terminal 3-1 to check the details of the operation. Here, the medical instrument handling operation includes one or more upper-level processes at the uppermost level. Each upper-level process includes one or more main processes at a middle-upper level. Each main process includes one or more sub processes at the lowermost level. In other words, each main process represents detailed operations required for completing the operation of the upper-level process having that main process as a component. Detailed operations of the main process are those obtained by segmenting operations of the upper-level process. Each sub process represents detailed operations required for completing the operation of the main process having that sub process as a component. Detailed operations of the sub process are those obtained by segmenting operations of the main process.

Figure 31:
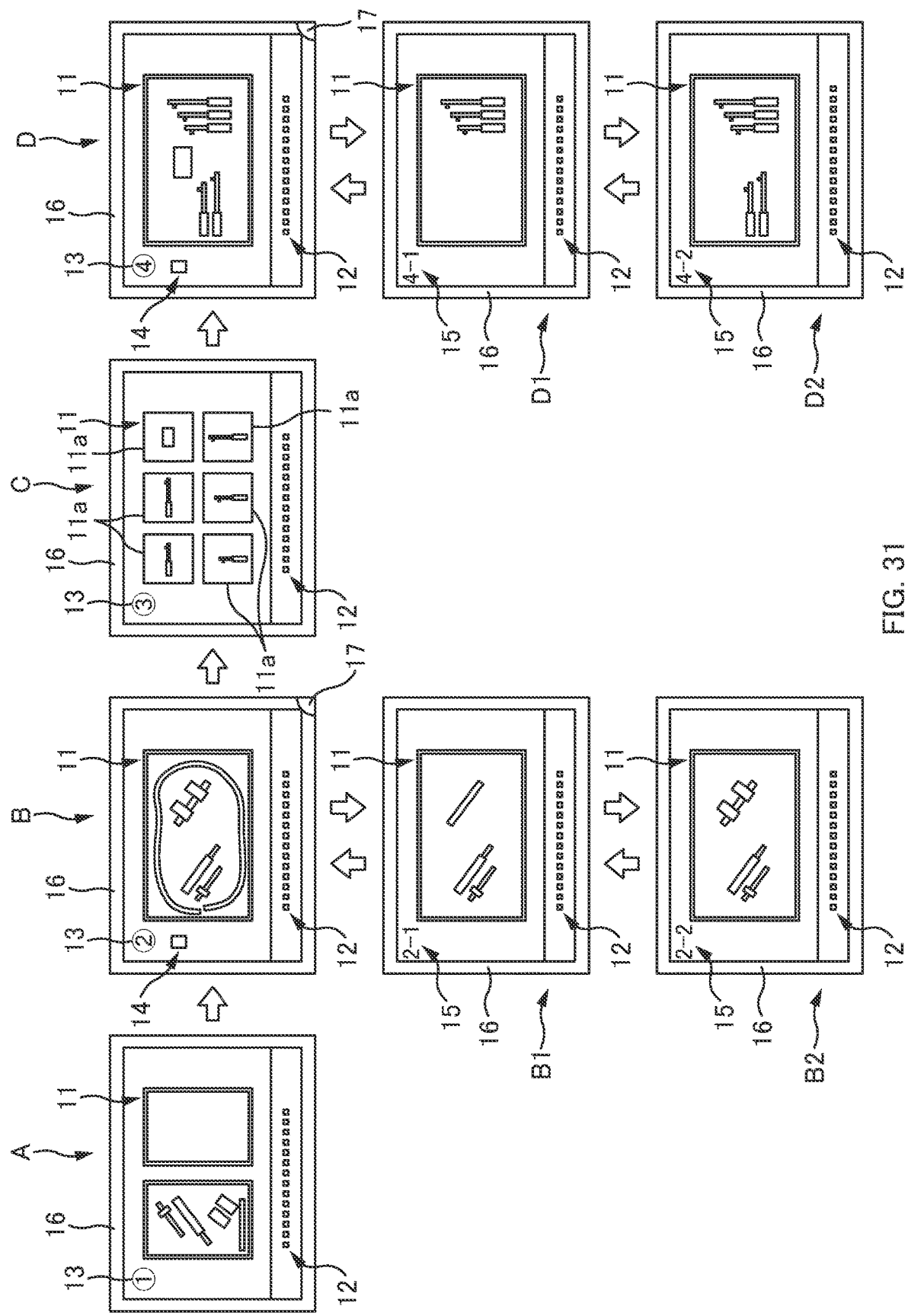
FIG. 31 is an explanatory diagram of a screen transition.

Referring to FIG. 31, a flow and details of the medical instrument handling operation displayed on the terminal 3-1 are described. Here, FIG. 31 is a diagram showing transitions of the screen displayed on the display of the terminal 3-1 (specifically, any of files 115 (see FIG. 46) described later) according to an operation flow content.

When an operator is going to perform a certain upper-level process during a medical instrument handling operation, he selects a certain option (the certain option corresponds to a certain upper-level process) from a plurality of options (options and the upper-level processes correspond to each other one by one) by operating the terminal 3-1 while looking at a process selection screen (option list screen) displayed on the terminal 3-1. Here, the operation is displayed in the form of, for example, a widget (on the widget, an image designated by an image designation data of an upper-level process data 45 described later is displayed), an icon (a thumbnail of an image designated by an image designation data of an upper-level process data 45 described later), a button, or a radio button etc.

Thereafter, when the operator operates the terminal 3-1 (for example, a flick operation, a swipe operation, a tap operation, a multi-tap operation, a scroll operation or a drag operation) as the operation proceeds in a certain upper-level process, the view of the display of the terminal 3-1 changes from a screen A, to a screen B, a screen C, and then a screen D in this order. The screens A to D are associated with main processes of a certain upper-level process in the medical instrument handling operation. More specifically, they are for displaying details of the operation in each main process and the state of the medical instrument(s) for this operation. Furthermore, on the screens A to D, information (for example, a name of an operation of an upper-level process and an outline of an operation of an upper-level process) for specifying the upper-level process including the processes associated with the screens A to D is displayed. The number of the main processes of the certain upper-level process in the medical instrument handling operation is not limited to four, and the number of the screens related to the main processes is equal to the number of the main processes.

Further, when the operator operates the terminal 3-1 while the screen B is being displayed on the display of the terminal 3-1, the view of the display of the terminal 3-1 changes from the screen B to a screen B1. Moreover, by the operator's operating the terminal 3-1, the view of the display of the terminal 3-1 changes from the screen B1 to a screen B2, from the screen B2 to the screen B1, from the screen B1 to the screen B. The screens B1 and B2 are associated with sub processes (detailed processes) of the main process associated with the screen B. More specifically, they are for displaying details of the operation in each sub process and the state of the medical instrument(s) for this operation.

Similarly, when the screen D is displayed on the display of the terminal 3-1, transitions occur from the screen D to a screen D1 and from the screen D1 to a screen D2 by the operation of the terminal 3-1 by the operator. The screens D1 and D2 are associated with sub processes of the main process related to the screen D. More specifically, they are for displaying details of the operation in each sub process and the state of the medical instrument(s) for this operation. It should be noted that the number of sub processes of each main process associated with the screens B and D is not limited to two, and the number of screens associated with the sub processes is equal to the number of sub processes.

The main process is classified as different types: a normal operation process, a quality important operation process, or a count operation process. In the screens A to D, one can understand which type each main process belongs to. For example, a process classification display 16 is displayed in the periphery of each of the screens A to D and the color of the process classification display 16 indicates the type of the main process. For example, because the main process associated with the screen A is the normal operation process, the process classification display 16 of the screen A is drawn in blue. Because the main processes associated with the screens B and D are the quality important operation process, the process classification display 16 of the screen C is drawn in red. Because the main process associated with the screen C is the count operation process, the process classification display 16 of the screen C is drawn in red. On the other hand, the kind of the sub processes is only the normal operation process. However, it is possible to visually determine which of the main process and the sub process the displayed screen is associated with, because the color of the process classification display 16 used in the case of the sub process (e.g., green) and the color of the process classification display 16 used when the main process is the normal operation process (e.g., blue) are different from each other.

An instrument display 11 and an operation detail display 12 are displayed on any of the screens A to D, B1, B2, D1, and D2. On the operation detail display 12, details of the operation of that process are displayed with a text. On the instrument display 11, the state of the medical instrument(s) for the operation of that process is displayed with an image.

On the screens A to D, an order display 13 indicating the page number or the main process order is displayed. The page number represents the display order of the screens A to D in ascending order with respect to the screen A as a reference. The main process order represents the order of the main processes of each of the screens A to D in ascending order with respect to the main process related to the screen A. The number of pages and the main process order may be represented by numerals (text), or may be represented by, for example, a symbol, a mark, a pattern, or an indicator.

On the screen B, a tag display 14 indicating a tag is displayed. The tag (for example, a text "detail" or "CHECK") displayed on the tag display 14 indicates that the main process associated with the screen B has a sub process. Since the main process associated with the screen C has a sub process, a tag display 14 is also displayed on the screen D. Since the main processes associated with the screens A and C have no sub process, no tag display is displayed on the screens A and C.

On the screens B1, B2, D1, and D2, an order display indicating a sub process order is displayed. The sub process order represents the order of sub processes of the main process in ascending order. The sub process order may be represented by a number (text), or may be represented by, for example, a symbol, a mark, a pattern, or an indicator.

When the screen A is being displayed, the operator can check the details of the operation of the process by viewing the operation detail display 12 of the screen A. In addition, by viewing the instrument display 11 of the screen A, he can compare the actual medical instrument handled and images of medical instruments on the instrument display 11, whereby it is possible to check whether the operation of that process has proceeded accurately. In other words, if the state of the actual medical instrument handled is about the same as the medical instrument image on the instrument display 11, it can be recognized that the operation in that process is accurate, and if the state of the actual medical instrument is different from the medical instrument image on the instrument display 11, it can be recognized that the operation in that process is inaccurate.

By the operator's operating the terminal 3-1 as the medical instrument handling operation proceeds, the view of the display of the terminal 3-1 changes from the screen A to the screen B, the screen C, and then to the screen D in this order. Therefore, the operator can visually recognize details of the operation and the accuracy of the operation in each process.

The main processes associated with the screens B and D are quality important operation processes. The operations for changing the screens B and D of the quality important operation process to the subsequent screen is different from the operations for changing the screens of the normal operation process and the count operation process to their subsequent screens. That is, a confirmation button 17 is displayed at the lower right of the screens B and D, and the screen turns to a next screen when an operation (for example, single click, double click, tap, double tap, and long press) of selecting and determining the confirmation button 17 is performed. If this operation of selecting and determining the confirmation button 17 is not performed, no next screen is displayed. Thus, the quality of the quality important operation is guaranteed by making an operator do careful operations and checking. When an operation of selecting and determining the confirmation button 17 is performed after the display of the screen D, the screen of the terminal 3-1 returns to the process selection screen or turns to a screen related to a subsequent upper-level process. The screen transition of the terminal 3-1 is performed in a similar manner when the operator operates the terminal 3-1 as the next upper-level process proceeds.

The main process associated with the screen C is the count operation process, but the operation for changing the screen C to a next screen of the count operation process is different from operations for changing the screens of the normal operation process and the quality important operation process to their subsequent screens. Specifically, a plurality of widgets 11a are displayed on the instrument display 11 of the screen C and images of components of a medical instrument are displayed on these widgets 11a. The operator operates the terminal 3-1 while comparing components of an actual medical instrument with the widgets 11a. Specifically, if the components displayed on the widgets 11a are included in the actual medical instrument, the operator selects that widget 11a by operating the terminal 3-1. In this way, after all the widgets 11*a* are selected, the screen C is turned to a next screen. Accordingly, with the screen C is displayed, the screen C does not turn to any subsequent screens unless operations of checking the presence or absence of the actual components of the medical instrument and operations of counting these components has been completed. This forces the operator to perform such operations.

It should be noted that when the operator performs another upper-level process in the medical instrument handling operation, the screen of the terminal 3-1 will shift in a similar manner by operating the terminal 3-1 as the operation of the upper-level process proceeds.

An editor edits, by using the terminals 3-1 to 3-3 or the server 2 of the system 1, an operation flow content for achieving screen transitions as mentioned above. The terminal 3-1 is described in detail below under the assumption that an operation flow content is edited using the terminal 3-1.

Figure 32:
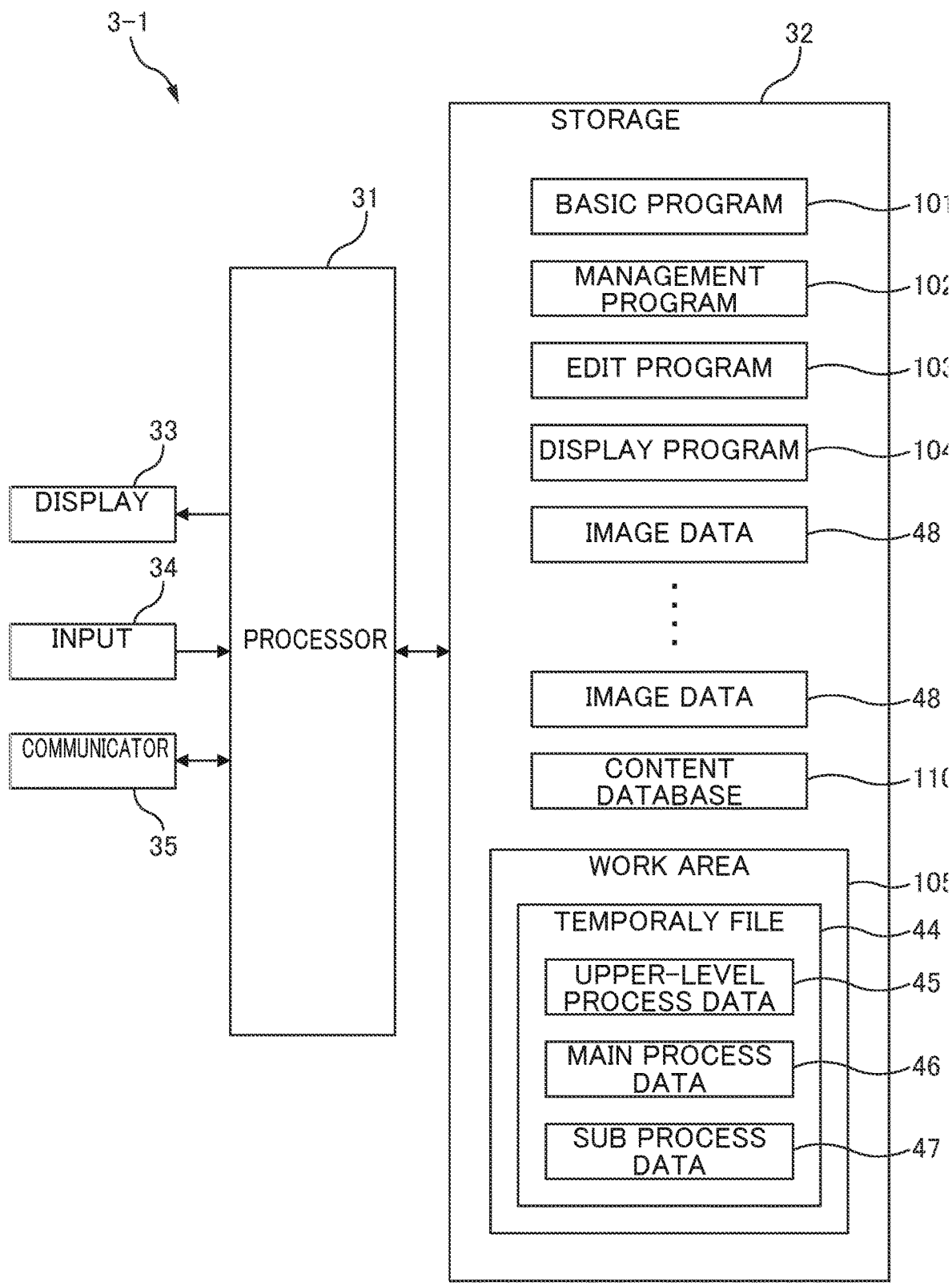
FIG. 32 is a block diagram of a terminal as a management device.

As shown in FIG. 32, this terminal 3-1 includes, as hardware, a processor 31, a storage 32, a display 33, an input 34, and a communicator 35.

The processor 31 is a computer having a CPU, a GPU, a ROM, a RAM, a bus, a hardware interface, and the like. The storage 32 is a storage including a semiconductor memory, a hard disk drive, and the like that is readable and writable by the processor 31. The display 33 is a display that performs screen display. The input 34 is an input such as a touch panel, a switch, a keyboard, and a pointing device. The communicator 35 is a network adapter (for example, a network interface card, a wireless LAN slave).

In the storage 32, image data 48 that become materials of operation flow contents are recorded. The image data 48 are images having a medical instrument shown therein to indicate a state of the medical instrument due to operations in each process. The image data 48 have their unique data (e.g., a file name or an identifier) and each image data 48 can be distinguished from other image data 48 according to the unique data.

The image data 48 is recorded in advance in the storage 32 for each type, state, component, combination, etc. of a medical instrument. Every time a medical instrument is introduced (transferred, purchased, stocked, lent) to a hospital, image data obtained by photographing the medical instrument and its components using an electronic camera are stored in a database of a storage of the server 2 and the image data thereof are also synchronized with (recorded on) the storage 32 as the image data 48.

A basic program 101, a management program 102, an edit program 103, and a display program 104 are stored in the storage 32.

The basic program 101 is for achieving an OS (Operating System), a GUI (Graphical User Interface) of the OS, and user management. By starting and executing the basic program 101 by the processor 31, the storage 32, the display 33, the input 34, among them.

The display program 104 has been installed on the OS of the basic program 101 and can be executed by the processor 31 on the OS. The processor 31 reads the operation flow content (specifically, any of files 115 described later (see FIG. 46)) by the display program 104 being started and executed by the processor 31, and the processor 31 controls the display 33 so that transition of the screens (e.g., the screens A to D, B1, B2, D1, and D2) according to the operation flow content will proceed according to how the input 34 was operated by the operator. Here, in displaying each of the screens to be changed, the processor 31 determines views of the instrument display 11, the operation detail display 12, the order display 13, the tag display 14, the order display 15, and the process classification display 16 according to the operation flow content (specifically, any of the files 115 described later (see FIG. 46)) and generates each screen by rendering these views. The screens A to D, B1, B2, D1, and D2 that are examples of the transition of the screen are as described above.

The edit program 103 has been installed on the OS of the basic program 101 and can be executed by the processor 31 on the OS. The GUI is operated by the input 34 by the edit program 103 being started and executed by the processor 31 and the GUI is displayed on the display 33. That is, when the editor operates the input 34 with the edit program 103 activated by the processor 31, the operation flow content is edited by the processor 31 according to the operation details. At this time, the operation flow content being edited has been developed in a work area (a temporary folder) 105 of the storage 32 as a temporary file 44 and is updated and recorded in the work area 105 whenever it is edited by the processor 31. It should be noted that the work area 105 may be generated in the RAM of the processor 31 and the data of the temporary file 44 may be developed in the work area 105 in the RAM.

The temporary file 44 includes an upper-level process data 45 for each upper-level process, a main process data 46 for each main process, and a sub process data 47 for each sub process. As will be described in detail later, when registering the operation flow content, the temporary file 44 being edited in the work area 105 is copied to and registered in a contents database 110 of the storage 32 as a file 115 (see FIG. 46). Accordingly, similar to the temporary file 44, the file 115 includes an upper-level process data, a main process data, and a sub process data.

FIG. 33 is a diagram showing a data configuration of the upper-level process data 45. The upper-level process data includes an upper-level process order data, an operation name data, and an image designation data. The upper-level process order data represents the order of the upper-level process. The operation name data is a text data representing an operation name that briefly and simply shows details of the operation of the upper-level process. The image designation data is for designating a particular image data 48 from the plurality of image data 48. More specifically, it is a unique data (e.g., a file name or an identifier) of a particular image data 48. As described above, in the process selection screen, images designated by the image designation data of the upper-level process data 45 is displayed.

FIG. 34 is a diagram showing a data configuration of the main process data 46. The main process data 46 has an upper-level process order data, a main process order data, an operation detail data, a classification data, an image designation data, and a sub process presence/absence data.

The upper-level process order data represents the order of the upper-level process to which the main process belongs. The main process data 46 and the upper-level process data 45 having the same value of the upper-level process order data are associated with each other.

The main process order data represents the order of the main process. In displaying each of the screens A to D based on one of the files 115, the main process order data of that file 115 is referred to by the processor 31 and a view of the order display 13 is determined by the processor 31 according to the main process order data and the order of displaying the screens A to D is determined by the processor 31.

The operation detail data is a text data representing details of the operation of the main process. In displaying each of the screens A to D based on one of the files 115, the operation detail data of that file 115 is referred to by the processor 31 and a view of the operation detail display 12 is determined by the processor 31 according to the operation detail data.

The classification data represents a type of the main process. Values of the classification data are a "normal operation," a "quality important operation," and a "count operation." Which one of the normal operation process, the quality important operation process, and the count operation process the main process is classified can be understood based on the classification data. In displaying each of the screens A to D based on one of the files 115, the classification data of that file 115 is referred to by the processor 31 and the color of the process classification display 16 is determined by the processor 31 according to the classification data.

The image designation data is for designating a particular image data 48 from the plurality of image data 48. More specifically, it represents a unique data (e.g., a file name or an identifier) of a particular image data 48. In displaying each of the screens A to D based on one of the files 115, the image designation data of that file 115 is referred to by the processor 31, the image data 48 designated according to the image designation data is read by the processor 31, and that image is displayed on the instrument display 11 by the processor 31.

The sub process presence/absence data represents whether a main process has a sub process or not. In displaying each of the screens A to D based on one of the files 115, the sub process presence/absence data of that file 115 is referred to by the processor 31 and whether a tag of the tag display 14 is to be displayed or not is determined by the processor 31. In addition, when an editor operates the input 34, the sub process presence/absence data of that file 115 is referred to by the processor 31 and whether the screens A to D of the main process are to be changed to the screens B1 and D1 is determined by the processor 31.

FIG. 35 is a diagram showing a data configuration of the sub process data 47. Each sub process data 47 has an upper-level process order data, a main process order data, a sub process order data, an operation detail data, and an image designation data.

The upper-level process order data represents the order of the upper-level process to which the sub process belongs. The sub process data 47 and the upper-level process data 45 having the same value of the upper-level process order data are associated with each other.

The main process order data represents the order of the main process to which the sub process belongs. The sub process data 47 and the main process data 46 having the same value of the main process order data are associated with each other. The sub process order data represents the order of the sub process. In displaying each of the screens A to D, B1, B2, D1, and D2 based on one of the files, transitions of the screens B to B1, the screens B1 to B2, the screens D to D1, and the screens D1 to D2 are performed based on the main process order data and the sub process order data of that file 115. In addition, the main process order data and the sub process order of that file 115 are referred to by the processor 31, and a view of the order display 15 of each of the screens B1, B2, D1, and D2 is determined by the processor 31 according to the main process order data and the sub process order.

The operation detail data is a text data representing details of the operation of the sub process. In displaying each of the screens B1, B2, D1, and D2 based on one of the files 115, the operation detail data of that file 115 is referred to by the processor 31 and a view of the operation detail display 12 is determined by the processor 31 according to the operation detail data.

The image designation data is for designating a particular image data 48 from the plurality of image data 48. More specifically, it is a unique data (e.g., a file name or an identifier) of a particular image data 48. In displaying each of the screens B1, B2, D1, and D2 based on the one of the files 115, the image designation data of that file 115 is referred to by the processor 31, the image data 48 designated according to the image designation data is read by the processor 31, and that image is displayed on the instrument display 11.

Figure 36:
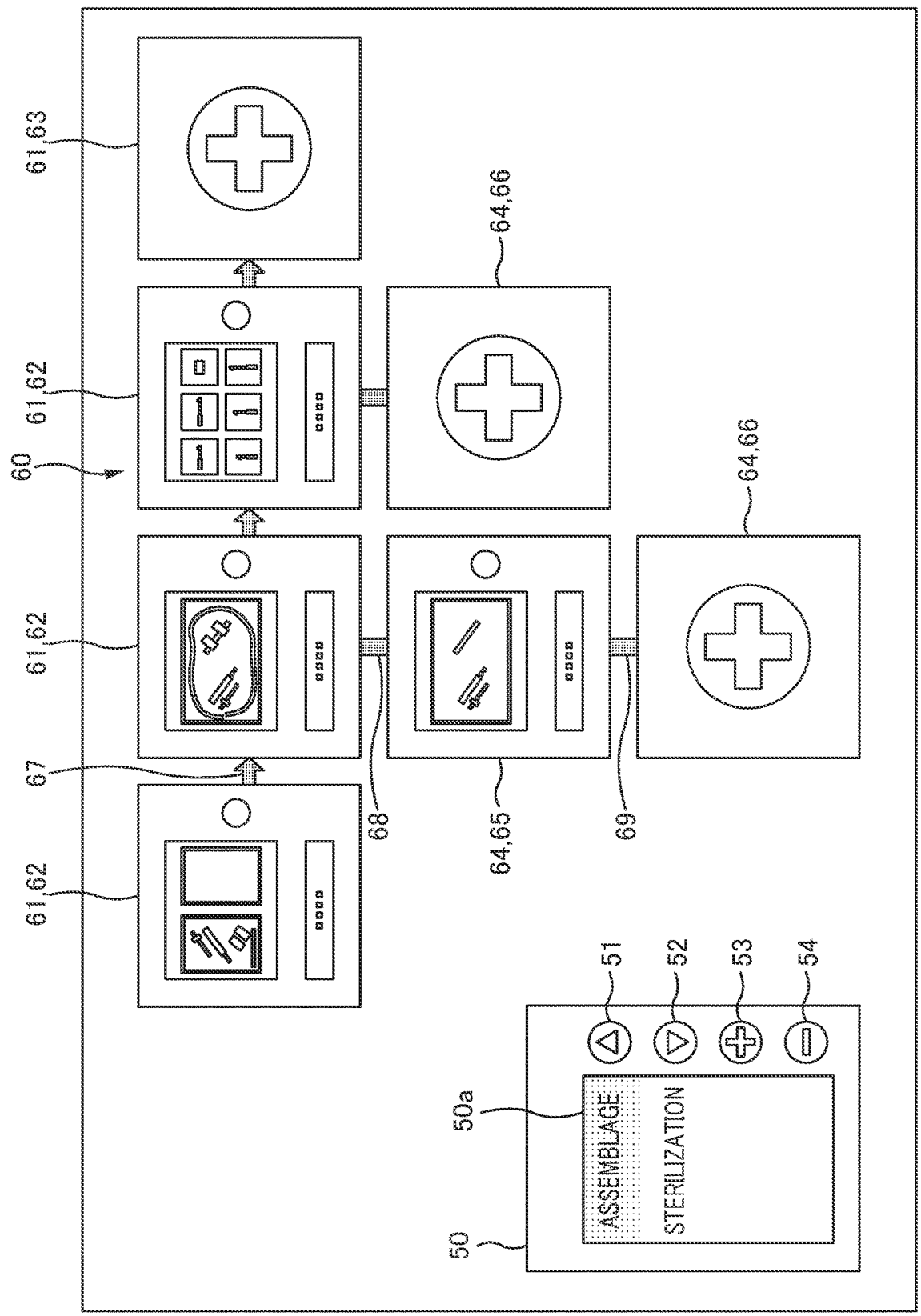
FIG. 36 a diagram showing an operation flow edit screen displayed on a display of a terminal.

FIG. 36 is an example of an operation flow edit screen displayed on the display 33. The operation flow edit screen shown in FIG. 36 is a GUI achieved when the processor 31 controls the display 33 according to the edit program 103. Accordingly, when an editor operates the input 34, the operation flow edit screen is operated by the processor 31 according to how it was operated.

The operation flow edit screen shown in FIG. 36 is for creating the orders and details of the operation of the main process and sub process belonging to a certain upper-level process. That is, under the assumption that the operation flow edit screen is a page, an operation flow edit screen is displayed for each upper-level process.

Here, the processor 31 generates an operation flow edit screen according to the edit program 103, and supplies a video signal according to the operation flow edit screen to the display 33. Upon generating the operation flow edit screen, the processor 31 arranges the page manipulation widget 50 and the process widgets 61 and 64 on the operation flow edit screen and combines the page manipulation widget 50 and the process widgets 61 and 64 with the operation flow edit screen. Therefore, the page manipulation widget 50 is displayed on the left side of the operation flow edit screen displayed on the display 33, and the process widgets 61 and 64 representing the main and sub processes, respectively, belonging to an upper-level process of the medical instrument handling operation are displayed in an array arrangement in an area 60 on the right side of the page manipulation widget 50.

Each widget 61 displayed at the uppermost row of the operation flow edit screen is a main process widget representing each main process belonging to an upper-level process of the medical instrument handling operation and the other widgets, i.e., the widgets 64 are sub process widgets each representing a sub process belonging to the upper-level process of the medical instrument handling operation. These main process widgets 61 are arranged in a line in the lateral direction from the left to the right in the order of the main processes. When there are sub processes of the main process, the sub process widget 64 representing each sub process of the main process is arranged vertically from the top to the bottom of the screen under the main process widget 61 in the order of the sub processes.

A link mark 67 is displayed between the left and right sides of the adjacent main process widgets 61. The link mark 67 indicates that the main process is followed by the next main process.

When there are sub processes of the main process, a link mark 68 is displayed between the main process widget 61 and the sub process widget 64 on the lower side thereof. The link mark 68 indicates that the main process represented by the main process widget 61 on its upper side includes sub processes.

A link mark 69 is displayed between the upper and lower sides of the adjacent sub process widgets 64. The link mark 69 indicates that the sub process is followed by the next sub process.

Depending on the data of the temporary file 44, the area 60 of the operation flow edit screen may be blank (a state in which the process widgets 61 and 64 and the link marks 67 to 69 are not displayed) in some cases.

Each main process widget 61 is associated with the main process data 46 on a one-to-one basis, and the association between the main process widget 61 and the main process data 46 is achieved by the main process order data. In other words, when generating and displaying the operation flow edit screen, the processor 31 refers to the main process order data of the main process data 46 to determine, based on the main process order data, a position where the main process widget 61 is displayed in the operation flow edit screen. Therefore, the main process order data of the main process data 46 represents the position where the main process widget 61 associated with the main process data 46 is displayed (the place from the left of the screen).

When the main process data 46 is generated in the storage 32 by the processor 31, the processor 31 performs processing in such a way as adding the main process widget 61 to the operation flow edit screen. On the contrary, when the main process data 46 is deleted from the storage 32 by the processor 31, the processor 31 performs processing in such a way as deleting the main process widget 61 associated with the main process data 46 from the operation flow edit screen. The addition and deletion of the main process widget 61 will be described in detail later.

Each sub process widget 64 is associated with the sub process data 47 on a one-to-one basis, and the association between the sub process widget 64 and the sub process data 47 is achieved by the main process order data and the sub process order data. In other words, when generating and displaying the operation flow edit screen, the processor 31 refers to the main process order data and the sub process order data of the sub process data 47 to determine a position where the sub process widget 64 is displayed in the operation flow edit screen. Therefore, the main process order data and the sub process order data of the sub process data 47 represent the position where the sub process widget 64 associated with the sub process data 47 is displayed (the main process order data represents the place from the left of the screen and the sub process order data represents the place from the top of the screen).

Further, when the sub process data 47 is generated in the storage 32 by the processor 31, the processor 31 performs processing in such a way as adding the sub process widget 64 to the operation flow edit screen. On the contrary, when the sub process data 47 is deleted from the storage 32 by the processor 31, the processor 31 performs processing in such a way as deleting the sub process widget 64 associated with the sub process data 47 from the operation flow edit screen. The addition and deletion of the sub process widget 64 will be described in detail later.

Figure 37:
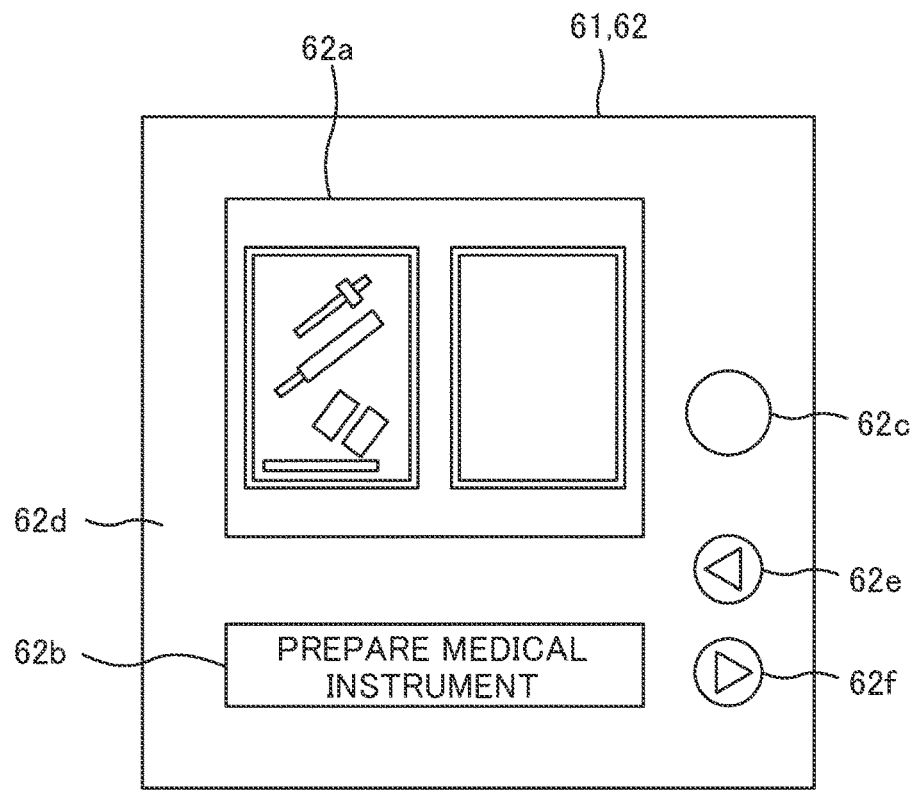
FIG. 37 is a diagram showing a registered widget of a main process displayed on the operation flow edit screen.
Figure 38:
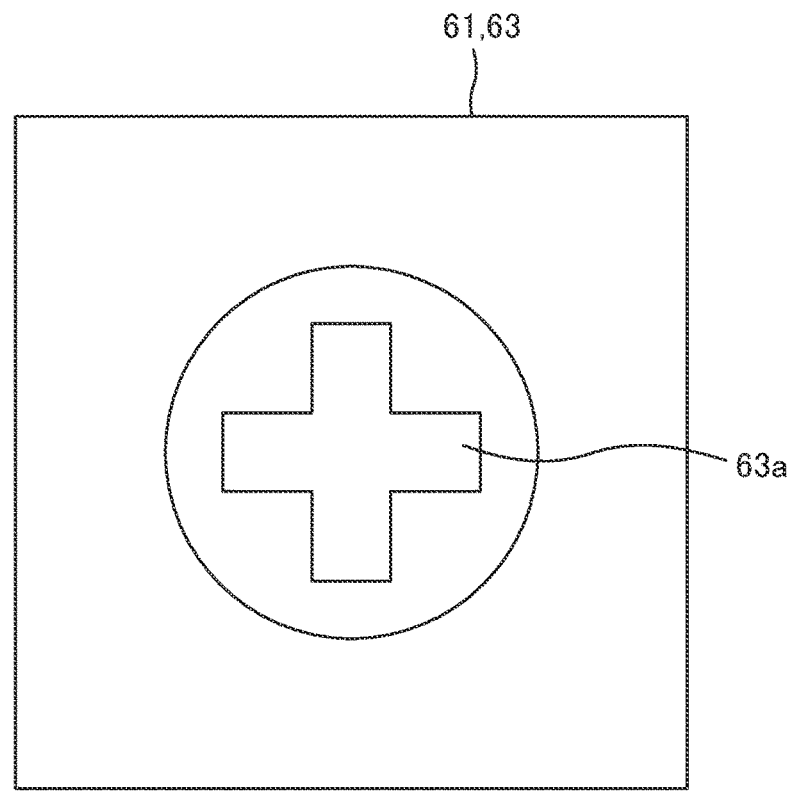
FIG. 38 is a diagram showing an unregistered widget of a main process displayed on the operation flow edit screen.

Each of the main process widgets 61 is classified as an operation registered widget 62 (hereinafter referred to as the registered widget 62) as shown in FIG. 37 and an operation unregistered widget 63 (hereinafter referred to as the unregistered widget 63) as shown in FIG. 38. The registered widget 62 indicates that an operation detail data, a classification data, and an image designation data have been registered in the main process data 46 associated with that registered widget 62 (the main process widget 61). The unregistered widget 63 indicates that a main process order data and an operation name data have been registered in the main process data 46 associated with that unregistered widget 63 (the main process widget 61), but an operation detail data, a classification data, and an image designation data have not yet been registered.

Figure 39:
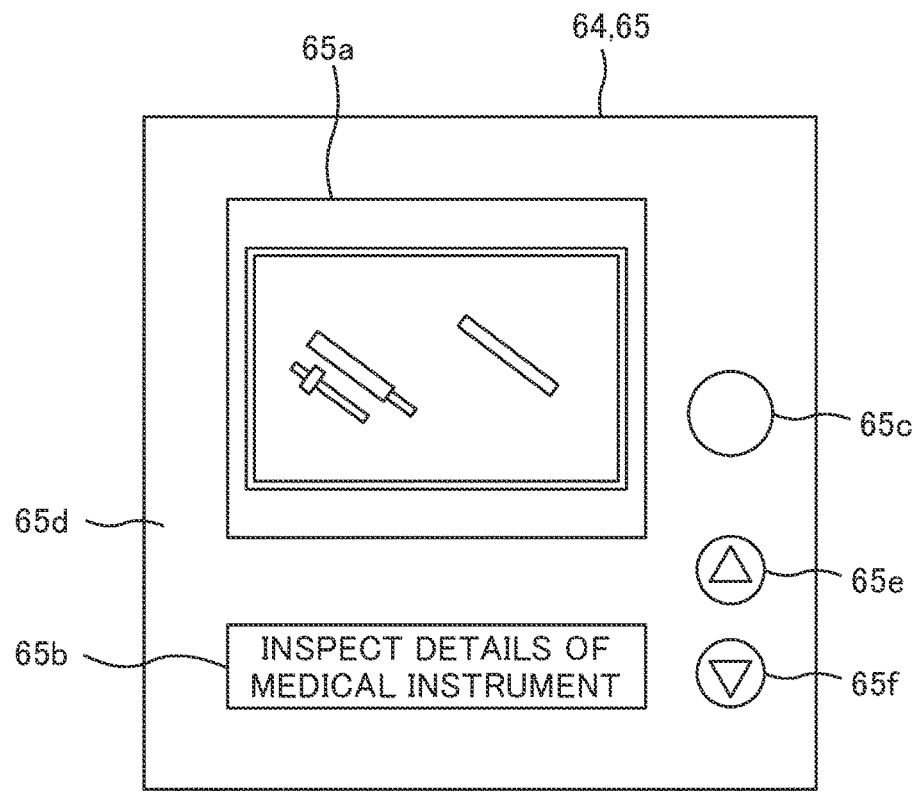
FIG. 39 is a diagram showing a registered widget of a sub process displayed on the operation flow edit screen.
Figure 40:
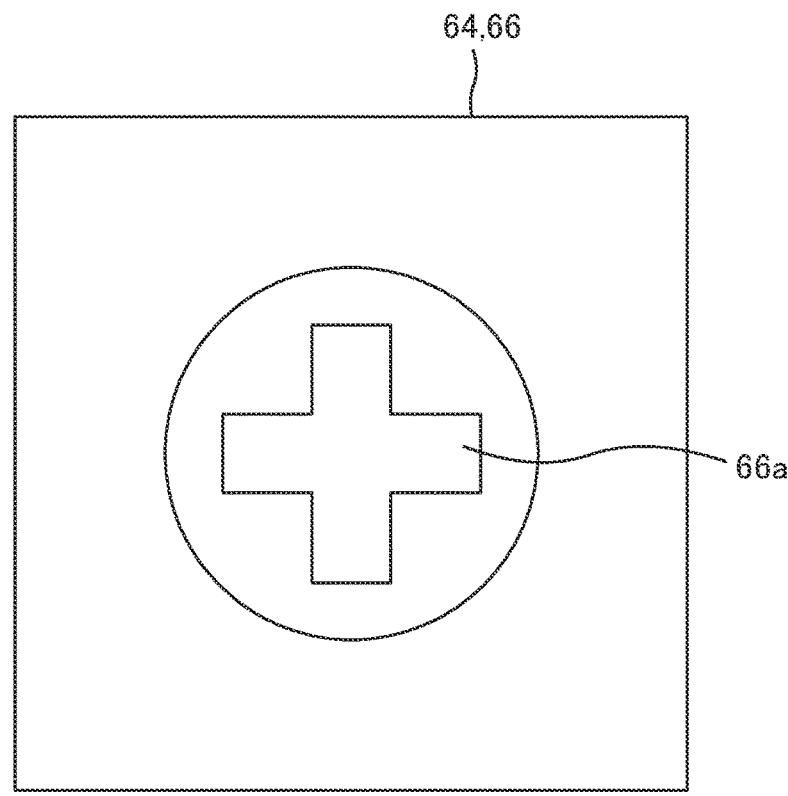
FIG. 40 is a diagram showing an unregistered widget of a sub process displayed on the operation flow edit screen.

Each of the sub process widgets 64 is also classified as an operation registered widget 65 (hereinafter referred to as the registered widget 65) as shown in FIG. 39 and an operation unregistered widget 63 (hereinafter referred to as the operation unregistered widget 63) as shown in FIG. 40. The registered widget 65 indicates that an operation detail data and an image designation data have been registered in the sub process data 47 associated with that registered widget 65 (the sub process widget 64). The unregistered widget 66 indicates that a main process order data and a sub process order data have been registered in the sub process data 47 associated with that unregistered widget 66 (the sub process widget 64), but an operation detail data and an image designation data have not yet been registered.

In the unregistered widgets 63 and 66, buttons 63a and 66a are displayed.

In the registered widgets 62 and 65, instrument displays 62a and 65a, operation detail displays 62b and 65b, edit buttons 62c and 65c, raising buttons 62e and 65e, and lowering buttons 62f and 65f are displayed.

An image of the image data 48 designated by the image designation data of the main process data 46 associated with the registered widget 62 (the main process widget 61) is displayed on the instrument display 62a. The content of the operation detail data of the main process data 46 associated with the registered widget 62 (the main process widget 61) is displayed on the operation detail display 62b as a text. That is, in generating and displaying the operation flow edit screen, the processor 31 refers to the operation detail data and the image designation data of the main process data 46 and determines a display image of the instrument display 62a and a display text of the operation detail display 62b based on the operation detail data and the image designation data.

An image of the image data 48 designated by the image designation data of the sub process data 47 associated with the registered widget 65 (the sub process widget 64) is displayed on the instrument display 65a. The content of the operation detail data of the sub process data 47 associated with the registered widget 65 (the sub process widget 64) is displayed on the operation detail display 65b as a text. That is, in generating and displaying the operation flow edit screen, the processor 31 refers to the operation detail data and the image designation data of the sub process data 47 and determines a display image of the instrument display 65a and a display text of the operation detail display 65b based on the operation detail data and the image designation data.

The registered widget 62 is classified as a normal operation process widget representing a normal operation process (detailed operation process), a quality important operation process widget representing a quality important operation process, and a count operation process widget representing a count operation process. Such classification is achieved by the classification data of the main process data associated with the registered widget 62. That is, the classification data of the main process data 46 represents the type of the registered widget 62 associated with the main process data 46. Then, the normal operation process widget, the quality important operation process widget and the count operation process widget are visually distinguishably displayed. That is, in generating and displaying the operation flow edit screen, the processor 31 refers to the classification data of the main process data 46 and determines the color of a background 62d of the registered widget 62 in the operation flow edit screen based on the classification data. For example, the background 62d of the registered widget 62 classified as a normal operation process widget is drawn in blue, and the backgrounds 62d of the registered widgets 62 classified as the quality important operation process widget and the count operation process widget are drawn in red. It should be noted that a background 65d of the registered widget 65 (the sub process widget 64) is drawn in green, and the registered widget 65 and the registered widget 62 can be visually distinguished from each other.

As shown in FIG. 36, a list box 50a, a back button 51, a forward button 52, an add button 53, and a delete button 54 are displayed in the page manipulation widget 50. In the list box 50a, the contents of the operation name data of each of the upper-level process data 45 are displayed as a list (choice) in order, from the top, according to the order of the upper-level process.

Those selected from the list displayed in the list box 50a and those not selected are displayed so as to be visually distinguishable. For example, the selected list is displayed with a hatching, and the unselected list is displayed without hatching. The view of the area 60 of the operation flow edit screen is determined based on the main process data 46 and the sub process data 45 with their respective upper-level process order data identical to that of the upper-level process data 45 corresponding to the selected list.

The back button 51 and the forward button 52 are for changing the selection in the list box 50a. That is, when the back button 51 is selected and determined by the processor 31 according to an operation of the input 34 by the editor, the selection (e.g., a hatching) is changed to one list above by the processor 31 and a view of the area 60 of the operation flow edit screen is changed based on the main process data 46 and the sub process data 45 with their respective upper-level process order data identical to that of the upper-level process data 45 corresponding to the selected list after the change. On the other hand, when the forward button 52 is selected and determined by the processor 31 according to how the input 34 was operated by the editor, the selection (e.g., a hatching) is changed to one list below by the processor 31 and a view of the area 60 of the operation flow edit screen is changed based on the main process data 46 and the sub process data 45 with their respective upper-level process order data identical to that of the upper-level process data 45 corresponding to the selected list after the change.

The add button 53 of the page manipulation widget 50 is for adding a list to the list box 50a and newly generating the upper-level process data 45. That is, when an editor selects one of the lists in the list boxes 50a by operating the input 34, the upper-level process data 45 corresponding to the selected list is selected by the processor 31. Thereafter, when the editor selects and determines the add button 53 by operating the input 34, an operation name select screen or an operation name input screen is displayed. On the screen, when the editor enters or selects an operation name by operating the input 34, a new upper-level process data 45 is generated in the storage 32 by the processor 31. Furthermore, returning to the operation flow edit screen, a list is added immediately below the selection list in the list box 50a, and one registered widget 62 (the main process widget 61) is displayed in the area 60 of the operation flow edit screen.

Here, in the list added to the list box 50a, an operation name that has been selected or entered on the operation name select screen or the operation name input screen is displayed. In a newly created upper-level process data 45, the operation name that has been selected or entered on the operation name select screen or the operation name input screen is registered as an operation name data. Furthermore, a value obtained by adding 1 to the value of the upper-level process order data of the selected upper-level process data 45 is registered in the upper-level process order data of the newly created upper-level process data 45. Moreover, 1 is added to values of the upper-level process order data of the upper-level process data 45 after the selected upper-level process data 45 (one having a larger value than the upper-level process order data of the selected upper process data 45) and the upper-level process order data of the main process data 46 and the sub process data 47 associated therewith, which are updated.

The delete button 54 of the page manipulation widget 50 is for deleting one list from the list box 50a and deleting one upper-level process data 45 and the main process data 46 and the sub process data 47 associated therewith from the storage 32.

Specifically, when an editor selects a certain list in the list box 50a by operating the input 34, the upper-level process data 45 corresponding to the selected list is selected by the processor 31. Thereafter, the editor selects and determines the delete button 54 by operating the input 34. Then, the selected upper-level process data 45 and the main process data 46 and the sub process data 47 associated therewith are deleted from the storage 32 by the processor 31. In addition, 1 is subtracted from values of the upper-level process data 45 after the deleted upper-level process data 45 (one having a larger value than the upper-level process order data of the deleted upper-level process data 45) and the main process data 46 and the sub process data 47 associated therewith, which are updated. Furthermore, a selection list in the list box 50a is deleted, and the view of the area 60 of the operation flow creation screen is changed based on the main process data 46 and the sub process data 45 with their respective upper-level process order data identical to that of the upper-level process data 45 immediately prior to or after the deleted upper-level process data 45.

As described above, each of the main process widgets 61 is classified as the registered widget 62 (see FIG. 37) and the unregistered widget 63 (FIG. 38). The main process widget can be changed from the unregistered widget 63 to the registered widget 62. Hereinafter, a process of changing the display of the main process widget 61 from the unregistered widget 63 to the registered widget 62 is described in detail.

Figure 41:
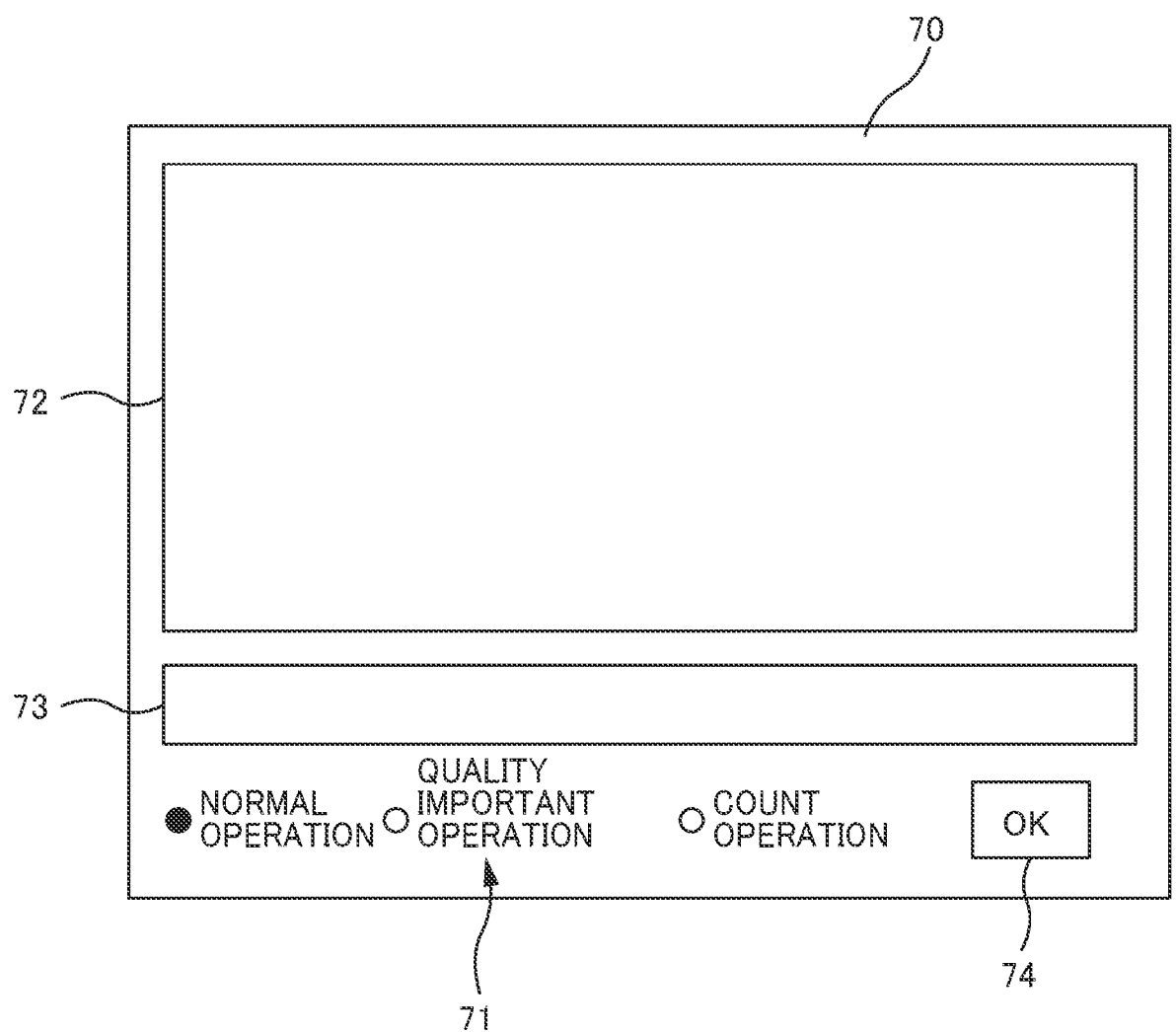
FIG. 41 is a diagram showing a data registration widget displayed on the operation flow edit screen.

When the unregistered widget 63 (in particular, a button 63a) is selected and determined by the processor 31 according to how the input 34 was operated by the editor, a data registration widget 70 as shown in FIG. 41 is additionally displayed on the operation flow edit screen by the processor 31. In the data registration widget 70, a radio button 71, a selected image display 72, a text entry box 73, and a determination button 74 are displayed.

Thereafter, one of the plurality of options (a "normal operation," a "quality important operation," and a "count operation") of the radio button 71 is selected by the processor 31 according to how the input 34 was operated by the editor. Further, when the editor operates the input 34, a text according to how it was operated is entered into the text entry box 73. Further, according to how the input 34 was operated by the editor, one or more image data 48 are selected from the plurality of image data 48 by the processor 31, and the image of the selected image data 48 is displayed on the selected image display 72 by the processor 31. Here, when the option of the "count operation" of the radio button 71 is selected, two or more image data 48 can be selected from the plurality of image data 48, and the images of the selected plurality of image data 48 are displayed in the selected image display 72 by the processor 31 in such a way as arranging them like an array in the selected image display 72. On the other hand, when the option of the "normal operation" or the "quality important operation" of the radio button 71 is selected, one image data 48 can be selected from the plurality of image data 48, and the image of the selected one image data 48 is displayed on the selected image display 72 by the processor 31 in the selected image display 72.

Thereafter, the determination button 74 is selected and determined by the processor 31 according to how the input 34 was operated by the editor. As a result, the main process data 46 associated with the unregistered widget 63 is updated. Specifically, the option selected in the radio button 71 is recorded in the storage 32 by the processor 31 as classification data of the main process data 46 associated with the unregistered widget 63. Further, the text entered into the text entry box 73 is recorded in the storage 32 by the processor 31 as the operation detail data of the main process data 46 associated with the unregistered widget 63.

Furthermore, a unique data (e.g., a file name or an identifier) of the selected image data 48 of the image displayed on the selected image display 72 is recorded in the storage 32 by the processor 31 as the image designation data of the main process data 46 associated with the unregistered widget 63.

When the main process data 46 associated with the unregistered widget 63 is updated as described above, as shown in FIGS. 42A and 42B, an operation flow edit screen is displayed on the display 33 by the processor 31 in such a way as changing the unregistered widget 63 to the registered widget 62. At this time, the processor 31 refers to the updated main process data 46 and generates the registered widget 62 on the operation flow edit screen based on the main process data 46. That is, the processor 31 determines the display text of the operation detail display 62b of the registered widget 62 based on the operation detail data of the updated main process data 46, determines a display image of the instrument display 62a among the plurality of image data 48 based on the image designation data of the main process data 46, and determines the color of the background 62d based on the classification data of the main process data 46. Here, the screen shown in FIG. 42A is an example of the operation flow edit screen before the display of the unregistered widget 63 is changed to the registered widget 62, and the screen shown in FIG. 42B is an example of the operation flow edit screen after the unregistered widget 63 has been changed and displayed as the registered widget 62.

Figure 42A:
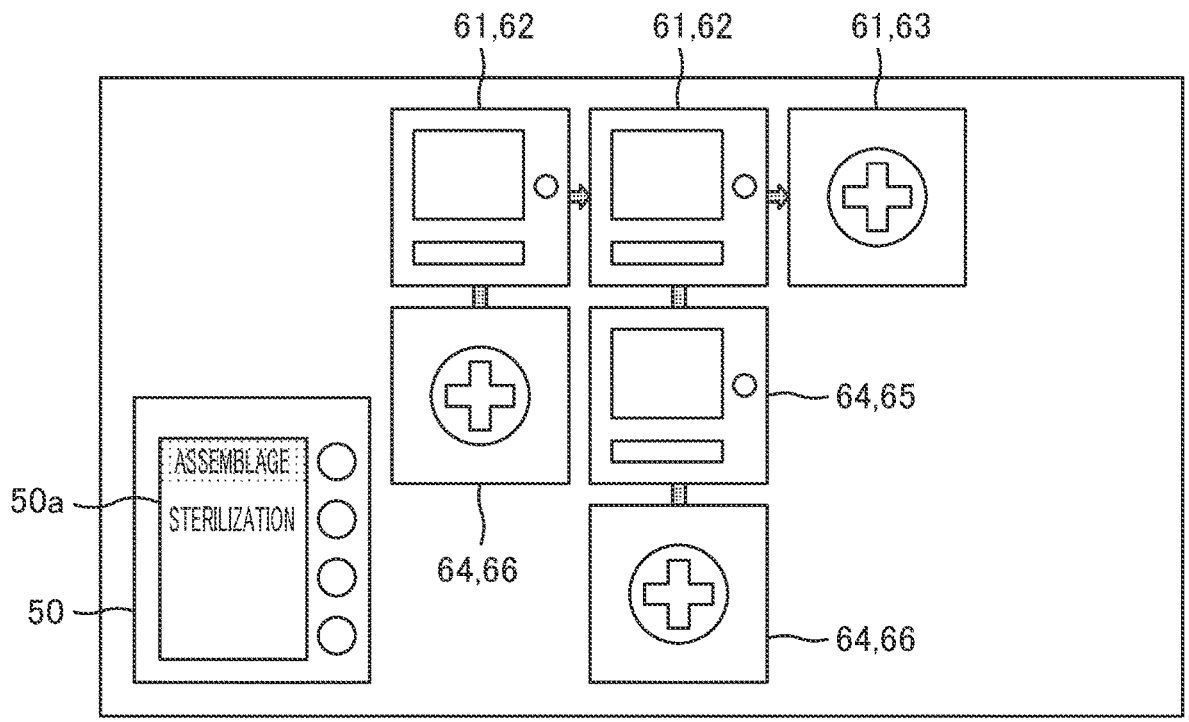
FIG. 42A is a diagram showing the operation flow edit screen before unregistered widgets of a main process are changed to registered widgets.
Figure 42B:
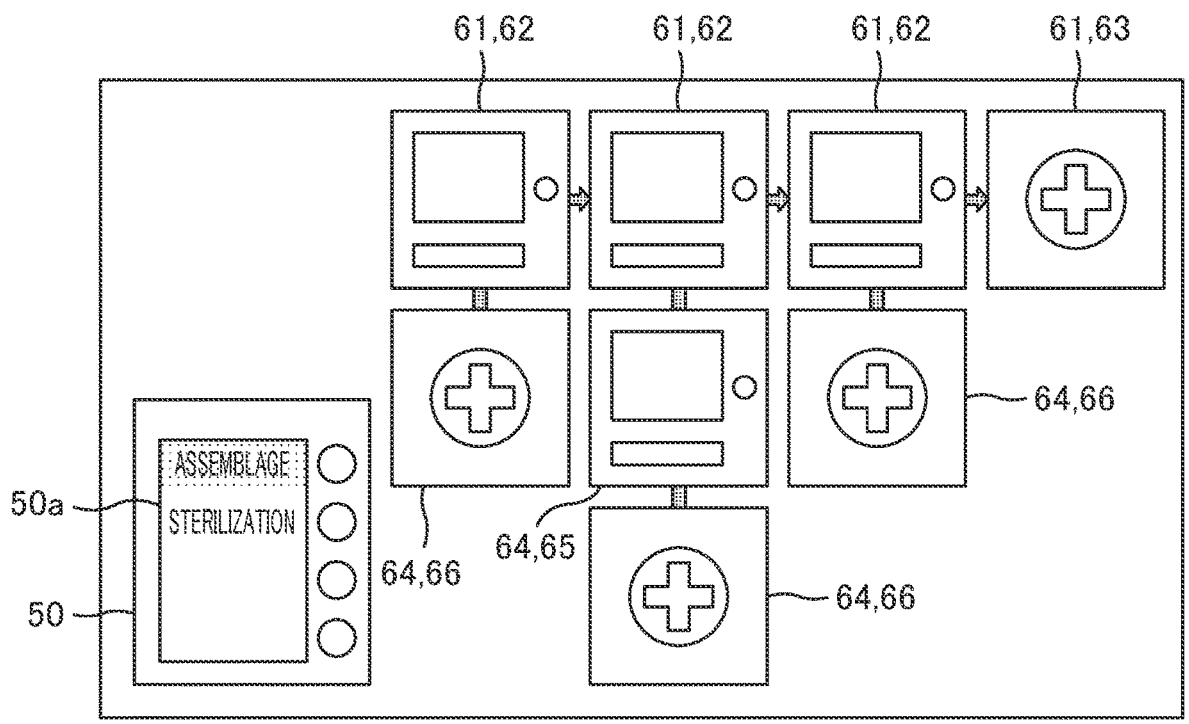
FIG. 42B is a diagram showing the operation flow edit screen after the unregistered widgets of the main process have been changed to registered widgets.
Figure 43A:
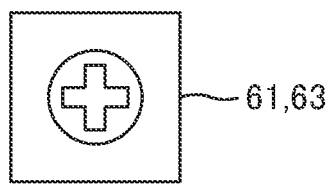
FIG. 43 is a diagram illustrating that unregistered widgets of a main process and a sub process are successively displayed in a lateral direction in the order of 43A to 43D.
Figure 43B:
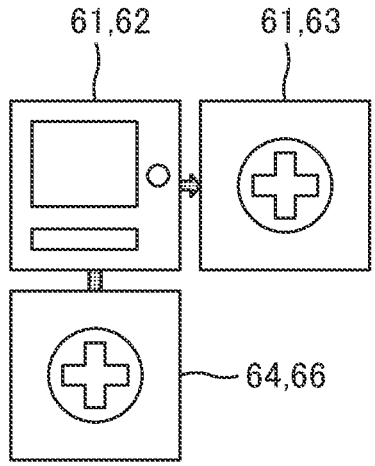
Figure 43C:
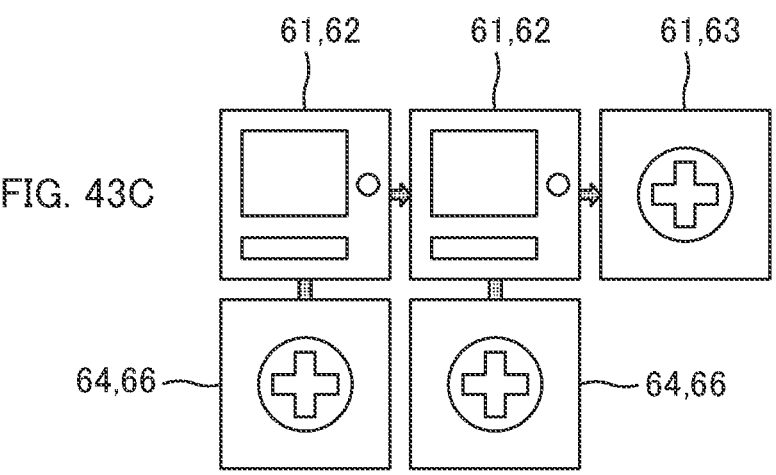
Figure 43D:
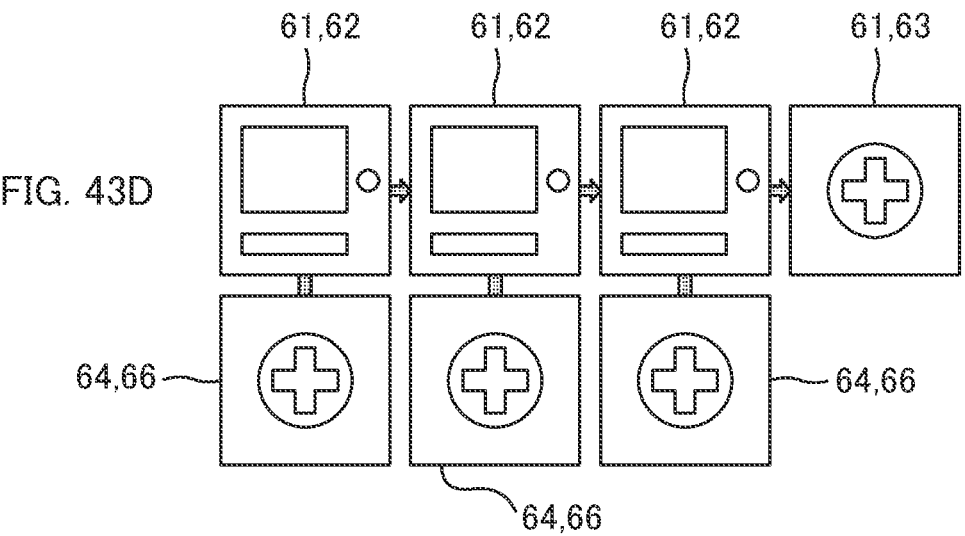

When the unregistered widget 63 is changed to the registered widget 62 as described above, the operation flow edit screen is displayed on the display 33 by the processor 31 in such a way as adding a new sub process widget 64 (in particular, an unregistered widget 66) at a position adjacent to the lower end of the changed registered widget 62 (see FIGS. 42A and 42B). Further, a new sub process data 47 is generated on the storage 32 by the processor 31. A value of the upper-level process order data of the upper-level process data 45 corresponding to the selection list in the list box 50a is registered in the upper-level process order data of the newly generated sub process data 47. The value of the main process order data of the main process data 46 associated with the registered widget 62 changed from the unregistered widget 63 is registered in the main process order data of the newly generated sub process data 47. In addition, a value of "1" is registered in the sub process order data of the newly generated sub process data 47. Since the image designation data and the operation detail data of the newly generated sub process data 47 have not yet been registered at this point of time, a newly displayed sub process widget 64 is the unregistered widget 66 (see FIG. 42B).

When the unregistered widget 63 is changed to the registered widget 62 as described above, the operation flow edit screen is displayed on the display 33 by the processor 31 in such a way as adding a new main process widget 61 (in particular, the unregistered widget 63) at a position adjacent to the right end of the changed registered widget 62 (see FIGS. 42A and 42B). Further, a main process data 46 is generated on the storage 32 by the processor 31. A value of the upper-level process order data of the upper-level process data 45 corresponding to the selection list in the list box 50a is registered in the upper-level process order data of the newly generated main process data 46. A value obtained by adding 1 to the value of the main process order data of the main process data 46 associated with the registered widget 62 changed from the unregistered widget 63 is registered in the main process order data of the newly generated main process data 46. Since the operation detail data, the classification data, and the image designation data of the newly generated main process data 46 are not registered at this point of time, a newly displayed main process widget 61 is the unregistered widget 63 (see FIG. 42B).

Therefore, when the editor repeatedly performs operations as mentioned above, as shown in FIGS. 43A to 43D, the unregistered widgets 63 (the main process widgets 61) and the unregistered widgets 66 (the sub process widgets 64) are displayed successively from the left to the right of the operation flow edit screen as in the order of FIGS. 43A to 43D and the change of the display from the unregistered widget 63 to the registered widget 62 is performed successively from the left to the right of the operation flow edit screen as in the order of FIGS. 43A to D.

Each of the sub process widgets 64 is also classified as the registered widget 65 (see FIG. 39) and the unregistered widget 66 (FIG. 40). The sub process widget 64 can be changed from the unregistered widget 66 to the registered widget 65. Hereinafter, a process of changing the display of the sub process widget 64 from the unregistered widget 66 to the registered widget 65 is described.

When the unregistered widget 66 (in particular, a button 66a) is selected and determined by the processor 31 according to how the input 34 was operated by the editor, the data registration widget 70 (see FIG. 41) is displayed. At this time, however, no radio button 71 is displayed on the data registration widget 70. Then, as in the case of changing the main process widgets 61 from the unregistered widget 63 to the registered widget 62, the editor operates the data registration widget 70 using the input 34 and the sub process data 47 associated with the unregistered widget 66 is updated.

Specifically, the text entered into the text entry box 73 is recorded in the storage 32 by the processor 31 as the operation detail data of the sub process data 47 associated with the unregistered widget 66. Furthermore, a unique data (e.g., a file name or an identifier) of the selected image data 48 of the image displayed on the selected image display 72 is recorded in the storage 32 by the processor 31 as the image designation data of the sub process data 47 associated with the unregistered widget 66.

When the sub process data 47 associated with the unregistered widget 66 is updated as described above, as shown in FIGS. 44A and 44B, an operation flow edit screen is displayed on the display 33 by the processor 31 in such a way as changing the unregistered widget 66 to the registered widget 65. At this time, the processor 31 refers to the updated sub process data 47 and generates the registered widget 65 on the operation flow edit screen based on the sub process data 47. That is, the processor 31 determines the display text of the operation detail display 65*b* of the registered widget 65 based on the operation detail data of the updated sub process data 47 and determines a display image of the instrument display 65*a* among the plurality of image data 48 based on the image designation data of the sub process data 47. Here, the screen shown in FIG. 44A is an example of the operation flow edit screen before the display of the unregistered widget 66 is changed to the registered widget 65, and the screen shown in FIG. 44B is an example of the operation flow edit screen after the unregistered widget 66 has been changed and displayed as the registered widget 65.

Figure 44A:
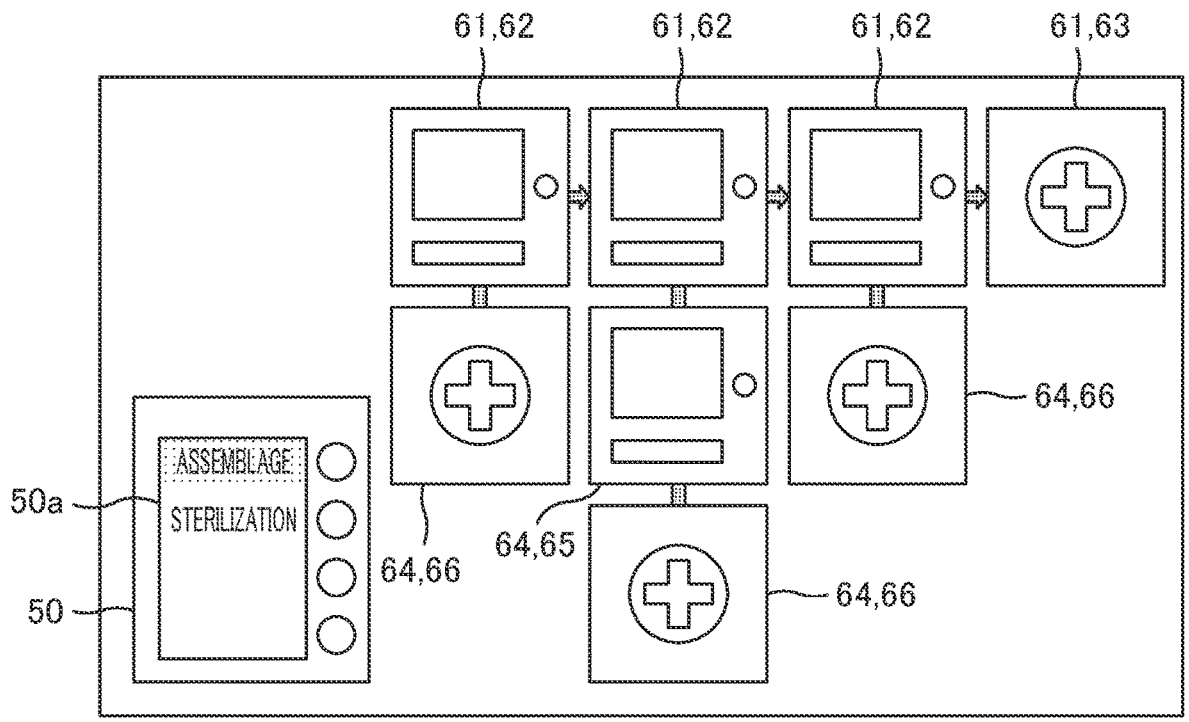
FIG. 44A is a diagram showing the operation flow edit screen before unregistered widgets of a sub process are changed to registered widgets.
Figure 44B:
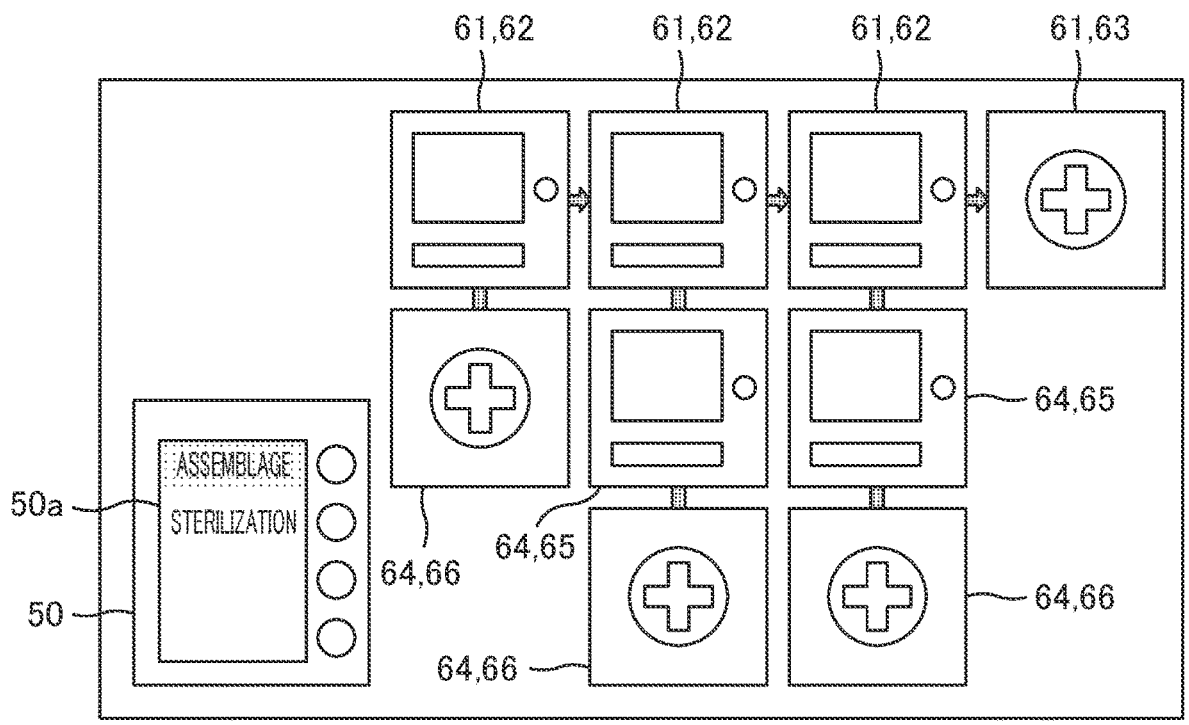
FIG. 44B is a diagram showing the operation flow edit screen after the unregistered widgets of the sub process have been changed to registered widget.

When the unregistered widget 66 is changed to the registered widget 65 as described above, the operation flow edit screen is displayed on the display 33 by the processor 31 in such a way as adding a new sub process widget 64 (in particular, an unregistered widget 66) at a position adjacent to the lower end of the changed registered widget 65 (see FIGS. 44A and 44B). Further, a new sub process data 47 is generated on the storage 32 by the processor 31. A value of the upper-level process order data of the upper-level process data 45 corresponding to the selection list in the list box 50*a* is registered in the upper-level process order data of the newly generated sub process data 47. The value of the main process order data of the main process data 46 associated with the registered widget 65 changed from the unregistered widget 66 is registered in the main process order data of the newly generated sub process data 47. A value obtained by adding 1 to the value of the sub process order data of the main process data 46 associated with the registered widget 65 changed from the unregistered widget 66 is registered in the sub process order data of the newly generated sub process data 47. Since the image designation data and the operation detail data of the newly generated sub process data 47 have not yet been registered at this point of time, a newly displayed sub process widget 64 is the unregistered widget 66 (see FIG. 44B).

Accordingly, when the editor repeatedly performs the above-described operations, as shown in FIGS. 45A to 45D, the unregistered widgets 66 (the sub process widgets 64) are displayed one after another from the top to the bottom of the operation flow edit screen in the order shown in FIGS. 45A to 45D and the change of the display from the unregistered widget 66 to the registered widget 65 is performed successively from the top to the bottom of the operation flow edit screen in the order shown in FIGS. 45A to 45D.

The edit buttons 62*c* and 65*c* are displayed in the registered widgets 62 and 65 (see FIGS. 37 and 39). These edit buttons 62*c* and 65*c* are for changing or deleting a portion of the process data 46 and 47. In other words, when the edit button 62*c* of one of the registered widgets 62 is selected and determined by the processor 31 according to how the input 34 was operated by the editor, it is possible to partially change or delete the main process data 46 associated with the selected registered widget 62.

Thereafter, according to how the input 34 was operated by the editor, the operation detail data, the classification data or the image designation data of the main process data 46 associated with the selected registered widget 62 is changed by the processor 31. The main process data 46 after the change is updated and recorded in the storage 32 by the processor 31. Then, the processor 31 refers to the updated main process data 46, and based on that main process data 46, it changes the display of the instrument display 62*a*, the operation detail display 62*b* or the background 62*d* of the registered widget 62 in the operation flow edit screen.

On the other hand, when the operation detail data, the classification data, and the image designation data of the main process data 46 associated with the selected registered widget 62 are deleted by the processor 31 according to how the input 34 was operated by the editor, the main process data 46 after the change is updated and recorded in the storage 32 by the processor 31. Then, the operation flow edit screen is displayed on the display 33 by the processor 31 in such a way as changing the selected registered widget 62 to the unregistered widget 63.

Similarly, when the edit button 65*c* of one of the registered widgets 65 is selected and determined by the processor 31 by the editor's operating the input 34, it is possible to partially change or partially delete the sub process data 65 associated with the selected registered widget 65.

The raising buttons 62*e* and 65*e* and the lowering buttons 62*f* and 65*f* are arranged in the registered widgets 62 and 65 (see FIGS. 37 and 39). The raising buttons 62*e* and 65*e* are for moving up the order of the registered widgets 62 and 65 and the lowering buttons 62*f* and 65*f* are for moving down the order of the registered widgets 62 and 65. That is, when the raising button 62*e* (or the lowering button 62*f*) of one of the registered widgets 62 (the main process widgets 61) is selected and determined by the processor 31 by the editor's operating the input 34, the processor 31 causes the display 33 display the operation flow edit screen in such a way as permuting a column of the selected registered widget 62 (the main process widget 61) and the underneath sub process widget and a column of the main process widget 61 and the underneath sub process widget 64 next to the selected registered widget (the main process widget 61) on its left (on its right for the lowering button 62*f*). Along with this, the processor 31 replaces the main process order data of the process data 46 and 47 associated with the selected process widgets 61 and 64 with the main process order data of the process data 46 and 47 associated with the process widgets 61 and 64 on their left (or on their right for the lowering button 62*f*) and updates and records the process data 46 and 47 after the replacement in the storage 32.

As described above, for the editor, replacement of the two main process widgets 61 and replacement of the orders of the main process can be easily achieved.

When the raising button 65*e* (or the lowering button 65*f*) of one of the registered widgets 65 (the sub process widgets 64) is selected and determined by the processor 31 by the editor's operating the input 34, the processor 31 causes the display 33 display the operation flow creation screen in such a way as permuting the selected sub process widget 64 and the adjacent sub process widget 64 above (underneath for the lowering button 65*f*). Along with this, the processor 31 replaces the sub process order data of the sub process data 47 associated with the selected sub process widget 64 with the sub process order data of the sub process data 47 associated with the sub process widget 64 above (or underneath for the lowering button 65*f*) and updates and records the sub process data 47 after the replacement in the storage 32.

As described above, for the editor, replacement of the two sub process widgets 64 and replacement of the orders of the sub process can be easily achieved.

When a printer is connected to the terminal 3-1, printing can be performed. That is, when the editor operates the input 34 to cause the processor 31 execute a printing process, the processor 31 converts the area 60 of the operation flow edit screen into print data and transmits the print data to the printer. As a result, the image of the area 60 of the operation flow edit screen is formed on the medium (for example, paper) by the printer.

By using the system 1 as described above, it is possible to easily create a manual (the screen transition achieve by the display program 104) of handling operations for medical instruments. In other words, the GUI operation flow edit screen is superior in visibility and operability, and the editor can intuitively operate the GUI operation flow edit screen with the input 34 while looking at the operation flow edit screen of the display 33.

In addition, as described above, when the operation detail data, the image designation data and the classification data are added to the main process data 46 associated with the unregistered widget 63, the unregistered widget 63 is changed to the registered widget 62 and the unregistered widget 63 is automatically displayed on its right and the unregistered widget 66 is automatically displayed underneath. Therefore, even an editor unfamiliar with the user interface can intuitively continue to create the process data 46 and 47 associated with the newly displayed unregistered widgets 63 and 66. In other words, it is possible to continuously create a manual of handling operations for medical instruments.

In addition, as described above, when the operation detail data, the image designation data, and the classification data are added to the sub process data 47 associated with unregistered widget 66, the unregistered widget 66 is changed to the registered widget 65, and the unregistered widget 66 is automatically displayed below. Therefore, even an editor unfamiliar with the user interface can intuitively continue to create the process data 47 associated with the newly displayed unregistered widget 66. In other words, it is possible to continuously create a manual of handling operation procedures for medical instruments.

Furthermore, by using the data registration widget 70 as shown in FIG. 41, it is possible to easily enter the operation detail data, the image designation data, and the classification data into the process data 46 and 47.

Moreover, since the registered widgets 62 (the main process widgets 61) are aligned in the order of processes, the editor can intuitively recognize the order of the main processes of the handling operations for medical instruments. The order of the sub processes of the main processes can also be recognized intuitively by the registered widgets 65 (the sub process widgets 64).

Regardless of which editor or editors create(s) a manual (the screen transition achieved by the display program 104) of handling operations for medical instruments using the system 1, the manual follows a certain style (template). Therefore, regardless of which editor or editors create(s) a manual, the quality of the manual satisfies certain criteria.

The management program 102 has been installed in the OS of the basic program 101 and can be executed by the processor 31 on the OS.

As described above, the operation flow content is edited by the editing program 103. The management program 102 is for managing versions of the operation flow content. The operation flow content is used by the display program 104 whereas the management program 102 is for managing the use history of the operation flow content. Since a plurality of operation flow contents are compiled into a database and stored in the storage 32 for managing the versions and the use history of the operation flow contents, the database is described first.

Figure 46:
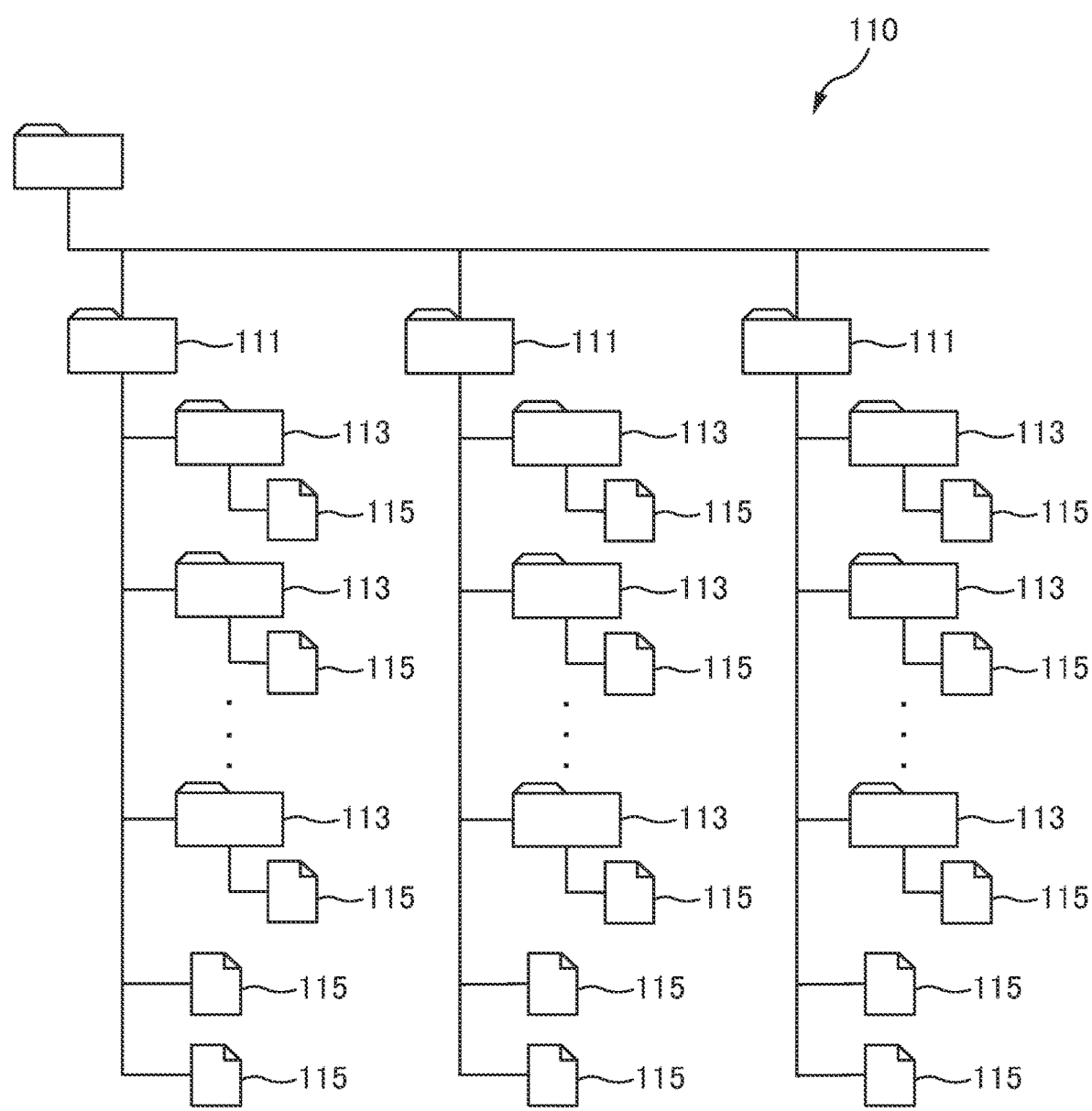
FIG. 46 is a diagram schematically showing a hierarchical structure of a contents database.

As shown in FIG. 32, the contents database 110 in which a plurality of operation flow contents are stored is constructed in the storage 32. Here, each operation flow content is stored in the contents database 110 in a hierarchical structure as shown in FIG. 46 for management of each version (edition). FIG. 46 is a schematic diagram for explaining the hierarchical structure of the contents database 110. In the contents database 110, a folder 111 for storing a content (hereinafter, referred to as a storage folder 111) is prepared for each operation flow content, and one operation flow content is stored in and associated with one storage folder 111. Then, each operation flow content can be identified by its unique identifier. For example, the name of the storage folder 111 is a unique identifier of the operation flow content, and every operation flow content can be distinguished from other operation flow contents according to the names of the storage folders 111.

In the storage folder 111, a folder 113 for storing a version (hereinafter, referred to as a version folder 113) is prepared for each version of the operation flow content, and one version of the operation flow content is stored in one version folder 113 as a file 115. Then, the version (the file 115) of the operation flow content can be identified by its unique version number. For example, the name of the version folder 113 is a unique version number. According to the names of the version folders 113, every version and file 115 can be distinguished from others and version numbers can be identified.

In the storage folder 111, a version management table 117 for managing versions of the operation flow content stored in and associated with that storage folder 111 is stored. By storing the version management table 117 in the storage folder 111, the version management table 117 and the operation flow content stored in the storage folder 111 are associated with each other.

FIG. 47 is a diagram showing an exemplified configuration of the version management table 117. The version management table 117 is made up of pieces of information 119 (hereinafter, each piece of information is referred to as version information 119) for each version (for each file 115), and one version information 119 per one file 115 (one version) is included in the version management table 117. The version information 119 includes a piece of information 121 indicating its version number (which version of the operation flow content the file 115 is), a piece of information 122 indicating an identifier of the operation flow content in the version, a piece of information 123 indicating the name of the operation flow content in that version, a piece of information 124 indicating an address (a storage location) of the file 115 of that version, a piece of information 125 indicating the time at which the file 115 of that version was stored, a piece of information 126 indicating an editor (e.g., a user ID) who stored the file 115 of that version, a piece of information 127 indicating a reason for editing the operation flow content of that version, a piece of information 128 indicating an approver (e.g., a user ID) who approved that version, and a piece of information 129 indicating the time at which that version was approved. By causing these pieces of information 121 to 129 be associated with each other, the version information 119 is composed.

When an operation flow content is newly registered in the contents database 110, a new storage folder 111 and a subordinate new version folder 113 are created in the contents database 110 by the processor 31 and the operation flow content being edited that has been stored in the work area 105 is stored in the new version folder 113 as a file 115 of the latest version (first version).

When the operation flow content is updated and registered in the contents database 110, a new version folder 113 is created in the storage folder 111 by the processor 31, and the operation flow content being edited that has been stored in the work area 105 is stored in the version folder 113 as the latest version of the file 115.

As shown in FIG. 46, in the storage folder 111, a use history log 130 for recording and accumulating the use history of the operation flow content stored in and associated with the storage folder 111 is stored. By storing the use history log 130 in the storage folder 111, the operation flow content stored in that storage folder 111 and the use history log 130 are associated with each other.

FIG. 48 is a diagram showing an exemplified configuration of the use history log 130. The use history log 130 includes pieces of information 131 for each use of the operation flow content (hereinafter, each piece of information is referred to as use information 131), and one use information 131 is included in the use history log 130 for one use of the operation flow content. The use information 131 includes a piece of information 132 indicating the use time of the operation flow content, a piece of information 133 indicating the used version, a piece of information 134 indicating the time of use of the operation flow content, and a piece of information 135 indicating a user (e.g., a user ID) of the operation flow content. By causing these pieces of information 132 to 135 to be associated with each other, the use information 131 is provided.

The use of the operation flow means that the file 115 of one of the versions of the operation flow content is opened by the display program 104. When the file 115 of one of the versions of the operation flow content is opened by the display program 104, the use information 131 is added to and registered in the use history log 130.

Figure 49:
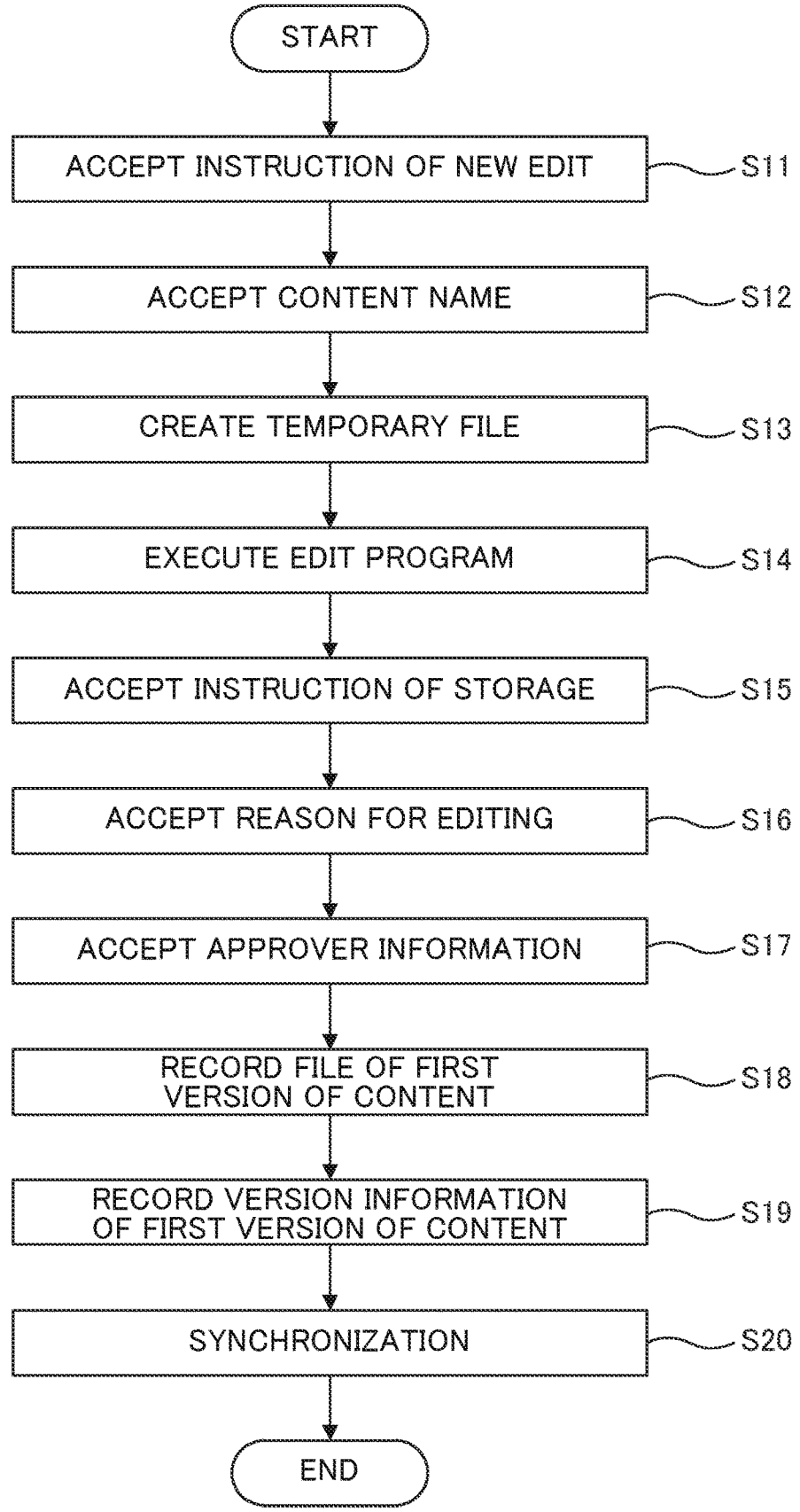
FIG. 49 is a flow chart showing a flow of a version management processing in editing a new operation flow content.

With reference to a flowchart shown in FIG. 49, a flow of processing that the management program 102 causes the processor 31 to execute in editing a new operation flow content is described. It should be noted that if the work area 105 has a temporary file 44 at the beginning of the processing flow described below, the processor 31 erases the temporary file 44.

When the editor who has logged in with his own user ID and password operates the input 34 and enters that a new edit is going to be made, the processor 31 accepts it (step S 11). Then, the processor 31 causes the display 33 display a name input screen of the operation flow content. Thereafter, when an editor enters the name of the operation flow content with the input 34, the processor 31 accepts the input (the name of the operation flow content) and stores it (step S12).

Subsequently, the processor 31 creates a work area 105 in the storage 32, and creates a temporary file 44 as a new operation flow content in the work area 105 (step S13). Then, the processor 31 executes the edit program 103 (step S14). When the edit program 103 is executed, a GUI (the operation flow edit screen shown in FIG. 36) is achieved, and edition of the new operation flow content (the temporary file 44) becomes possible. That is, while looking at the display screen of the display 33, the editor can edit the operation flow content, that is, the temporary file 44 by operating the input 34.

After editing the operation flow content, when the editor operates the input 34 and enters an instruction of storage, the processor 31 accepts this (step S15). Then, the processor 31 causes the display 33 display an input screen of a reason for editing the operation flow content. Thereafter, when the editor enters the reason for editing the operation flow content with the input 34, the processor 31 accepts the input (the reason for editing the operation flow content) and stores it (step S16). Further, when the processor 31 causes the display 33 display an input screen of an approver identifier (e.g., a user ID), and thereafter the editor enters the approver identifier with the input 34, the processor 31 accepts the input and stores it (step S17). It should be noted that instead of selecting the approver by the editor as in the step S17, a default approver identifier may be set in advance.

Thereafter, the processor 31 creates a new storage folder 111 in the contents database 110 of the storage 32, creates a new version folder 113 therein, and stores the temporary file 44 being edited that has been stored in the work area 105 as the file 115 in the version folder 113 (step S18). This file 115 is the first version of the operation flow content.

Thereafter, the processor 31 creates the version management table 117 in the storage folder 111 and records the version information 119 in the version management table 117 (step S19). Specifically, the processor 31 records the version number (specifically, No. 1) of the file 115 that has been recorded in the step S18 as the value of the version number information 121 of the version information 119, records the identifier of the operation flow content of that version as the value of the identifier information 122 of the version information 119, records the name of the operation flow content accepted in the step S12 as the value of the name information 123, records the address of the file 115 as the value of the address information 124, records the recording time of the file 115 as the value of the time information 125, records the user ID used by the editor for logging in as the value of the editor information 126, records the reason for editing accepted in the step S16 as the value of the editing reason information 127, and records the approver identifier accepted in the step S17 as the value of the approver information 128.

Thereafter, the processor 31 executes a synchronization processing and transfers the version information 119 of the version management table 117 and the file 115 recorded as described above to the server 2 (step S20). As a result, the database 110 of the storage 32 is also synchronized with the storage of the server 2, and the database 110 is also synchronized with the other terminals 3-2 and 3-3 by the server 2.

Figure 50:
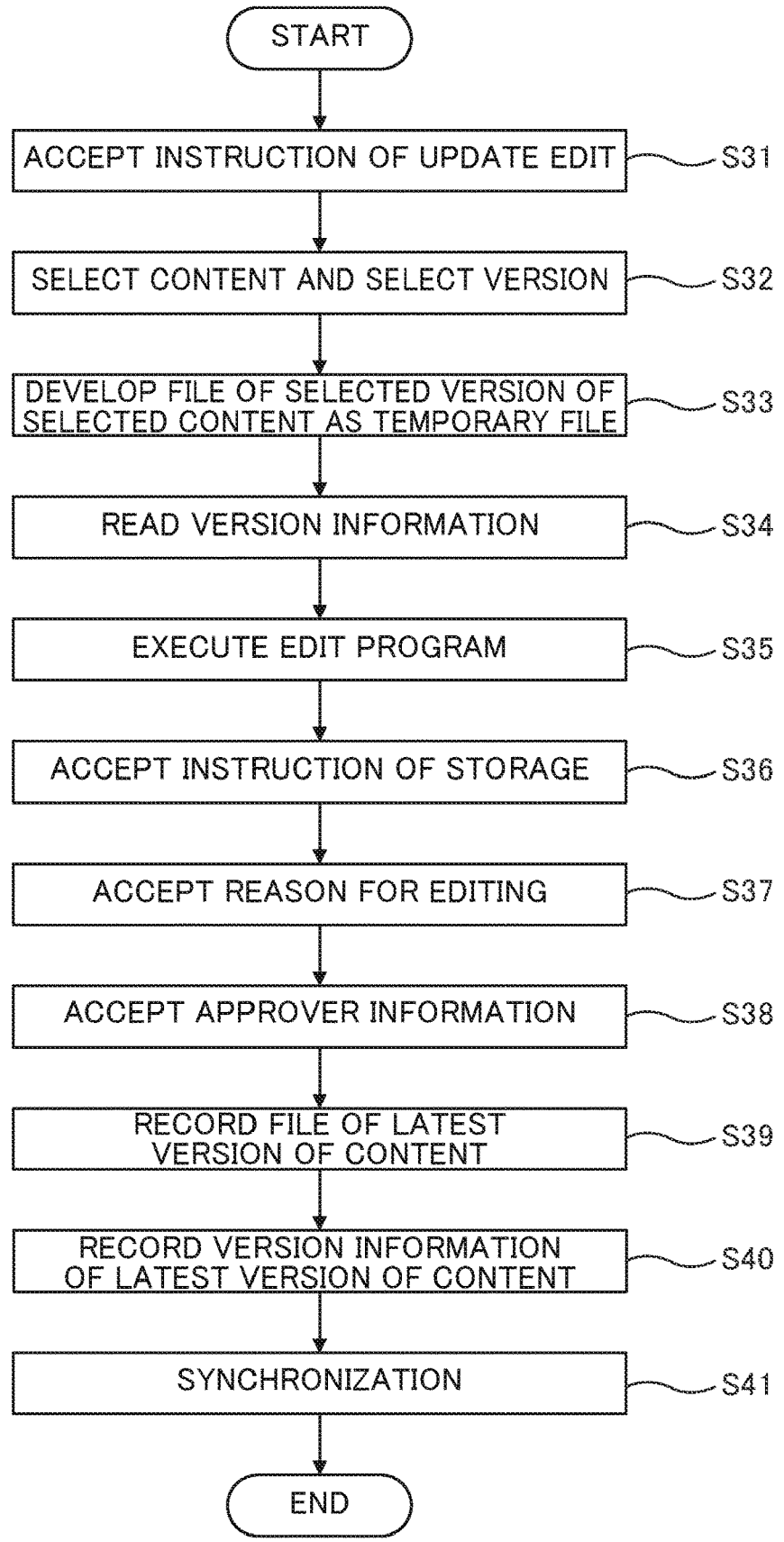
FIG. 50 is a flow chart showing a flow of a version management processing in editing an existing operation flow content.

With reference to a flowchart shown in FIG. 50, a flow of processing that the management program 102 causes the processor 31 to execute in editing an existing operation flow content is described. It should be noted that if the work area 105 has a temporary file 44 at the beginning of the processing flow described below, the processor 31 erases the temporary file 44.

When the editor who has logged in with his own user ID and password operates the input 34 and enters that an update edit is going to be made, the processor 31 accepts it (step S 31). Then, the processor 31 causes the display 33 display a screen for selecting an operation flow content and a version. Then the editor selects and enters one of the plurality of operation flow contents with the input 34, and further selects and enters one of the versions of that operation flow content, whereby the processor 31 selects the storage folder 111 of the selected workflow content and selects the version folder 113 of the selected version (step S32). Then, the processor 31 reads the file 115 in that version folder 113, and develops the file 115 as the temporary file 44 in the work area 105 (step S33). Further, the processor 31 reads and stores the version information 119 of the selected version from the version information 119 of the version management table 117 stored in the storage folder 111 of the selected operation flow content (step S34).

Then, the processor 31 executes the edit program 103 (step S35). When the edit program 103 is executed, a GUI (the operation flow edit screen shown in FIG. 36) is achieved, and edition of the existing operation flow content (the temporary file 44) becomes possible. That is, while looking at the display screen of the display 33, the editor can edit the operation flow content, that is, the temporary file 44 by operating the input 34.

After editing the operation flow content, when the editor operates the input 34 and enters an instruction of storage, the processor 31 accepts this (step S36). Then, the processor 31 causes the display 33 display an input screen of a reason for editing the operation flow content. Thereafter, when the editor enters the reason for editing the operation flow content with the input 34, the processor 31 accepts the input (the reason for editing the operation flow content) and stores it (step S37). Further, when the processor 31 causes the display 33 to display an input screen of an approver identifier (e.g., a user ID), and thereafter the editor enters the approver identifier with the input 34, the processor 31 accepts the input and stores it (step S38). It should be noted that instead of selecting the approver by the editor as in the step S28, a default approver identifier may be set in advance.

Thereafter, the processor 31 creates a new version folder 113 in the selected storage folder 111 and stores the temporary file 44 being edited that has been stored in the work area 105 as the file 115 in the version folder 113 (step S39). This file 115 is the latest version of the operation flow content.

Thereafter, the processor 31 records a new version information 119 in the version management table 117 of the selected storage folder 111 (step S40). Specifically, the processor 31 records the version number (specifically, the latest version number) of the file 115 that has been recorded in the step S29 as the value of the version number information 121 of the version information 119, records the identifier of the operation flow content of that version as the value of the identifier information 122 of the version information 119, records the name information 123 of the version information 119 that has been read in the step S34 as a new name information 123 of the version information 119, records the address of the file 115 that has been recorded in the step S39 as the value of the address information 124, records the recording time of the file 115 that has been recorded in the step S39 as the value of the time information 125, records the user ID used by the editor for logging in as the value of the editor information 126, records the reason for editing accepted in the step S37 as the value of the editing reason information 127, and records the approver identifier accepted in the step S38 as the value of the approver information 128.

Thereafter, the processor 31 executes a synchronization processing and transfers the version information 119 of the version management table 117 and the file 115 recorded as described above to the server 2 (step S41). As a result, the database 110 of the storage 32 is also synchronized with the storage of the server 2, and the database 110 is also synchronized with the other terminals 3-2 and 3-3 by the server 2.

A flow of an approval time record processing which the management program 102 causes the processor 31 to execute after editing and storing a new or existing operation flow content is described.

When a user (an approver) logs in with his own user ID and password, the processor 31 searches the version management table 117 for the version information 119 for which the value of the approver information 128 matches the login user ID and the approval time information 129 has not yet been recorded. Then, the processor 31 causes the display 33 display the name information 123 and the version number information 121 of the retrieved version information 119 together with an approval button. This causes a notice to the login user. Then, if approving the version of the operation flow content, the user selects and determines the approval button of the version by operating the input 34. Then, the processor 31 records the time of the selection and determination of the approval button as the value of the approval time information 129 in the version management table 117 with association to the version number information 121 of the approved version. The file 115 of the version approved in this way is made usable as described above, and the file 115 of the unapproved version cannot be used in a medical instrument handling operation and screen transition described above.

Figure 51:
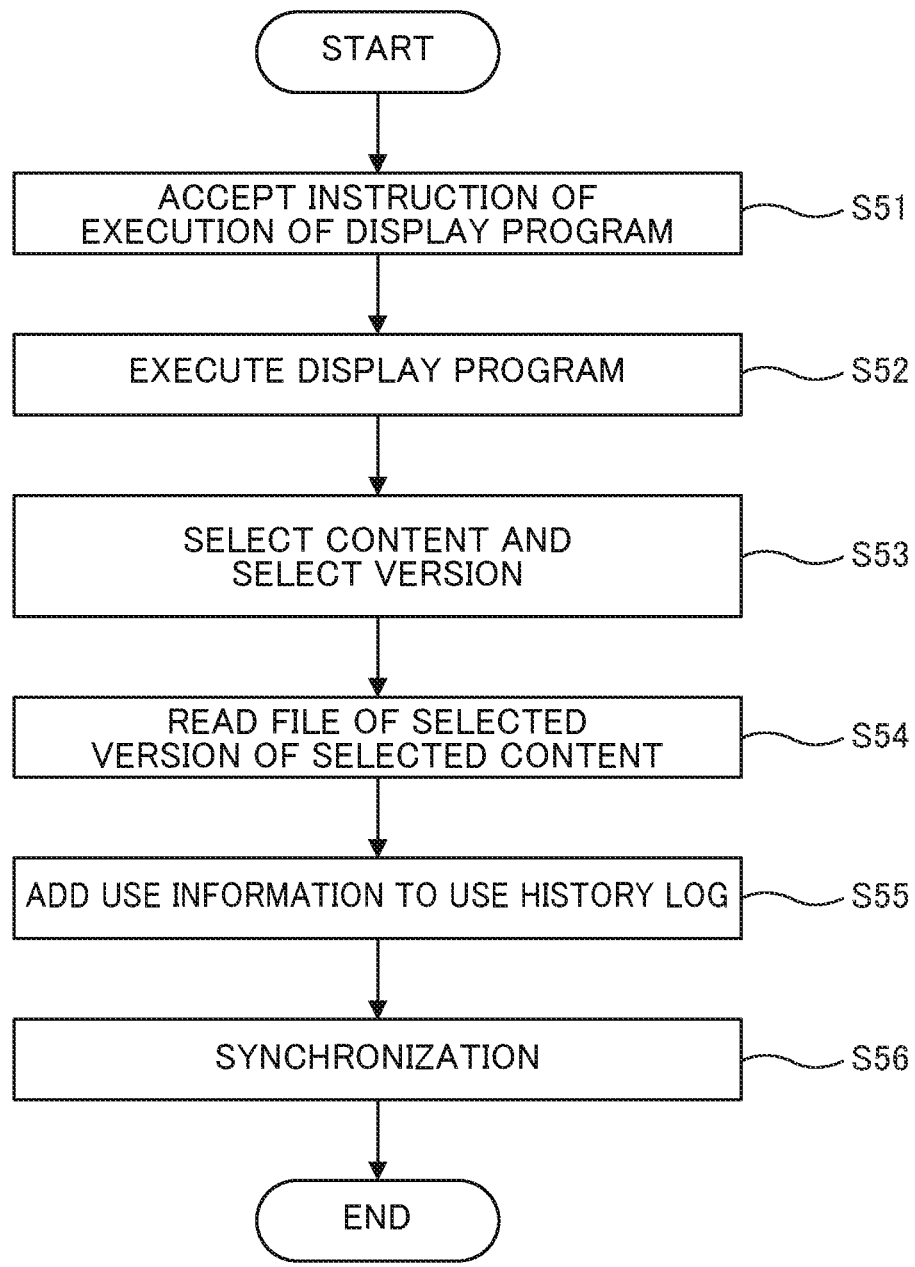
FIG. 51 is a flow chart showing a flow of a use history management processing.

With reference to a flowchart shown in FIG. 51, a flow of a use history management processing that the management program 102 causes the processing device 31 to execute after editing and storing a new or existing operation flow content is described.

When an operator (user) who has logged in with his own user ID and password operates the input 34 and enters an instruction of executing the display program 104, the processor 31 accepts this (step S51). Then, the processor 31 activates and executes the display program 104 (step S52).

Thereafter, the processor 31 causes the display 33 display a screen used to select an operation flow content and a version. Then the editor selects and enters one of the plurality of operation flow contents with the input 34, and further selects and enters one of the versions of that operation flow content, whereby the processor 31 selects the storage folder 111 of the selected workflow content and selects the version folder 113 of the selected version (step S53). Then, the processor 31 reads the file 115 in that version folder 113, and opens the file 115 with the display program 104 (step S54). Then, the processor 31 controls the display 33 in such a way that the screen transition (for example, the screens A to D, B1, B2, D1, and D2) according to the file 115 proceeds depending on the operation of the input 34 by the operator. Instead of selecting the version by the operator as in the step S53, the file 115 of the latest version folder 113 of the selected operation flow content may be opened in the display program 104.

Thereafter, the processor 31 adds and records the use information 131 (the use time information 132, the use version information 133, the time-of-use information 134, and the user information 135) in the use history log 130 of the selected storage folder 111 (step S55). Specifically, the processor 31 records the sum obtained by adding 1 to the value of the maximum use time information 132 before recording as the value of the use time information 132. Furthermore, the processor 31 records the version of the file 115 that has been read in the step S54 as the value of the use version information 133. Furthermore, the processor 31 records the time at which the file 115 was read in the step S54 as the value of the time-of-use information 134. Moreover, the processor 31 records the user ID of the user who has logged in as the value of the user information 135.

Thereafter, the processor 31 executes a synchronization processing, and transfers the use information 131 of the use history log 130 that has been recorded as described above to the server 2 (step S56). As a result, the use history log 130 of the storage 32 is also synchronized with the storage of the server 2, and that use history log 130 is also synchronized with the other terminals 3-2 and 3-3 by the server 2.

According to the above preferred embodiment, the following effects can be obtained.

(1) Since the files 115 of each version of each operation flow content are organized in a hierarchical structure and stored in the contents database 110, it is very easy to know details of revisions of each operation flow content.

(2) Since the version information 119 is recorded every time an operation flow content is revised, it is possible to know the number of each version, the storage time (revision time), the reviser (editor), and the reason for revision (editing reason).

(3) Since the use information 131 is recorded every time the operation flow content is used, it is possible to know the use history of the operation flow content, that is, which version is used by whom and when.

In the above preferred embodiments, the operation flow content is edited using the terminal 3-1, but the operation flow content may be edited using the terminal 3-2, 3-3 or the server 2.

In the above preferred embodiments, each image data 48 shows a medical instrument and a manual to be created (the screen transition achieved by the file 115 and the display program 104) is the manual of handling operations for medical instruments.

In the above preferred embodiments, each image data 48 shows a medical instrument and the manual to be created (the screen transition achieved by the operation flow content 44 and the display program 42) is the manual of handling operations for medical instruments. On the other hand, the image data 48 may show items other than medical instruments (a display screen of a display displayed by application software, a personal computer, a mobile phone, a home appliance, household goods, furniture, a fitting, a machine tool, a cutting machine, etc.), and the manual to be created (the screen transition achieved by the file 115 and the display program 104) may be a manual of handling operations for articles other than medical instruments.

While the term "widget" is used in the aforementioned description, terms "applet" and "gadget" also have similar meanings.

It is also possible to supply a program to a computer using a non-transitory computer-readable medium with an executable program thereon in the above preferred embodiment(s). Examples of the non-transitory computer-readable medium include magnetic storage media (e.g. flexible disks, magnetic tapes, and hard disk drives), and CD-ROMs (read only memories).

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A medical instrument display comprising:
    an image storage that stores a plurality of image data of a medical instrument;
    a data analyzer that searches image data stored in the image storage on a certain condition; and
    a display controller that causes a first display portion of a display to display a first medical instrument image that has been selected by a user from thumbnail images that are based on a plurality of the image data obtained by the search, and a second display portion of the display to display a second medical instrument image that is different from the first medical instrument image, wherein the second medical instrument image has been selected by the user from the thumbnail images,
    the display controller causes the display to display the first display portion and the second display portion at the same time, and
    the display controller causes the display to display a first change button in the first display portion that is able to be chosen by the user when the first medical instrument image to be displayed is selected by the user, a second change button in the second display portion that is able to be chosen by the user when the second medical instrument image to be displayed is selected by the user, a first OK button in the first display portion that is able to be chosen by the user when the first medical instrument image is to be displayed, and a second OK button in the second display portion that is able to be chosen by the user when the second medical instrument image is to be displayed.

2. The medical instrument display according to claim 1, wherein the image data of the medical instrument are associated with image data of another medical instrument, and the display controller causes, based on an image data of the another medical instrument associated with the first medical instrument image, the second medical instrument image to be displayed.

3. The medical instrument display according to claim 1, wherein the display controller is capable of causing the display to display either one of the first medical instrument image or the second medical instrument image in such a case that the user selects a predetermined button displayed by the display.

4. The medical instrument display according to claim 1, wherein the display controller allows a designated area to be enlarged and displayed, the designated area being in the first medical instrument image or the second medical instrument image that has been displayed.

5. The medical instrument display according to claim 1, wherein
    the image data of a medical instrument are associated with an enlarged image data in which the medical instrument has been partially enlarged; and
    the display controller allows an image based on the enlarged image data to be displayed.

6. The medical instrument display according to claim 1, wherein
    the medical instrument is a set including a plurality of instruments;
    the image data of the medical instrument are associated with image data of each of the instruments included in the set; and
    the display controller allows images based on the image data of the respective instruments to be displayed.

7. A non-transitory computer-readable medium storing a medical instrument display program for causing a computer including an image storage that stores a plurality of image data of a medical instrument and a display, to:
    search the image data stored in the image storage on a certain condition;
    cause the display to display thumbnail images that are based on a plurality of the image data obtained by the search;
    cause a first display portion of the display to display a first medical instrument image selected by a user from the thumbnail images;

cause a second display portion that is different from the first display portion to display a second medical instrument image that is different from the first medical instrument image;

cause the display to display the first display portion and the second display portion at the same time; and cause the display to display a first change button in the first display portion that is able to be chosen by the user when the first medical instrument image to be displayed is selected by the user, a second change button in the second display portion that is able to be chosen by the user when the second medical instrument image to be displayed is designated, a first OK button in the first display portion that is able to be chosen by the user when the first medical instrument image is to be displayed, and a second OK button in second first display portion that is able to be chosen by the user when the second medical instrument image is to be displayed, wherein the second medical instrument image has been selected by the user from the thumbnail images.

* * * * *